US012797438B2

(12) United States Patent
Seo et al.

(10) Patent No.: US 12,797,438 B2

(45) Date of Patent: Nov. 17, 2026

(54) ANTIMICROBIAL PEPTOID HAVING IMPROVED SELECTIVITY AND ANTIMICROBIAL COMPOSITION COMPRISING SAME

(71) Applicant: GWANGJU INSTITUTE OF SCIENCE AND TECHNOLOGY, Gwangju (KR)

(72) Inventors: Jiwon Seo, Gwangju (KR); Dongmin Shin, Gwangju (KR); Jieun Choi, Gwangju (KR); Minsang Kim, Seongnam-si (KR)

(73) Assignee: GWANGJU INSTITUTE OF SCIENCE AND TECHNOLOGY (KR)

( * ) Notice: Subject to any disclaimer, the term of this patent is extended or adjusted under 35 U.S.C. 154(b) by 504 days.

(21) Appl. No.: 18/555,234

(22) PCT Filed: Apr. 14, 2022

(86) PCT No.: PCT/KR2022/005387

§ 371 (c)(1),
(2) Date: Oct. 12, 2023

(87) PCT Pub. No.: WO2022/234972

PCT Pub. Date: Nov. 10, 2022

(65) Prior Publication Data

US 2024/0226228 A1 Jul. 11, 2024

(30) Foreign Application Priority Data

May 6, 2021 (KR) ........................ 10-2021-0058480
Apr. 11, 2022 (KR) ........................ 10-2022-0044371

(51) Int. Cl.
*A61K 38/10* (2006.01)
*A61P 31/04* (2006.01)

(52) U.S. Cl.
CPC .............. *A61K 38/10* (2013.01); *A61P 31/04* (2018.01)

(58) Field of Classification Search
CPC .......... A61K 38/10; A61P 31/04; A01N 37/46
See application file for complete search history.

(56) References Cited

U.S. PATENT DOCUMENTS

2010/0222255 A1 9/2010 Kirshenbaum et al.

FOREIGN PATENT DOCUMENTS

JP 2011511077 A 4/2011
KR 20190110061 A * 9/2019 .............. C07K 7/08

OTHER PUBLICATIONS

Zuckermann, Ronald N., et al. "Efficient method for the preparation of peptoids [oligo (N-substituted glycines)] by submonomer solid-phase synthesis." Journal of the American Chemical Society 114.26 (1992): 10646-10647. (Year: 1992).*

Molchanova, Natalia, Paul R. Hansen, and Henrik Franzyk. "Advances in development of antimicrobial peptidomimetics as potential drugs." Molecules 22.9 (2017): 1430. (Year: 2017).*

Wang, Xiaoling, et al. "Potential aggregation prone regions in biotherapeutics: a survey of commercial monoclonal antibodies." MAbs. Vol. 1. No. 3. Taylor & Francis, 2009. (Year: 2009).*

Bolognesi, Benedetta, et al. "Single point mutations induce a switch in the molecular mechanism of the aggregation of the Alzheimer's disease associated Aβ42 peptide." ACS Chemical Biology 9.2 (2014): 378-382. (Year: 2014).*

Sawai, Monali V., et al. "Impact of single-residue mutations on the structure and function of ovispirin/novispirin antimicrobial peptides." Protein engineering 15.3 (2002): 225-232. (Year: 2002).*

Lazzaro, Brian P., Michael Zasloff, and Jens Rolff "Antimicrobial peptides: Application informed by evolution." Science 368.6490 (2020): eaau5480. (Year: 2020).*

Mercer, Derry K., et al. "Antimicrobial susceptibility testing of antimicrobial peptides to better predict efficacy." Frontiers in cellular and infection microbiology 10 (2020): 326. (Year: 2020).*

Roux, Stéphane, et al. "Elimination and exchange of trifluoroacetate counter-ion from cationic peptides: a critical evaluation of different approaches." Journal of peptide science: an official publication of the European Peptide Society 14.3 (2008): 354-359. (Year: 2008).*

Crystal Quest (https://crystalquest.com/blogs/ion-exchange/anion-exchange-resin, accessed Mar. 17, 2026 (Year: 2026).*

Chongsiriwatana, Nathaniel P., et al. "Peptoids that mimic the structure, function, and mechanism of helical antimicrobial peptides." Proceedings of the National Academy of Sciences 105.8 (2008): 2794-2799. (Year: 2008).*

International Search Report for PCT/KR2022/005387 mailed Jul. 28, 2022.

Internet Webpage, "TFA removal service: switch to acetate or HCl salt form of peptide.", Nov. 12, 2020, retrieved from https://web.archive.org/web/20201112012819/https://www.lifetein.com/TFA_Removal_Peptide_Synthesis_Services.html., pp. 1-4.

Lee, Jiyoun et al., "Effect of side chain hydrophobicity and cationic charge on antimicrobial activity and cytotoxicity of helical peptoids", Bioorganic & Medicinal Chemistry Letters, vol. 28, Issue 2, Jan. 15, 2018, pp. 170-173.

* cited by examiner

*Primary Examiner* — Lianko G Garyu

*Assistant Examiner* — David Paul Bowles

(74) *Attorney, Agent, or Firm* — Renaissance IP Law Group LLP

(57) ABSTRACT

The present inventive concept relates to an antimicrobial peptoid having improved selectivity and an antimicrobial composition comprising same. The antimicrobial peptoid according to the present inventive concept exhibits excellent antimicrobial activity against bacteria and low cytotoxicity to animal cells by comprising an indole ring, introducing a cationic monomer thereinto, or comprising NHis as a sub-monomer containing imidazole on a side branch. Therefore, the antimicrobial peptoid of the present inventive concept has improved selectivity to bacteria and thus can be advantageously used for an antimicrobial composition.

3 Claims, 45 Drawing Sheets

ANTIMICROBIAL PEPTOID HAVING IMPROVED SELECTIVITY AND ANTIMICROBIAL COMPOSITION COMPRISING SAME

TECHNICAL FIELD

The present inventive concept relates to an antimicrobial peptoid, and more particularly, to an antimicrobial peptoid which has high antimicrobial activity and reduced toxicity to animal cells.

BACKGROUND ART

In 1928, Alexander Fleming (the Nobel Prize in Physiology or Medicine, 1945) discovered penicillin in the green mold (*Penicillium rubens*), and since penicillin has been used as a miracle antibiotic from 1942, the mortality caused by pathogenic bacterial infections in humans has dramatically reduced. Afterward, various types of antibiotics such as sulfa drugs, tetracyclines, quinolones, aminoglycosides, vancomycin, rifamycins, daptomycin, and carbapenems have been developed to treat various bacterial infections. However, because of the abuse of antibiotics in hospitals or livestock farms and the neglect of the development of new antibiotic drugs by pharmaceutical companies over the past 30 years, the number of patients infected with antibiotic-resistant bacteria that cannot be treated with any existing antibiotics (pan-resistant bacteria) has increased.

Multidrug-resistant bacteria (MDR), also called super bacteria, refer to bacteria that have acquired resistance to multiple antibiotics simultaneously through natural selection or mutation. The major pathogens that cause a problem with antibiotic resistance are so-called 'ESKAPE' strains, including *Enterococcus, Staphylococcus aureus, Klebsiella pneumoniae, Acinetobacter baumannii, Pseudomonas aeruginosa*, and *Enterobacter*. The increase in multidrug-resistant bacteria having resistance to various antibiotics has become a global problem that threatens human health in the $21^{st}$ century, and no new treatment is being developed, which is a serious problem. Therefore, there is an urgent need for development of antibiotics to treat bacteria with multi-drug resistance and differentiated antimicrobial mechanisms.

Antimicrobial peptides (AMPs) are, as part of the innate defense system in most organisms, small-sized peptides consisting of 10 to 50 amino acids, and natural materials acting as primary defense materials when an organism is infected by a pathogen. The antimicrobial peptides have excellent antimicrobial activity even against bacteria resistant to existing antibiotics, and are attracting attention as a next-generation therapeutic agent that can address the problem of antibiotic resistance.

Antimicrobial peptoids structurally mimicking antimicrobial peptides are promising antimicrobial agents compensating for the limitation of antimicrobial peptides. Peptoids are artificially-synthesized peptidomimetics, and have a backbone in which tertiary amides in which a substituent is attached to an amine are repeated, that is, a structure in the form of an oligomer of N-alkylated glycine. Such peptoids have very excellent stability in the body due to high resistance to a protease unlike a peptide, and are able to be simply synthesized by solid-phase synthesis. Accordingly, antimicrobial peptoids may more stably exhibit antimicrobial activity than natural antimicrobial peptides as in vivo hydrolysis by an enzyme is delayed. However, antimicrobial peptoids have a disadvantage of showing cytotoxicity against mammalian cells such as NIH 3T3 mouse fibroblasts. Accordingly, there is a need for research on antimicrobial peptoids with reduced toxicity to animal cells and increased selectivity.

DISCLOSURE

Technical Problem

The present inventive concept is directed to providing an The term "peptoid" used herein, which exhibits antimicrobial activity against bacteria and low cytotoxicity, and an antimicrobial composition including the same.

The present inventive concept is also directed to providing a method of preparing an antimicrobial composition, which includes the above-described antimicrobial peptoid.

The technical objects of the present inventive concept are not limited to the technical objects mentioned above, and other technical objects not mentioned herein will be clearly understood by those of ordinary skill in the art from the following description.

Technical Solution

To achieve the technical objects described above, the present inventive concept may provide an antimicrobial peptoid represented by Formula 1 below.

$$H—X_1—Y_1—Z_1—X_2—Y_2—Z_2—X_3—Y_3—Z_3—X_4—Y_4—Z_4—NH_2 \quad \text{[Formula 1]}$$

wherein $X_1$ to $Z_1$, $X_2$ to $Z_2$, $X_3$ to $Z_3$, and $X_4$ to $Z_4$ are each independently Nspe, NLys, NhTrp, NHis, Npm, or N4hb.

Specifically, the antimicrobial peptoid may be any one or more selected from Formulas 2 to 5 below.

$$\text{H-NLys-Nspe-Nspe-NLys-Nspe-Nspe-NLys-NLys-Nspe-NLys-NhTrp-NhTrp-}NH_2; \quad \text{[Formula 2]}$$

$$\text{H-NLys-NhTrp-NhTrp-NLys-Nspe-Nspe-NLys-Nspe-Nspe-NLys-NLys-Nspe-}NH_2; \quad \text{[Formula 3]}$$

$$\text{H-NLys-NhTrp-NhTrp-NHis-Nspe-Nspe-NLys-Nspe-Nspe-NLys-NLys-Nspe-}NH_2; \text{ and} \quad \text{[Formula 4]}$$

$$\text{H-NLys-Nspe-Nspe-NLys-Nspe-Nspe-NLys-NHis-Nspe-NLys-NhTrp-NhTrp-}NH_2. \quad \text{[Formula 5]}$$

In addition, the present inventive concept for achieving the above-described technical objects may provide an antimicrobial composition which contains any one or more of the above-described antimicrobial peptoids as an active ingredient.

The antimicrobial peptoid may exhibit antimicrobial activity against gram-positive or gram-negative bacteria.

The gram-positive bacteria may be bacteria of *Staphylococcus* sp., *Bacillus* sp., *Streptococcus* sp., or *Enterococcus* sp.

The gram-positive bacteria may be *Staphylococcus aureus*, methicillin-resistant *Staphylococcus aureus* (MRSA), Quinolone-resistant *Staphylococcus aureus* (QRSA), vancomycin-resistant *enterococcus* (VRE), vancomycin intermediate-resistant *Staphylococcus aureus* (VISA), *Bacillus subtilis, Bacillus cereus, Streptococcus pneumoniae, Enterococcus faecalis, Enterococcus faecium*, or *Staphylococcus epidermidis.*

The gram-negative bacteria may be bacteria of *Salmonella* sp., *Acinetobacter* sp., *Escherichia* sp., *Pseudomonas* sp., *Enterobacter* sp., or *Klebsiella* sp.

The gram-negative bacteria may be *Salmonella typhimurium, Acinetobacter calcoaceticus, Acinetobacter bauman-*

*nii*, *Escherichia coli*, *Pseudomonas aeruginosa*, *Klebsiella pneumoniae*, or *Klebsiella aerogenes*.

The present inventive concept for achieving the above-described technical objects may include preparing deprotected polymer resin beads (S100); preparing a bromoacetylate peptoid by adding the deprotected polymer resin beads, bromoacetic acid, diisopropylcarbodiimide (DIC), and an organic solvent and performing a bromoacetylation reaction (S200); adding a submonomer to the bromoacetylate peptoid and performing an amine substitution reaction (S300); obtaining an antimicrobial peptoid having the desired sequence by repeating S200 to S300 (S400);

and separating a polymer resin from the antimicrobial peptoid using a cleavage solution (S500), wherein the submonomer is Nspe, NLys, NhTrp, NHis, Npm, or N4hb.

After S500, a process of performing a counter ion substitution reaction by removing trifluoroacetate (TFA) ions included in the composition using a carbonate ion exchange resin and adding an acidic solution (S600) may be further included. The acidic solution may be acetic acid or hydrochloric acid.

Advantageous Effects

According to the present inventive concept, as an antimicrobial peptoid of the present inventive concept includes an indole ring, introduces a cationic monomer, or includes NHis as a submonomer including imidazole at a side chain, excellent antimicrobial activity against bacteria and low cytotoxicity in animal cells are exhibited. Accordingly, due to improved selectivity, the antimicrobial peptoid of the present inventive concept can be effectively used as an antimicrobial composition.

MODES OF THE INVENTIVE CONCEPT

Figure 1:
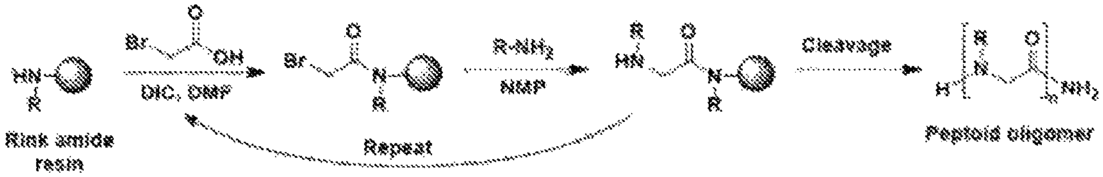
FIG. 1 is a schematic diagram illustrating the process of solid-phase peptoid synthesis (SPPS) for preparing a peptoid of the present inventive concept.

While the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept. To explain each drawing, like numerals denote like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present inventive concept will be described in detail.

Antimicrobial Peptoid

The term "peptoid" used herein, as a structural isomer of a peptide, may refer to a peptide derivative which has a similar monomer sequence but the structure of oligo-N-substituted glycine in which a side chain is attached to nitrogen, not carbon, of the backbone. Since the peptoid has a substituent (R) attached to the nitrogen (N) atom of an amide group, it has a configuration without a chiral center and amide hydrogen, and has the sequence specificity of natural biopolymers, such as a protein, a nucleic acid, etc. Monomers with basic information serve as components to form a precisely defined sequence, having a structure with a specific function through folding or assembly. Since such a peptoid is unnatural unlike a peptide, and is a non-natural biopolymer or biomimetic polymer, it can overcome the disadvantage of peptides being easily degraded in vivo because of high resistance to proteases and very excellent in vivo stability. In addition, since the helical structure of a peptide is maintained by hydrogen bonds, structural transformation occurs at 40 °C or more. However, a peptoid may have thermal and chemical stability in a relatively wide range, such as not only maintaining structural stability even at 70 °C or more, but also maintaining a stable helical structure even with a solution containing a salt or having a low pH.

However, the type of monomer constituting a peptoid and the peptoid sequence may play a pivotal role in determining the peptoid function. As described above, a peptoid has a structure in which an amino acid side chain is attached to the nitrogen of an amide bond. Accordingly, the peptoid backbone has no asymmetry of monomer molecules, and the peptoid amide bond facilitates the conversion between cis-trans amide isomers. In addition, since there is no hydrogen bond formed by the backbone amide-NH, which serves to strongly fix a peptide secondary structure, a peptoid may have a relatively flexible structure than a peptide. Due to the structural characteristics of such a peptoid backbone, it is difficult to form secondary structures such as helical and/or sheet structures by hydrogen bonds. Accordingly, research is being conducted to induce the sequence and structure of a peptoid having various characteristics using monomers with various functional groups and chemical structures, and since a protein and a peptide have different functions depending on the degree of a helical content, it is important to design the peptoid sequence-structure relationship for mimicking with further detailed characterization.

The term "antimicrobial peptoid" used herein may refer to a peptoid having antimicrobial activity, and may also be referred to as a peptoid.

In addition, the antimicrobial peptoid may be easily synthesized using solid-phase synthesis like a peptide. A peptoid having a desired sequence may be obtained by repeating a two-step reaction including a bromoacetylation reaction and an amine substitution reaction several times using polymer beads with an amine group as a starting material.

The antimicrobial peptoid may include at least one or more submonomers selected from Nspe, NLys, NhTrp, NHis, Npm, and N4hb.

The antimicrobial peptoid of the present inventive concept may be formed by mimicking Omiganan, which is a derivative of the natural antimicrobial peptide, indolicidin. The Omiganan is a cationic antimicrobial peptide consisting of 12 amino acids, and may include an amino acid having an indole ring, that is, tryptophan, and/or an analogue thereof. As a peptoid mimic of the Omiganan, the antimicrobial peptoid of the present inventive concept may have an excellent interaction with a membrane interface, and thus may have the characteristic of strong cell membrane disrupting activity.

The antimicrobial peptoid of the present inventive concept may be represented by Formula 1 below.

$$H—X_1—Y_1—Z_1—X_2—Y_2—Z_2—X_3—Y_3—Z_3—X_4—Y_4—Z_4—NH_2 \quad \text{[Formula 1]}$$

wherein $X_1$ to $Z_1$, $X_2$ to $Z_2$, $X_3$ to $Z_3$, and $X_4$ to $Z_4$ are each independently Nspe, NLys, NhTrp, NHis, Npm, or N4hb.

Specifically, the antimicrobial peptoid may be any one or more selected from Peptoids 1 to 81 shown in Tables 1 to 4 below.

TABLE 1

| Classification | Structure |
|---|---|
| Peptoid 1 | H-NLys-Nspe-Nspe-NLys-Nspe-Nspe-NLys-Nspe-Nspe-NLys-Nspe-Nspe-$NH_2$ |
| Peptoid 2 | H-NLys-Npm-Npm-NLys-Npm-Npm-NLys-Npm-Npm-NLys-Npm-Npm-$NH_2$ |
| Peptoid 3 | H-NhTrp-NLys-Nspe-Nspe-NLys-Nspe-Nspe-NLys-Nspe-Nspe-NLys-Nspe-Nspe-$NH_2$ |
| Peptoid 4 | H-NLys-Nspe-Nspe-NLys-Nspe-Nspe-NLys-Nspe-Nspe-NLys-Nspe-Nspe-NhTrp-$NH_2$ |
| Peptoid 5 | H-NhTrp-NLys-Nspe-Nspe-NLys-Nspe-Nspe-NLys-Nspe-Nspe-NLys-Nspe-Nspe-NhTrp-$NH_2$ |
| Peptoid 6 | H-NhTrp-NhTrp-NLys-Nspe-Nspe-NLys-Nspe-Nspe-NLys-Nspe-Nspe-NLys-Nspe-Nspe-$NH_2$ |
| Peptoid 7 | H-NLys-Nspe-Nspe-NLys-Nspe-Nspe-NLys-Nspe-Nspe-NLys-Nspe-NhTrp-$NH_2$ |
| Peptoid 8 | H-NLys-Nspe-Nspe-NLys-Nspe-Nspe-NLys-Nspe-NhTrp-NLys-Nspe-Nspe-$NH_2$ |
| Peptoid 9 | H-NLys-Nspe-Nspe-NLys-Nspe-NhTrp-NLys-Nspe-Nspe-NLys-Nspe-Nspe-$NH_2$ |
| Peptoid 10 | H-NLys-Nspe-NhTrp-NLys-Nspe-Nspe-NLys-Nspe-Nspe-NLys-Nspe-Nspe-$NH_2$ |
| Peptoid 11 | H-NLys-Nspe-Nspe-NLys-Nspe-Nspe-NLys-Nspe-Nspe-NLys-NhTrp-NhTrp-$NH_2$ |
| Peptoid 12 | H-NLys-Nspe-Nspe-NLys-Nspe-Nspe-NLys-NhTrp-NhTrp-NLys-Nspe-Nspe-$NH_2$ |
| Peptoid 13 | H-NLys-Nspe-Nspe-NLys-NhTrp-NhTrp-NLys-Nspe-Nspe-NLys-Nspe-Nspe-$NH_2$ |
| Peptoid 14 | H-NLys-NhTrp-NhTrp-NLys-Nspe-Nspe-NLys-Nspe-Nspe-NLys-Nspe-Nspe-$NH_2$ |
| Peptoid 15 | H-NLys-Nspe-Nspe-NLys-Nspe-NhTrp-NLys-NhTrp-Nspe-NLys-Nspe-Nspe-$NH_2$ |
| Peptoid 16 | H-NLys-Nspe-NhTrp-NLys-Nspe-Nspe-NLys-Nspe-Nspe-NLys-Nspe-NhTrp-$NH_2$ |
| Peptoid 17 | H-NLys-NhTrp-Nspe-NLys-Nspe-Nspe-NLys-Nspe-Nspe-NLys-Nspe-NhTrp-$NH_2$ |
| Peptoid 18 | H-Nlys-NhTrp-NhTrp-NLys-Nspe-Nspe-NLys-Nspe-Nspe-NLys-NhTrp-NhTrp-$NH_2$ |
| Peptoid 19 | H-NLys-Nspe-Nspe-NLys-Nspe-Nspe-NLys-NhTrp-NhTrp-NLys-NhTrp-NhTrp-$NH_2$ |
| Peptoid 20 | H-NLys-Nspe-Nspe-NLys-NhTrp-NhTrp-NLys-NhTrp-NhTrp-NLys-Nspe-Nspe-$NH_2$ |
| Peptoid 21 | H-NLys-NhTrp-NhTrp-NLys-NhTrp-NhTrp-NLys-Nspe-Nspe-NLys-Nspe-Nspe-$NH_2$ |
| Peptoid 22 | H-NLys-Nspe-NhTrp-NLys-Nspe-NhTrp-NLys-Nspe-NhTrp-NLys-Nspe-NhTrp-$NH_2$ |
| Peptoid 23 | H-Nlys-NhTrp-NhTrp-Nlys-NhTrp-NhTrp-Nlys-NhTrp-NhTrp-Nlys-NhTrp-NhTrp-$NH_2$ |

TABLE 2

| Classification | Structure |
|---|---|
| Peptoid 24 | H-NLys-Nspe-Nspe-NLys-Nspe-NhTrp-NLys-Nspe-Nspe-NLys-NLys-Nspe-$NH_2$ |
| Peptoid 25 | H-NLys-Nspe-Nspe-NLys-Nspe-NhTrp-NLys-NLys-Nspe-NLys-Nspe-Nspe-$NH_2$ |
| Peptoid 26 | H-NLys-Nspe-Nspe-NLys-NLys-NhTrp-NLys-Nspe-Nspe-NLys-Nspe-Nspe-$NH_2$ |
| Peptoid 27 | H-NLys-NLys-Nspe-NLys-Nspe-NhTrp-NLys-Nspe-Nspe-NLys-Nspe-Nspe-$NH_2$ |
| Peptoid 28 | H-NLys-Nspe-Nspe-NLys-Nspe-Nspe-NLys-Nspe-NLys-NLys-NhTrp-NhTrp-$NH_2$ |
| Peptoid 29 | H-NLys-Nspe-Nspe-NLys-Nspe-Nspe-NLys-NLys-Nspe-NLys-NhTrp-NhTrp-$NH_2$ |
| Peptoid 30 | H-NLys-Nspe-Nspe-NLys-NLys-Nspe-NLys-Nspe-Nspe-NLys-NhTrp-NhTrp-$NH_2$ |
| Peptoid 31 | H-NLys-NLys-Nspe-NLys-Nspe-Nspe-NLys-Nspe-Nspe-NLys-NhTrp-NhTrp-$NH_2$ |
| Peptoid 32 | H-NLys-NhTrp-NhTrp-NLys-Nspe-Nspe-NLys-Nspe-Nspe-NLys-NLys-Nspe-$NH_2$ |
| Peptoid 33 | H-NLys-NhTrp-NhTrp-NLys-Nspe-Nspe-NLys-NLys-Nspe-NLys-Nspe-Nspe-$NH_2$ |
| Peptoid 34 | H-NLys-NhTrp-NhTrp-NLys-NLys-Nspe-NLys-Nspe-Nspe-NLys-Nspe-Nspe-$NH_2$ |
| Peptoid 35 | H-NhTrp-NhTrp-NLys-Nspe-Nspe-NLys-Nspe-Nspe-NLys-NLys-Nspe-NLys-Nspe-Nspe-$NH_2$ |
| Peptoid 36 | H-NhTrp-NhTrp-NLys-NLys-Nspe-NLys-Nspe-Nspe-NLys-Nspe-Nspe-NLys-Nspe-Nspe-$NH_2$ |
| Peptoid 37 | H-NhTrp-NhTrp-NLys-Nspe-Nspe-NLys-Nspe-Nspe-NLys-Nspe-Nspe-NLys-$NH_2$ |
| Peptoid 38 | H-NhTrp-NhTrp-NLys-Nspe-NLys-NLys-Nspe-Nspe-NLys-Nspe-Nspe-NLys-$NH_2$ |
| Peptoid 39 | H-NLys-Nspe-Nspe-NLys-Nspe-Nspe-NLys-NLys-Npm-NLys-NhTrp-NhTrp-$NH_2$ |
| Peptoid 40 | H-NLys-Nspe-Nspe-NLys-Npm-Npm-NLys-NLys-Nspe-NLys-NhTrp-NhTrp-$NH_2$ |

TABLE 2-continued

| Classification | Structure |
|---|---|
| Peptoid 41 | H-NLys-Npm-Npm-NLys-Nspe-Nspe-NLys-NLys-Nspe-NLys-NhTrp-NhTrp-$NH_2$ |
| Peptoid 42 | H-Npm-NLys-Nspe-Nspe-NLys-Nspe-Nspe-NLys-Nspe-Nspe-NLys-Nspe-Nspe-Npm-$NH_2$ |
| Peptoid 43 | H-Npm-Npm-NLys-Nspe-Nspe-NLys-Nspe-Nspe-NLys-Nspe-Nspe-NLys-Nspe-Nspe-$NH_2$ |
| Peptoid 44 | H-NLys-Nspe-Nspe-NLys-Nspe-Nspe-NLys-Nspe-Nspe-NLys-Npm-Npm-$NH_2$ |
| Peptoid 45 | H-NLys-Nspe-Nspe-NLys-Nspe-Nspe-NLys-NLys-Nspe-NLys-Npm-Npm-$NH_2$ |
| Peptoid 46 | H-NLys-Npm-Npm-NLys-Nspe-Nspe-NLys-Nspe-Nspe-NLys-Nspe-Nspe-$NH_2$ |
| Peptoid 47 | H-NLys-Npm-Npm-NLys-Nspe-Nspe-NLys-Nspe-Nspe-NLys-NLys-Nspe-$NH_2$ |
| Peptoid 48 | H-Nspe-NLys-Nspe-Nspe-NLys-Nspe-Nspe-NLys-Nspe-Nspe-NLys-Nspe-$NH_2$ |

TABLE 3

| Classification | Structure |
|---|---|
| Peptoid 49 | H-NLys-Nspe-Nspe-NLys-Nspe-Nspe-NLys-Nspe-Nspe-NLys-NLys-$NH_2$ |
| Peptoid 50 | H-NLys-Nspe-Nspe-NLys-Nspe-Nspe-NLys-NLys-Nspe-NLys-Nspe-$NH_2$ |
| Peptoid 51 | H-NLys-Nspe-Nspe-NLys-NLys-Nspe-NLys-Nspe-Nspe-NLys-Nspe-$NH_2$ |
| Peptoid 52 | H-NLys-NLys-Nspe-NLys-Nspe-Nspe-NLys-Nspe-Nspe-NLys-Nspe-$NH_2$ |
| Peptoid 53 | H-Nspe-NLys-Nspe-Nspe-NLys-Nspe-Nspe-NLys-Nspe-Nspe-NLys-NLys-$NH_2$ |
| Peptoid 54 | H-Nspe-NLys-Nspe-Nspe-NLys-Nspe-Nspe-NLys-NLys-Nspe-NLys-Nspe-$NH_2$ |
| Peptoid 55 | H-Nspe-NLys-Nspe-Nspe-NLys-NLys-Nspe-NLys-Nspe-Nspe-NLys-Nspe-$NH_2$ |
| Peptoid 56 | H-Nspe-NLys-NLys-Nspe-NLys-Nspe-Nspe-NLys-Nspe-Nspe-NLys-Nspe-$NH_2$ |
| Peptoid 57 | H-NhTrp-NLys-Nspe-Nspe-NLys-Nspe-Nspe-NLys-Nspe-Nspe-NLys-NLys-$NH_2$ |
| Peptoid 58 | H-NhTrp-NLys-Nspe-Nspe-NLys-Nspe-Nspe-NLys-NLys-Nspe-NLys-Nspe-$NH_2$ |
| Peptoid 59 | H-NhTrp-NLys-Nspe-Nspe-NLys-NLys-Nspe-NLys-Nspe-Nspe-NLys-Nspe-$NH_2$ |
| Peptoid 60 | H-NhTrp-NLys-NLys-Nspe-NLys-Nspe-Nspe-NLys-Nspe-Nspe-NLys-Nspe-$NH_2$ |
| Peptoid 61 | H-NhTrp-Nspe-NLys-Nspe-Nspe-NLys-Nspe-Nspe-NLys-Nspe-Nspe-NLys-NLys-$NH_2$ |
| Peptoid 62 | H-NhTrp-Nspe-NLys-Nspe-Nspe-NLys-Nspe-Nspe-NLys-NLys-Nspe-NLys-Nspe-$NH_2$ |
| Peptoid 63 | H-NhTrp-Nspe-NLys-Nspe-Nspe-NLys-NLys-Nspe-NLys-Nspe-Nspe-NLys-Nspe-$NH_2$ |
| Peptoid 64 | H-NhTrp-Nspe-NLys-NLys-Nspe-NLys-Nspe-Nspe-NLys-Nspe-Nspe-NLys-Nspe-$NH_2$ |
| Peptoid 65 | H-N4hb-NhTrp-NhTrp-N4hb-NhTrp-NhTrp-N4hb-NhTrp-NhTrp-N4hb-NhTrp-NhTrp-$NH_2$ |
| Peptoid 66 | H-N4hb-Nspe-Nspe-N4hb-Nspe-Nspe-N4hb-N4hb-Nspe-N4hb-NhTrp-NhTrp-$NH_2$ |

TABLE 4

| Classification | Structure |
|---|---|
| Peptoid 67 | H-NLys-NhTrp-NhTrp-NLys-NHis-Nspe-NLys-Nspe-Nspe-NLys-NLys-Nspe-$NH_2$ |
| Peptoid 68 | H-NLys-NhTrp-NhTrp-NLys-Nspe-NHis-NLys-Nspe-Nspe-NLys-NLys-Nspe-$NH_2$ |
| Peptoid 69 | H-NLys-NhTrp-NhTrp-NLys-Nspe-Nspe-NLys-NHis-Nspe-NLys-NLys-Nspe-$NH_2$ |
| Peptoid 70 | H-NLys-NhTrp-NhTrp-NLys-Nspe-Nspe-NLys-Nspe-NHis-NLys-NLys-Nspe-$NH_2$ |
| Peptoid 71 | H-NLys-NhTrp-NhTrp-NLys-Nspe-Nspe-NLys-Nspe-Nspe-NLys-NLys-NHis-$NH_2$ |
| Peptoid 72 | H-NHis-NhTrp-NhTrp-NLys-Nspe-Nspe-NLys-Nspe-Nspe-NLys-NLys-Nspe-$NH_2$ |
| Peptoid 73 | H-NLys-NhTrp-NhTrp-NHis-Nspe-Nspe-NLys-Nspe-Nspe-NLys-NLys-Nspe-$NH_2$ |
| Peptoid 74 | H-NLys-NhTrp-NhTrp-NLys-Nspe-Nspe-NHis-Nspe-Nspe-NLys-NLys-Nspe-$NH_2$ |
| Peptoid 75 | H-NLys-NhTrp-NhTrp-NLys-Nspe-Nspe-NLys-Nspe-Nspe-NHis-NLys-Nspe-$NH_2$ |
| Peptoid 76 | H-NLys-NhTrp-NhTrp-NLys-Nspe-Nspe-NLys-Nspe-Nspe-NLys-NHis-Nspe-$NH_2$ |
| Peptoid 77 | H-NLys-Nspe-Nspe-NLys-Nspe-Nspe-NLys-NLys-Nspe-NHis-NhTrp-NhTrp-$NH_2$ |
| Peptoid 78 | H-NLys-Nspe-Nspe-NLys-Nspe-Nspe-NLys-NHis-Nspe-NLys-NhTrp-NhTrp-$NH_2$ |
| Peptoid 79 | H-NLys-Nspe-Nspe-NLys-Nspe-Nspe-NHis-NLys-Nspe-NLys-NhTrp-NhTrp-$NH_2$ |
| Peptoid 80 | H-NLys-Nspe-Nspe-NHis-Nspe-Nspe-NLys-NLys-Nspe-NLys-NhTrp-NhTrp-$NH_2$ |
| Peptoid 81 | H-NHis-Nspe-Nspe-NLys-Nspe-Nspe-NLys-NLys-Nspe-NLys-NhTrp-NhTrp-$NH_2$ |

More specifically, the antimicrobial peptoid may be any one or more selected from Formulas 2 to 5 below.

H-NLys-Nspe-Nspe-NLys-Nspe-Nspe-NLys-NLys-Nspe-NLys-NhTrp-NhTrp-$NH_2$; [Formula 2]

H-NLys-NhTrp-NhTrp-NLys-Nspe-Nspe-NLys-Nspe-Nspe-NLys-NLys-Nspe-$NH_2$; [Formula 3]

H-NLys-NhTrp-NhTrp-NHis-Nspe-Nspe-NLys-Nspe-Nspe-NLys-NLys-Nspe-$NH_2$; and [Formula 4]

H-NLys-Nspe-Nspe-NLys-Nspe-Nspe-NLys-NHis-Nspe-NLys-NhTrp-NhTrp-$NH_2$. [Formula 5]

The term "Nspe" used herein refers to (S)-N-(1-phenylethyl)glycine. The Nspe may be a hydrophobic monomer and have the structure of Formula 6 below.

[Formula 6]

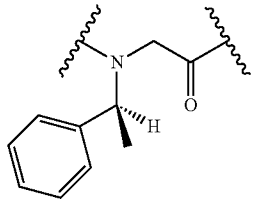

Nspe

The term "NLys" used herein refers to N-(4-aminobutyl) glycine. The NLys may have the structure of Formula 7 below, and may exhibit cationicity when dissolved in a solvent.

[Formula 7]

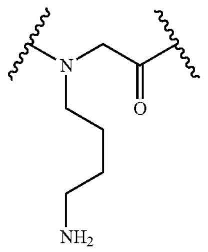

NLys

The term "NhTrp" used herein refers to N-[2-(1H-indol-3-yl)ethyl]glycine. The NhTrp is a monomer having an indole ring, and may have the structure of Formula 8 below.

[Formula 8]

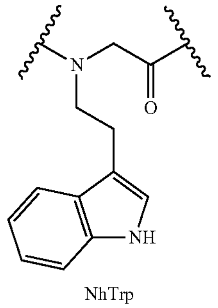

NhTrp

The term "NHis" used herein refers to N-[2-(1H-imidazol-4-yl)ethyl]glycine. The NHis is a monomer having an imidazole ring, and may have the structure of Formula 9 below.

[Formula 9]

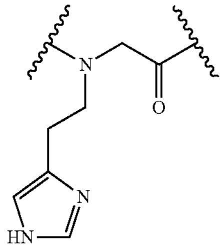

NHis

The term "Npm" used herein refers to N-(phenylmethyl) glycine. The Npm may have the structure of Formula 10 below.

[Formula 10]

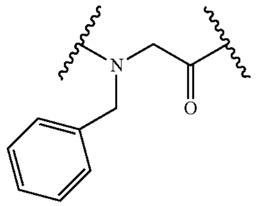

Npm

The term "N4hb" used herein refers to N-(4-hydroxybutyl)glycine. The N4hb may have the structure of Formula 11 below.

[Formula 11]

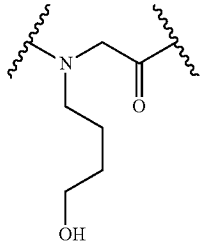

N4hb

The term "antimicrobial activity" used herein refers to the ability to resist bacteria, and all mechanisms performed to defend against the action of microorganisms such as bacteria, fungi, yeast, etc.

The term "gram-positive bacteria" used herein refers to bacteria appearing to be violet as a result of staining with crystal violet. Approximately 80% to 90% of the cell wall of the gram-positive bacteria may consist of peptidoglycan, which forms a thick layer to maintain the size and shape of the cell wall and make the cell wall hard. The gram-positive bacteria may be bacteria of *Staphylococcus* sp., *Bacillus* sp., *Streptococcus* sp., or *Enterococcus* sp, but the present inventive concept is not limited thereto.

For example, the gram-positive bacteria may be *Staphylococcus aureus*, methicillin-resistant *Staphylococcus aureus* (MRSA), Quinolone-resistant *Staphylococcus aureus* (QRSA), vancomycin-resistant *enterococcus* (VRE), vancomycin intermediate-resistant *Staphylococcus aureus* (VISA), *Bacillus subtilis, Bacillus cereus, Streptococcus*

*pneumoniae, Enterococcus faecalis, Enterococcus faecium*, or *Staphylococcus epidermidis*.

The term "gram-negative bacteria" used herein refers to bacteria which are not stained with crystal violet after staining with crystal violet, appearing to be purple as a result of decolorized by ethanol washing.

The gram-negative bacteria may be bacteria of *Salmonella* sp., *Acinetobacter* sp., *Escherichia* sp., *Pseudomonas* sp., *Enterobacter* sp., or *Klebsiella* sp.

For example, the gram-negative bacteria may be *Salmonella typhimurium, Acinetobacter calcoaceticus, Acinetobacter baumannii, Escherichia coli, Pseudomonas aeruginosa, Klebsiella pneumoniae*, or *Klebsiella aerogenes*.

The present inventive concept may provide an antimicrobial composition, which includes at least one or more of the above-described antimicrobial peptoids as an active ingredient.

The antimicrobial peptoid may exhibit antimicrobial activity against gram-positive bacteria or gram-negative bacteria.

The antimicrobial peptoid of the present inventive concept may include a monomer having an indole ring and a cationic monomer in order to solve the cytotoxic problem of a conventional peptoid.

The antimicrobial composition of the present inventive concept may include a peptoid obtained by performing a counter ion-substitution reaction on trifluoroacetic acid (TFA) ions present in a compound. The counter ion substitution may be substitution of the TFA ions with chlorine ions or acetate ions. In other words, the synthesized peptoid compound may include TFA ions upon HPLC analysis or deprotecting group removal. Here, counter ion substitution which removes TFA ions remaining in the peptoid compound and also binds chlorine ions or acetate ions may be performed.

Hereinafter, the present inventive concept will be described in further detail with reference to the following examples. However, the following examples are merely provided to exemplify the present inventive concept, and the scope of the present inventive concept is not limited thereto.

I. Confirmation of Change in Peptoid Activity According to Substitution Number and Position of NhTrp 1. Preparation of Peptoid Submonomer

Preparation Example 1: Preparation of N-[2-(1H-indol-3-yl)ethyl]glycine (NhTrp) submonomer As a peptoid submonomer, an NhTrp(Boc) monomer is prepared using tryptamine as a raw material. An M1 monomer is synthesized using tryptamine, an M2 monomer is synthesized using the M1 monomer, and finally, an M3 submonomer of NhTrp(Boc) is synthesized using the M2 monomer. In Scheme 1, the process of synthesizing the M3 peptoid submonomer of NhTrp(Boc) is shown.

[Scheme 1]

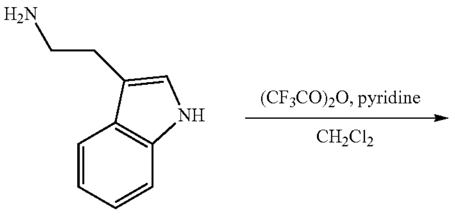

tryptamine

-continued

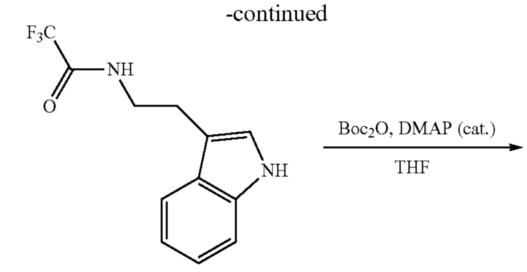

M1

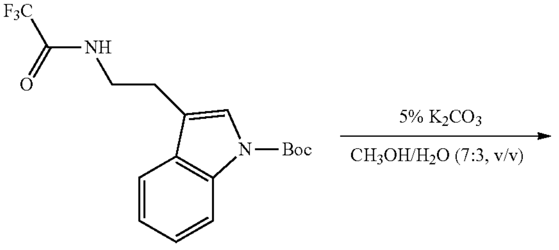

M2

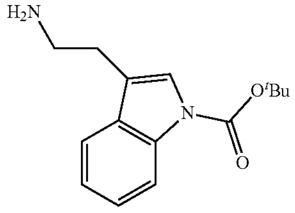

NhTrp(Boc) (M3)

① Preparation of 2,2,2-trifluoro-N-[2-(1H-indol-3-yl)ethyl] acetamide (M1) monomer Trifluoroacetic anhydride (4.5 mL, 32.6 mmol, 1.05 equiv.) is added to a dichloromethane ($CH_2Cl_2$, 280 mL) solution containing pyridine (28 mL, 346 mmol, 11.16 equiv.) and tryptamine (5 g, 31 mmol, 1 equiv.). This is performed in a cold bath at 0 °C in a nitrogen atmosphere. After 5 minutes, the cold bath is removed, and the mixture is stirred at 20 °C for 2 hours. After stirring, the mixture is diluted with dichloromethane ($CH_2Cl_2$), and washed with a saturated sodium bicarbonate aqueous solution ($NaHCO_3$). The product is dried by adding anhydrous sodium sulfate ($Na_2SO_4$) and filtered, followed by concentrating the remaining liquid in vacuo. The residue is used without an additional purification process.

② Preparation of tert-butyl-3-(2-2,2,2-trifluoroacetamido)ethyl)-1H-indole-1-carboxylate (M2) monomer Di-tert-butyl decarbonate (5.2 g, 23.5 mmol, 1.2 equiv.) was added to a tetrahydrofuran (40 mL) solution containing the M1 monomer (5 g, 19.5 mmol, 1 equiv.), and 4-dimethylaminopyridine (DMAP) was added as a catalyst. The solution was heated for 1 hour at 40 °C, diluted with dichloromethane ($CH_2Cl_2$), and washed with water. The product was dried by adding anhydrous sodium sulfate ($Na_2SO_4$) and filtered, followed by concentrating the remaining liquid in vacuo. The residue was purified by chromatography using silica gel, thereby producing a colorless oil.

③ Preparation of tert-butyl-3-(2-aminoethyl)-1H-indole-1-carboxylate (M3, NhTrp) submonomer Potassium carbonate (5.8 g, 42 mmol, 3 equiv.) is added to a mixed solution in which the M2 monomer (4.6 g, 12 mmol, 1 equiv.) is mixed in a solvent prepared by mixing methanol and water in a volume ratio of 7:3. The mixture is stirred for 48 hours, and extract with dichloromethane ($CH_2Cl_2$) after pouring water thereinto. The extract is dried by adding anhydrous sodium sulfate ($Na_2SO_4$) and filtered, and then the remaining liquid is concentrated in vacuo, thereby obtaining an unpurified light-yellow oil. Afterward, when used in synthesis of a peptoid, the obtained product is used without additional purification.

Preparation Example 2: Preparation of N-(tert-butoxycarbonyl)-1,4-butanediamine (NLys(Boc)) Submonomer 1,4-diaminobutane (30.2 mL, 300 mmol, 10 equiv.) is dissolved in a dichloromethane ($CH_2Cl_2$, 1000 mL) solvent and stirred in a 500 mL round-bottom flask. Subsequently, di-tert-butyl-dicarbonate (6.55 g, 30.0 mmol, 1 equiv.) is added to the round-bottom flask containing the above solution for 3 hours. The reaction mixture is stirred overnight, and an unpurified solution is extracted with deionized water. An organic layer is transferred, and the extraction step is repeated twice. The organic layer is dried by adding anhydrous sodium sulfate anhydrous ($Na_2SO_4$), filtered, and dried in vacuo, thereby obtaining an unpurified light-yellow oil. The obtained product is used in the synthesis of a peptoid without additional purification.

Preparation Example 3: Preparation of N-[2-(1H-imidazol-4-yl)ethyl]glycine (NHis) Submonomer As a peptoid submonomer, a NHis(Trt) monomer is prepared using histamine as a raw material. An M1 monomer is synthesized using histamine, an M2 monomer is synthesized using the M1 monomer, and finally, an M3 submonomer of NHis(Trt) is synthesized using the M2 monomer. In the following Scheme 2, the process of synthesizing the M3 submonomer of NHis(Trt) is shown.

[Scheme 2]

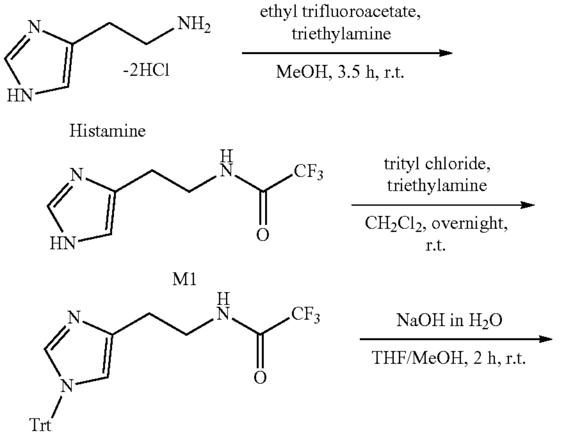

Histamine

M1

M2

-continued

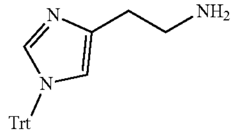

NHis(Trt) (M3)

① Preparation of $N^{\alpha}$-trifluoroacetyl histamine(M1) monomer

Ethyl trifluoroacetate (1.43 mL, 12.0 mmol, 1.2 equiv.) and triethylamine (4.80 mL, 34.0 mmol, 3.4 equiv.) are slowly added to a methanol ($CH_3OH$, 30 mL) solution containing histamine dihydrochloride (1.84 g, 10.0 mmol, 1 equiv.) for 30 minutes. This is performed in a cold bath at 0 °C in a nitrogen atmosphere. After 5 minutes, the cold bath is removed, and the resulting mixture is stirred at 20 °C for 3.5 hours. After stirring, the mixture is diluted with dichloromethane($CH_2Cl_2$), and washed with water. The product is dried by adding anhydrous sodium sulfate ($Na_2SO_4$), and filtered, followed by concentrating the remaining liquid in vacuo. The residue is used without additional purification.

② Preparation of 2,2,2-trifluoro-N-[2-(1-trityl-1H-imidazol-4-yl)ethyl] acetamide(M2) monomer Trityl chloride (3.33 g, 12.0 mmol, 1.2 equiv.) is slowly added to a methanol (30 mL) and dichloromethane (15 mL) solution containing the M1 monomer (2.07 g, 10.0 mmol, 1 equiv.) and triethylamine (4.24 mL, 30 mmol, 3.0 equiv.). The solution is stirred at 20 °C overnight. The resulting solution is diluted with chloroform ($CHCl_3$), and washed twice with water. The product is dried by adding anhydrous sodium sulfate ($Na_2SO_4$), and filtered, followed by concentrating the remaining liquid in vacuo. The residue is purified using hexane.

③ Preparation of 2-(1-trityl-1H-imidazol-4-yl)-ethylamine(M3, NHis(Trt)) submonomer Sodium hydroxide (0.45 g, 11.3 mmol, 5 equiv.) is dissolved in water (5 mL) and added to a mixed solution in which the M2 monomer (1.00 g, 2.5 mmol, 1 equiv.) is mixed in a solvent in which tetrahydrofuran (9 mL) and methanol (12 mL) are mixed in a volume ratio of 3:4. The mixture is stirred for 2 hours, and concentrated in vacuo. Water is poured into the remaining liquid and extraction is performed with chloroform ($CHCl_3$). The organic extract is dried by adding anhydrous sodium sulfate ($Na_2SO_4$) and filtered, and then the remaining liquid is concentrated in vacuo, thereby obtaining an unpurified light-yellow oil. Afterward, when used in the synthesis of a peptoid, the obtained product is used without additional purification.

Preparation Example 4: Preparation of 4-[tris(1-methylethyl)silyl]oxy]-1-butanamine (N4hb(TIPS)) submonomer Triisopropylsilyl chloride (24 mL, 0.12 mol, 1.1 equiv.) dissolved in dichloromethane (50 mL) was added to a cold solution in which 4-aminobutanol (10 g, 0.11 mol, 1 equiv.) and triethylamine (16.5 mL, 0.12 mol) were dissolved in dichloromethane (100 mL). The mixed solution was stirred at room temperature for 20 hours. The resulting suspension was extracted with water (150 mL). A process of extracting an aqueous phase with dichloromethane ($CH_2Cl_2$) was repeated three times. After combining the organic layers, sodium sulfate anhydrous ($Na_2SO_4$) was added for drying, and concentration was performed in vacuo, thereby obtaining a product. The product was used in the synthesis of a peptoid without additional purification.

2. Preparation of Antimicrobial Peptoid

A method of preparing an antimicrobial composition of the present inventive concept may include preparing deprotected polymer resin beads (S100); preparing a bromoacetylate peptoid by adding the deprotected polymer resin beads, bromoacetic acid, diisopropylcarbodiimide (DIC), and an organic solvent and performing a bromoacetylation reaction (S200); adding a submonomer to the bromoacetylate peptoid and performing an amine substitution reaction (S300); obtaining an antimicrobial peptoid having a desired sequence by repeating S200 and S300 (S400); and separating a polymer resin from the antimicrobial peptoid using a cleavage solution (S500).

The antimicrobial peptoid of the present inventive concept may be composed of monomers with various functional groups, that is, the above-described sequences of peptoid submonomer. The submonomer may be at least one selected from NhTrp(Boc), NLys(Boc), N4hb(TIPS), Npm, and Nspe, but the present inventive concept is not limited thereto.

The antimicrobial peptoid of the present inventive concept may be prepared by solid-phase peptoid synthesis (SPPS).

FIG. 1 is a schematic diagram illustrating the process of SPPS for preparing an antimicrobial peptoid of the present inventive concept.

Referring to FIG. 1, a peptoid having a desired sequence may be obtained by repeating a two-step reaction of a bromoacetylation reaction and an amine substitution reaction several times using polymer beads with an amine group as a starting material. As amine submonomers, NhTrp(Boc), NLys(Boc), N4hb(TIPS), Npm, Nspe, and NHis(Trt) (1.0 M, 20 equiv.) were dissolved in an NMP solvent and used.

Example 1: Preparation of Peptoids 1 to 66

Peptoids were synthesized on resin beads using a synthesis method in accordance with a solid-phase submonomer protocol, and synthesized by heating with a microwave. For heating with a microwave, a CEM MARS multimode microwave reaction system (CEM Corp.) was used. As a reaction scale, resin beads (0.065 mmol) were used (0.100 g of resin). First, to remove an Fmoc protecting group from the Fmoc-Rink amide MBHA resin (0.59 mmol/g), treatment with a 20% (v/v) piperidine-containing dimethylformamide (DMF) solution was performed twice at 80 °C. (maximum power: 600 W, ramp 2 min, hold 2 min, stirring level 2). The peptoid sequences were determined by synthesis of a Rink Amide resin. The resin was washed sequentially with dichloromethane ($CH_2Cl_2$) three times, DMF three times, methanol once, DMF three times, and dichloromethane ($CH_2Cl_2$) three times.

Afterward, for a bromoacetylation reaction, bromoacetic acid (1.2 M in DMF, 20 equiv.) and N,N'-diisopropylcarbodiimide (DIC, 20 equiv.) were added to the deprotected resin, stirred and irradiated at 35 °C in a microwave oven (maximum power: 300 W, ramp 30 sec, hold 1 min, stirring level 2), and then the resin was washed in the same manner as the above-described washing sequence.

Subsequently, for an amine substitution reaction, amine submonomers (1.0 M, 20 equiv.) such as NhTrp(Boc), NLys(Boc), N4 hb(TIPS), Npm, and Nspe were used. An amine substitution reaction was carried out by adding the solution containing amine submonomer (1.5 M in N-methylpyrrolidone (NMP), 30~40 equiv.) to a resin-bound bromoacetylate peptoid. The amine substitution reaction was performed in a microwave oven (maximum power: 300 W. 95 °C, ramp 2 min, hold 90 sec, stirring level 2). The bromoacetylation reaction and the amine substitution reaction were repeated until a desired peptoid sequence was obtained.

Afterward, to separate the peptoid from the resin, separation was performed using a cleavage solution (trifluoroacetate (TFA):$CH_2Cl_2$:triisopropylsilane=95:2.5:2.5(v/v/v)) at room temperature for 10 minutes.

The chemical structures of Peptoids 1 to 66 according to Example 1 of the present inventive concept are shown in Tables 5 to 7 below. Peptoids 1 and 2 are known peptoids, which are prepared to compare antimicrobial activity and cytotoxicity with the novel peptoids.

TABLE 5

| Classification | Chemical Structure |
|---|---|
| Peptoid 1 | 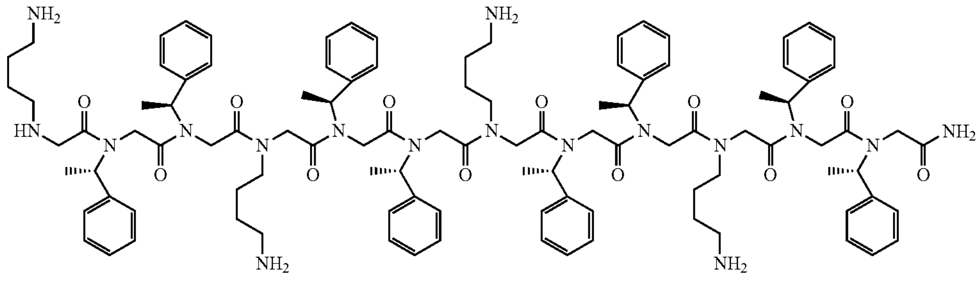 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] |

TABLE 5-continued
| Classification | Chemical Structure |
|---|---|
| Peptoid 2 | 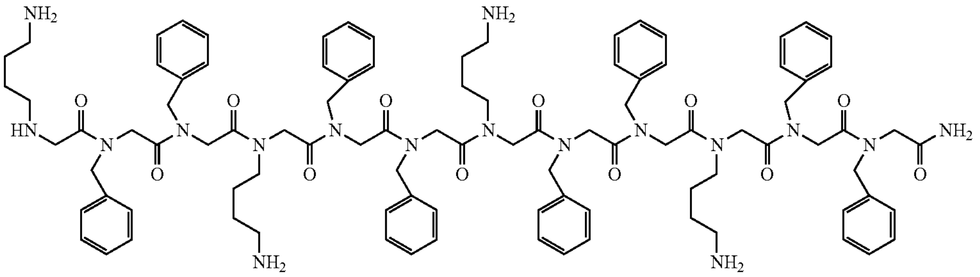 [SMILES: NCCCCNCC(=O)N(CC(=O)N(CC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(N)=O)Cc1ccccc1)Cc1ccccc1)Cc1ccccc1)Cc1ccccc1)Cc1ccccc1)Cc1ccccc1)Cc1ccccc1)Cc1ccccc1]<br>2 |
| Peptoid 3 | 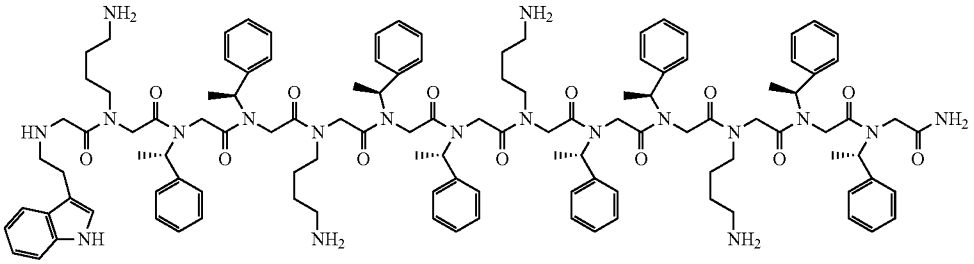 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(C(=O)CN(CCCCN)C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1]<br>3 |
| Peptoid 4 | 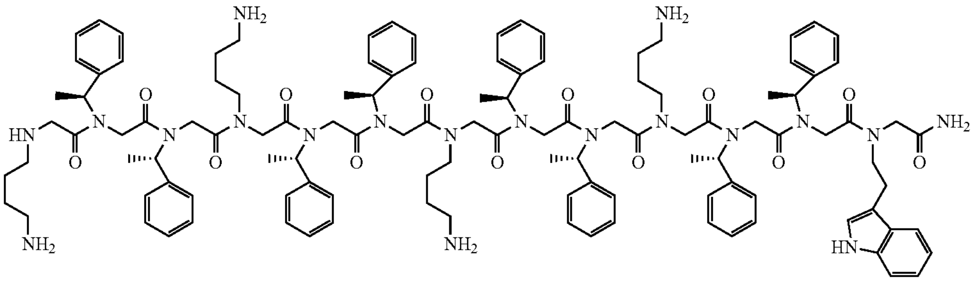 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(=O)N(CCc1c[nH]c2ccccc12)CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)C(=O)CN(C(=O)CNCCCCN)[C@@H](C)c1ccccc1]<br>4 |
| Peptoid 5 | 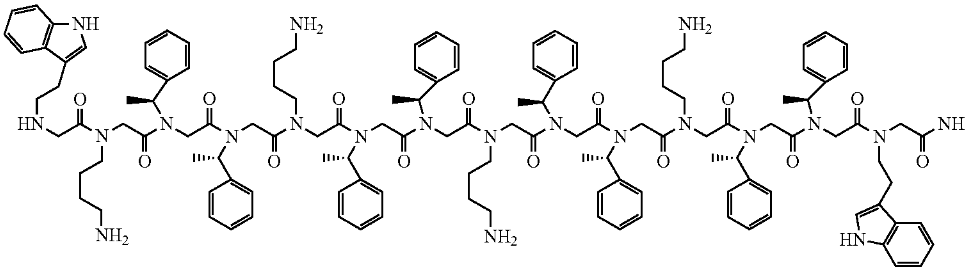 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(=O)N(CCc1c[nH]c2ccccc12)CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)C(=O)CN(C(=O)CN(CCCCN)C(=O)CNCCc1c[nH]c2ccccc12)[C@@H](C)c1ccccc1]<br>5 |
| Peptoid 6 | 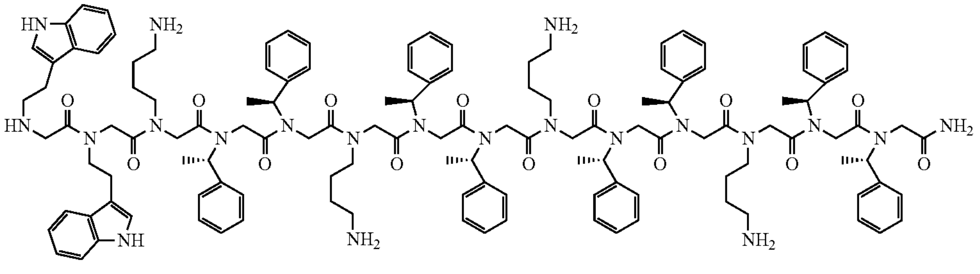 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1]<br>6 |

TABLE 5-continued
| Classification | Chemical Structure |
| --- | --- |
| Peptoid 7 | 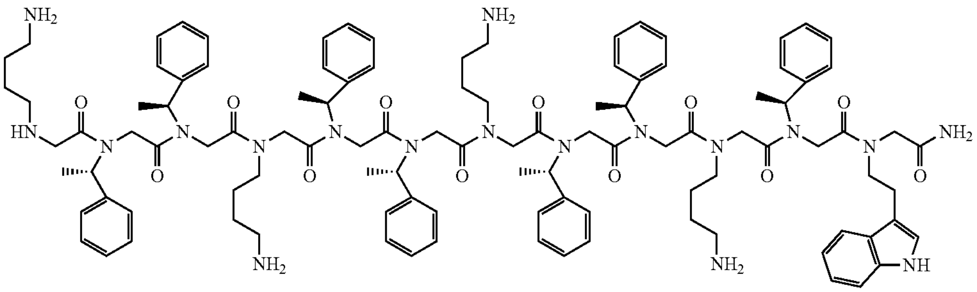 [SMILES: C[C@@H](c1ccccc1)N(CC(=O)N(CCc1c[nH]c2ccccc12)CC(N)=O)C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 7 |
| Peptoid 8 | 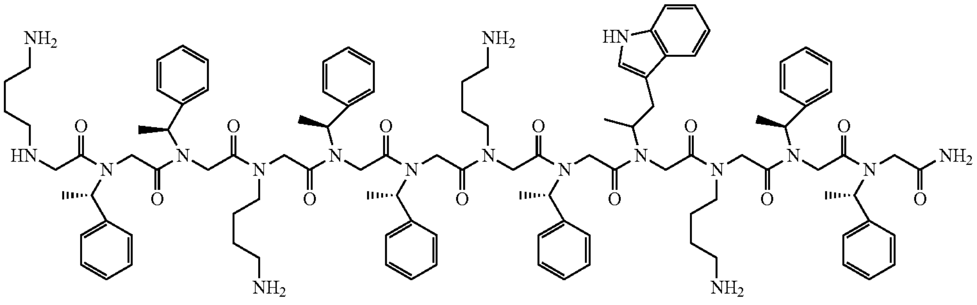 [SMILES: CC(Cc1c[nH]c2ccccc12)N(CC(=O)N(CCCCN)CC(=O)N(CC(=O)N(CC(N)=O)[C@@H](C)c1ccccc1)[C@@H](C)c1ccccc1)C(=O)CN(C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 8 |
| Peptoid 9 | 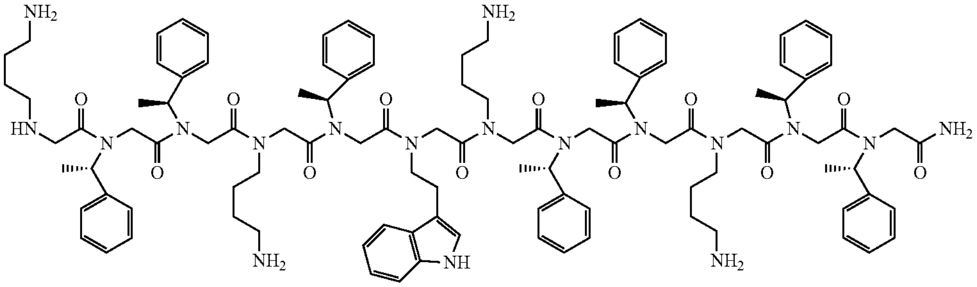 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(CCc1c[nH]c2ccccc12)C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 9 |
| Peptoid 10 | 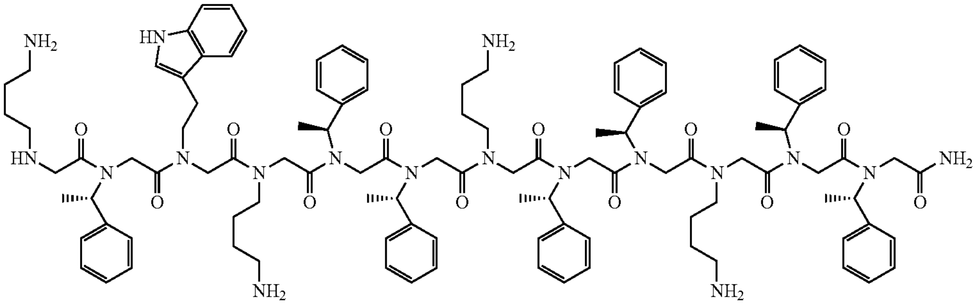 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 10 |

TABLE 5-continued
| Classification | Chemical Structure |
| --- | --- |
| Peptoid 11 | 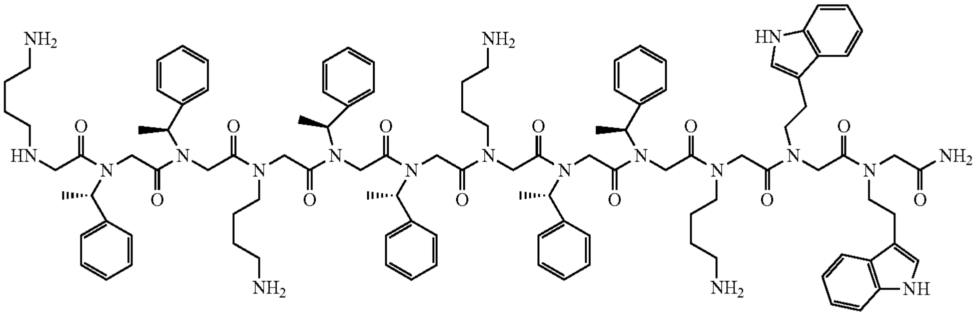 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CCc1c[nH]c2ccccc12)CC(=O)N(CCc1c[nH]c2ccccc12)CC(N)=O)[C@@H](C)c1ccccc1)[C@@H](C)c1ccccc1)[C@@H](C)c1ccccc1)[C@@H](C)c1ccccc1)C(=O)CN(C(=O)CNCCCCN)[C@@H](C)c1ccccc1] 11 |
| Peptoid 12 | 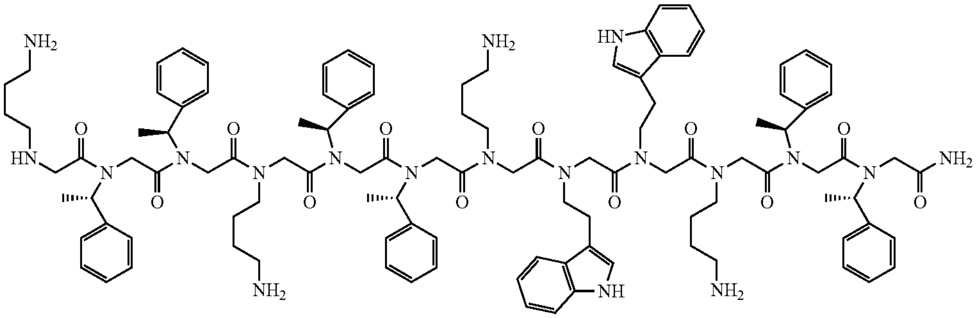 [SMILES: C[C@@H](c1ccccc1)N(CC(N)=O)C(=O)CN(C(=O)CN(CCCCN)C(=O)CN(CCc1c[nH]c2ccccc12)C(=O)CN(CCc1c[nH]c2ccccc12)C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 12 |
| Peptoid 13 | 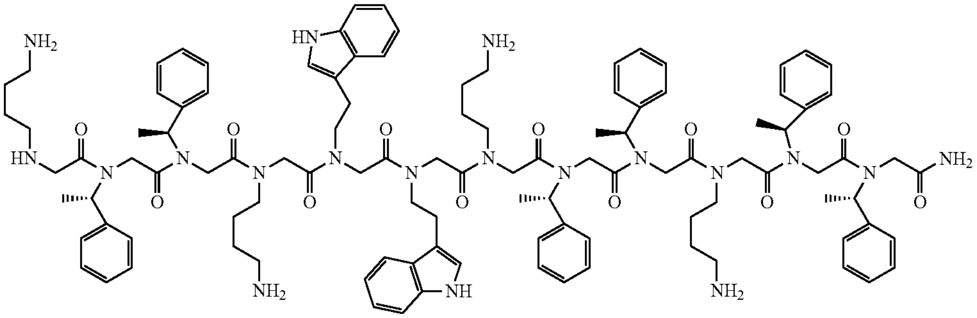 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 13 |
| Peptoid 14 | 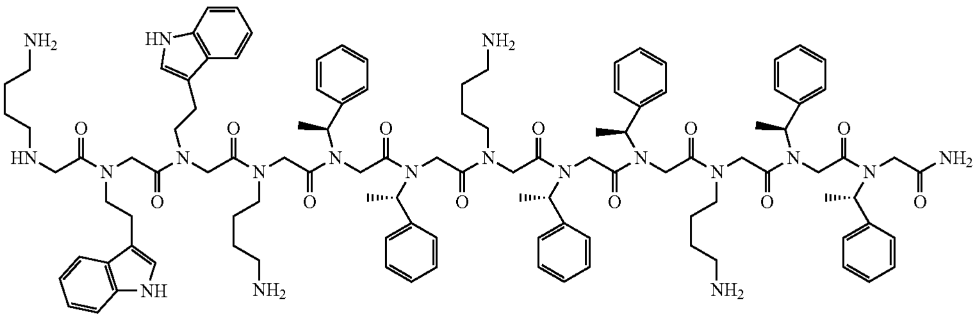 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 14 |

TABLE 5-continued
| Classification | Chemical Structure |
| --- | --- |
| Peptoid 15 | 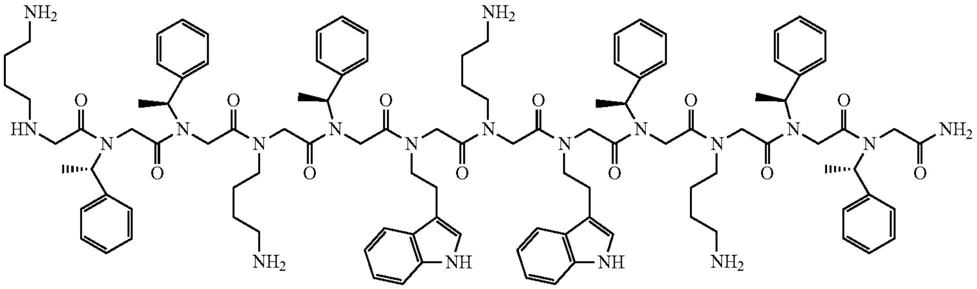 [SMILES: C[C@@H](c1ccccc1)N(CC(N)=O)C(=O)CN(C(=O)CN(CCCCN)C(=O)CN(C(=O)CN(CCc1c[nH]c2ccccc12)C(=O)CN(CCCCN)C(=O)CN(CCc1c[nH]c2ccccc12)C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 15 |
| Peptoid 16 | 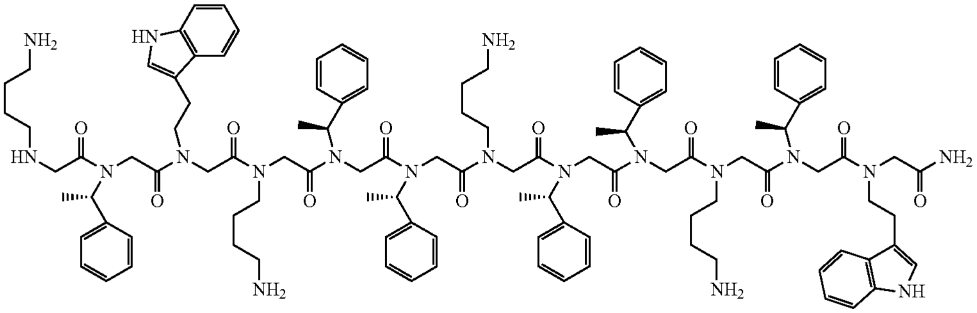 [SMILES: C[C@@H](c1ccccc1)N(CC(=O)N(CCc1c[nH]c2ccccc12)CC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CCc1c[nH]c2ccccc12)CC(N)=O)[C@@H](C)c1ccccc1)[C@@H](C)c1ccccc1)[C@@H](C)c1ccccc1)[C@@H](C)c1ccccc1)[C@@H](C)c1ccccc1)C(=O)CNCCCCN] 16 |
| Peptoid 17 | 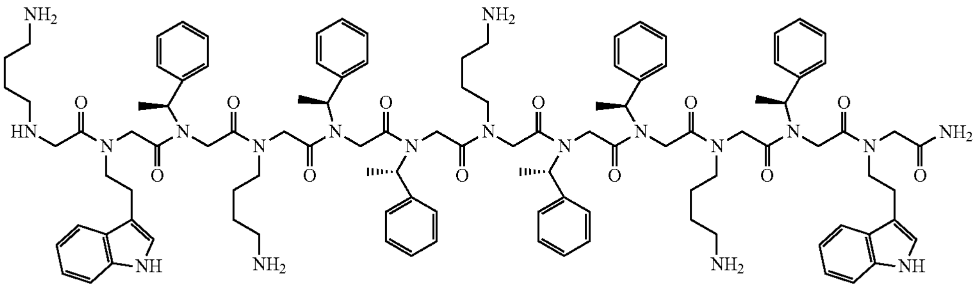 17 |
| Peptoid 18 | 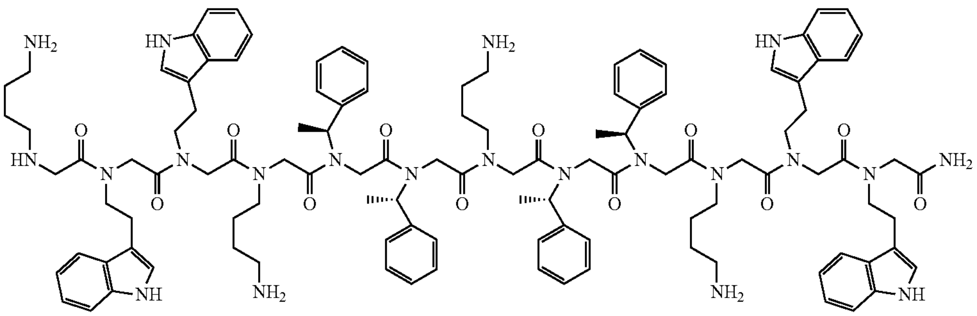 18 |

TABLE 5-continued
| Classification | Chemical Structure |
| --- | --- |
| Peptoid 19 | 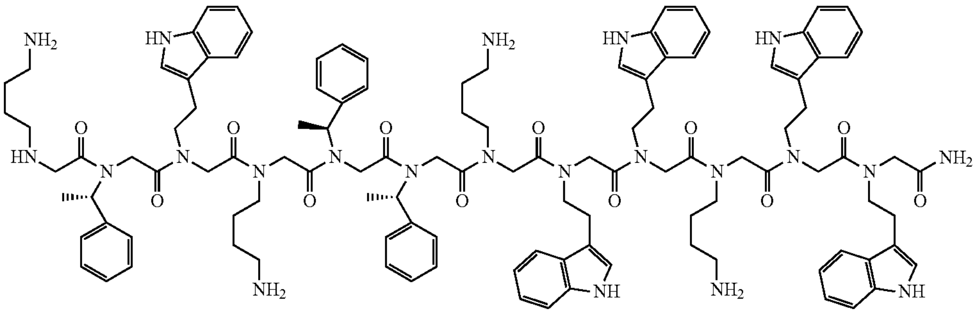 19 |
| Peptoid 20 | 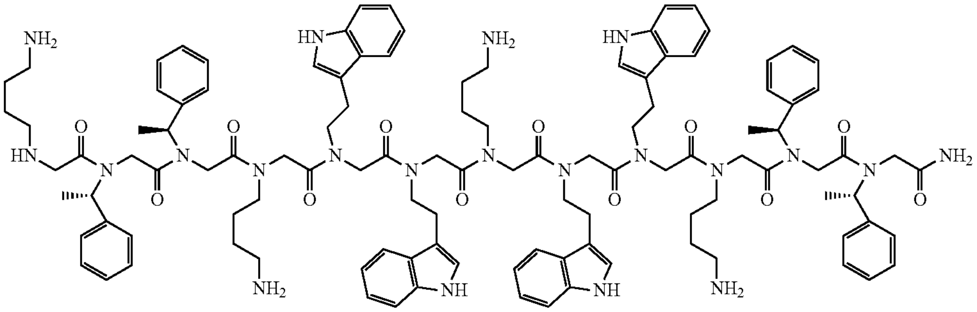 20 |
| Peptoid 21 | 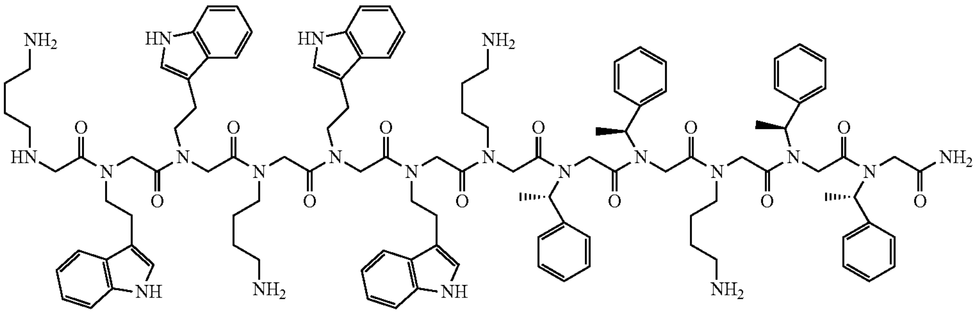 21 |
| Peptoid 22 | 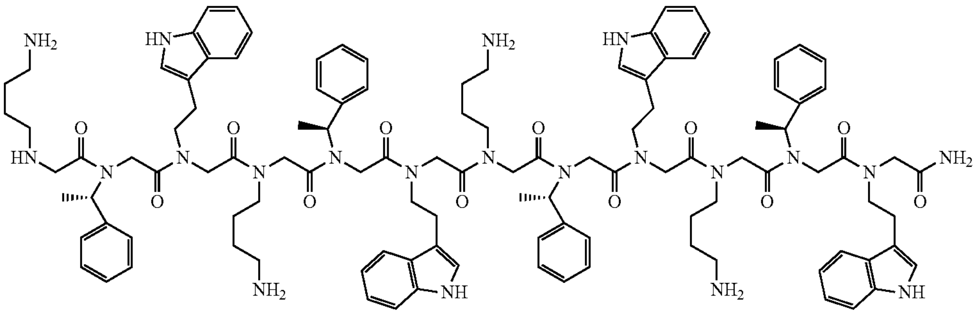 22 |

TABLE 5-continued
| Classification | Chemical Structure |
|---|---|
| Peptoid 23 | 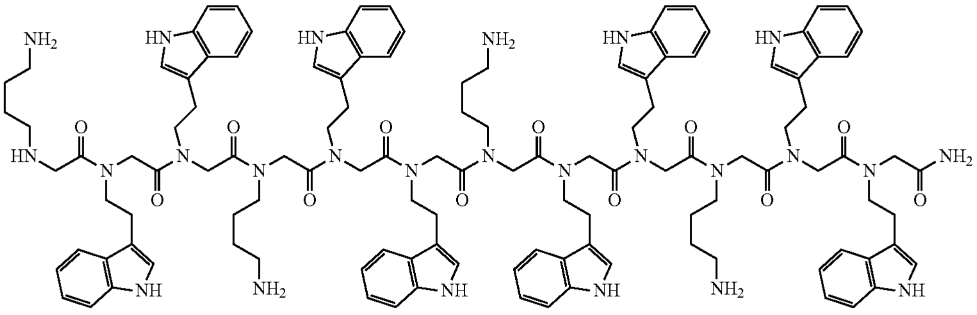 23 |
TABLE 6
| Classification | Chemical Structure |
|---|---|
| Peptoid 24 | 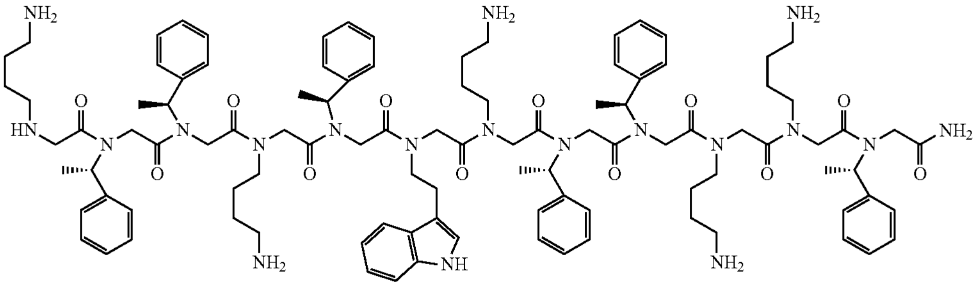 [SMILES: C[C@@H](c1ccccc1)N(CC(N)=O)C(=O)CN(CCCCN)C(=O)CN(CCCCN)C(=O)CN(C(=O)CN(C(=O)CN(CCCCN)C(=O)CN(CCc1c[nH]c2ccccc12)C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 24 |
| Peptoid 25 | 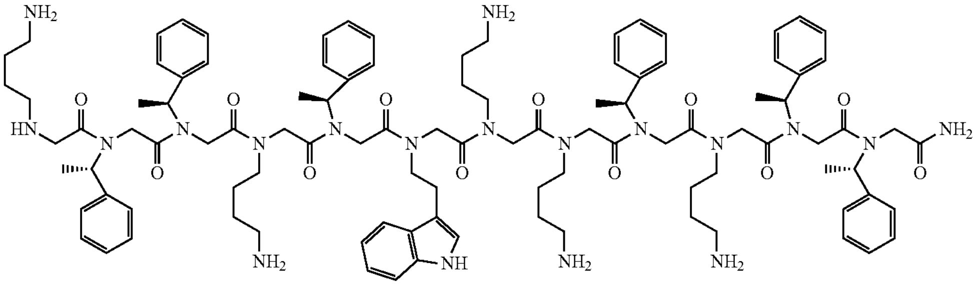 [SMILES: C[C@@H](c1ccccc1)N(CC(N)=O)C(=O)CN(C(=O)CN(CCCCN)C(=O)CN(C(=O)CN(CCCCN)C(=O)CN(CCCCN)C(=O)CN(CCc1c[nH]c2ccccc12)C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 25 |
| Peptoid 26 | 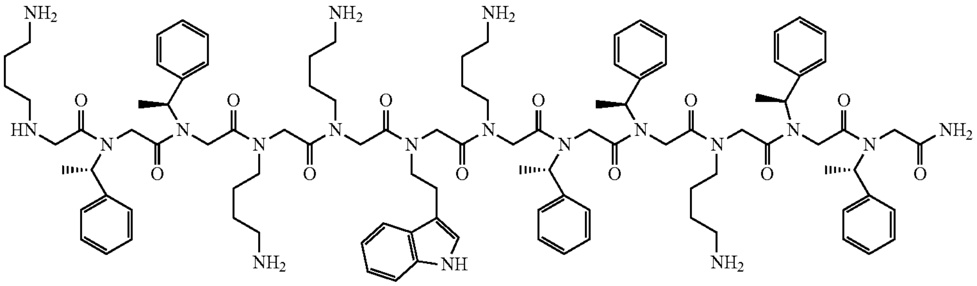 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(CCc1c[nH]c2ccccc12)C(=O)CN(CCCCN)C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 26 |

TABLE 6-continued
| Classification | Chemical Structure |
| --- | --- |
| Peptoid 27 | 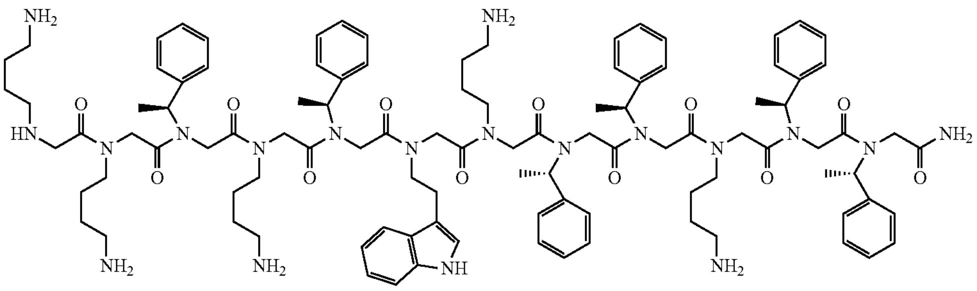 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(CCc1c[nH]c2ccccc12)C(=O)CN(C(=O)CN(CCCCN)C(=O)CN(C(=O)CN(CCCCN)C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 27 |
| Peptoid 28 | 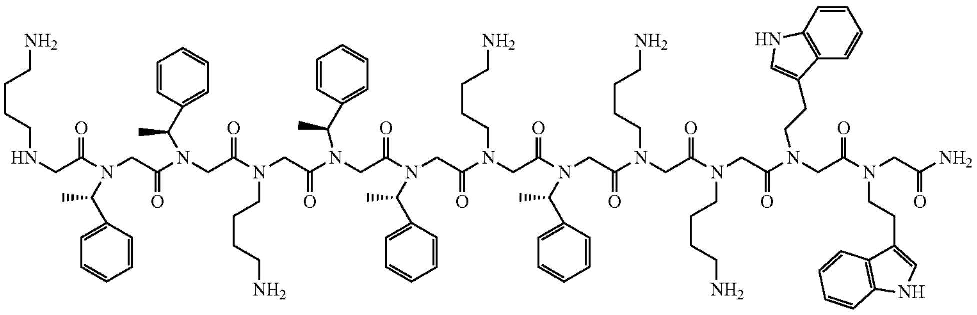 [SMILES: C[C@@H](c1ccccc1)N(CC(=O)N(CCCCN)CC(=O)N(CCCCN)CC(=O)N(CCc1c[nH]c2ccccc12)CC(=O)N(CCc1c[nH]c2ccccc12)CC(N)=O)C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1] 28 |
| Peptoid 29 | 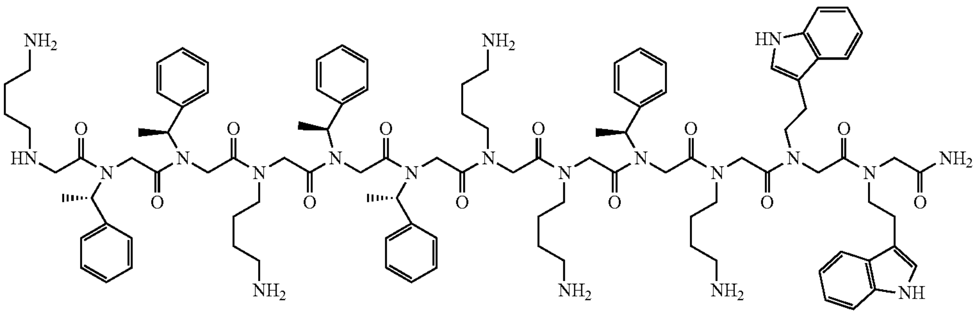 [SMILES: C[C@@H](c1ccccc1)N(CC(=O)N(CCCCN)CC(=O)N(CCc1c[nH]c2ccccc12)CC(=O)N(CCc1c[nH]c2ccccc12)CC(N)=O)C(=O)CN(CCCCN)C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1] 29 |
| Peptoid 30 | 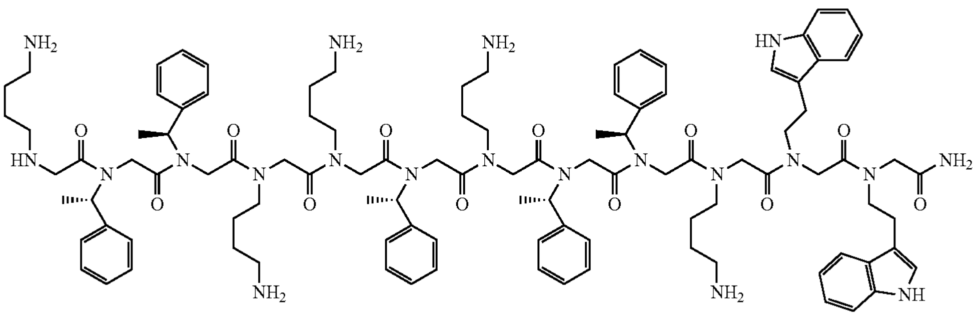 [SMILES: C[C@@H](c1ccccc1)N(CC(=O)N(CCCCN)CC(=O)N(CC(=O)N(CC(=O)N(CCCCN)CC(=O)N(CCc1c[nH]c2ccccc12)CC(=O)N(CCc1c[nH]c2ccccc12)CC(N)=O)[C@@H](C)c1ccccc1)[C@@H](C)c1ccccc1)C(=O)CN(CCCCN)C(=O)CN(CCCCN)C(=O)CN(C(=O)CN(C(=O)CNCCCCN)[C@@H](C)c1ccccc1)[C@@H](C)c1ccccc1] 30 |

TABLE 6-continued
| Classification | Chemical Structure |
| --- | --- |
| Peptoid 31 | 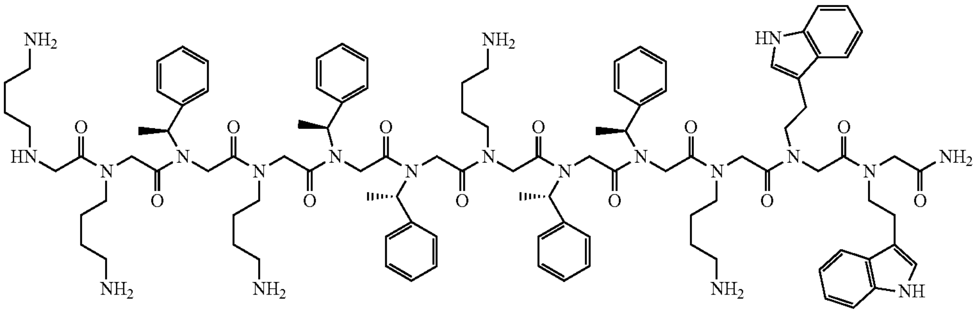 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CCc1c[nH]c2ccccc12)CC(=O)N(CCc1c[nH]c2ccccc12)CC(N)=O)[C@@H](C)c1ccccc1)[C@@H](C)c1ccccc1)[C@@H](C)c1ccccc1)[C@@H](C)c1ccccc1)C(=O)CN(CCCCN)C(=O)CNCCCCN] 31 |
| Peptoid 32 | 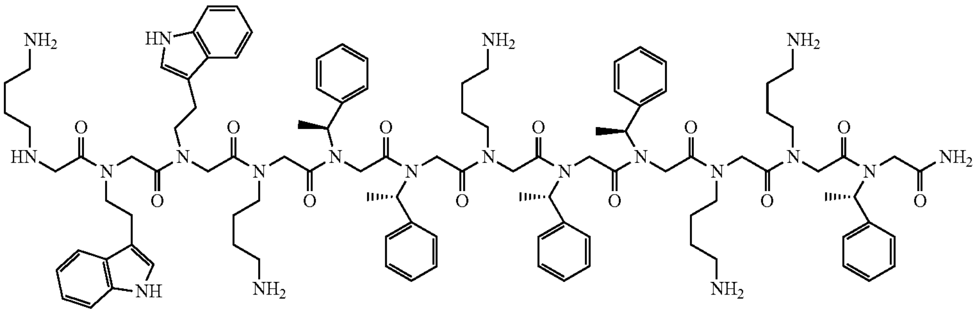 [SMILES: C[C@@H](c1ccccc1)N(CC(N)=O)C(=O)CN(CCCCN)C(=O)CN(CCCCN)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1] 32 |
| Peptoid 33 | 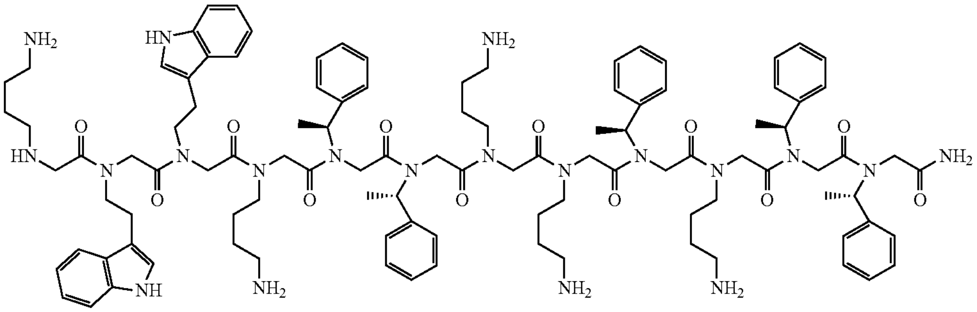 [SMILES: C[C@@H](c1ccccc1)N(CC(N)=O)C(=O)CN(C(=O)CN(CCCCN)C(=O)CN(C(=O)CN(CCCCN)C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1] 33 |
| Peptoid 34 | 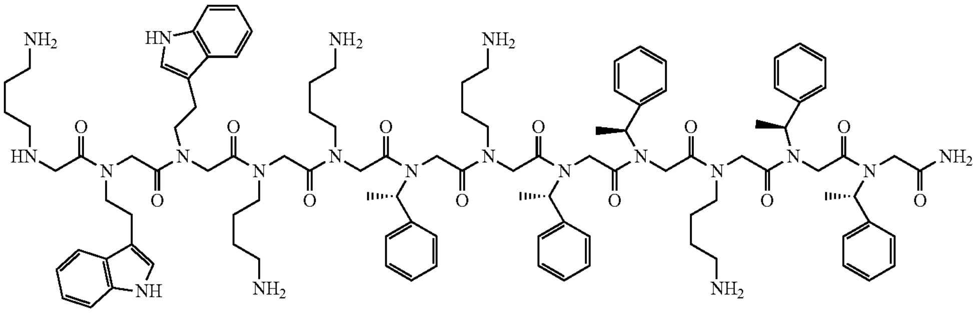 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(CCCCN)C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1] 34 |

TABLE 6-continued
| Classification | Chemical Structure |
| --- | --- |
| Peptoid 35 | 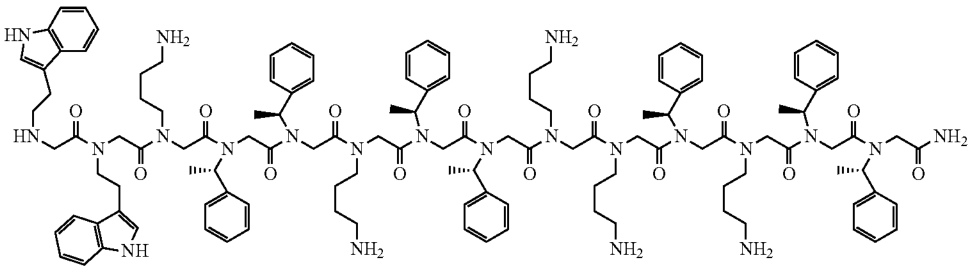 [SMILES: C[C@@H](c1ccccc1)N(CC(N)=O)C(=O)CN(C(=O)CN(CCCCN)C(=O)CN(C(=O)CN(CCCCN)C(=O)CN(CCCCN)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 35 |
| Peptoid 36 | 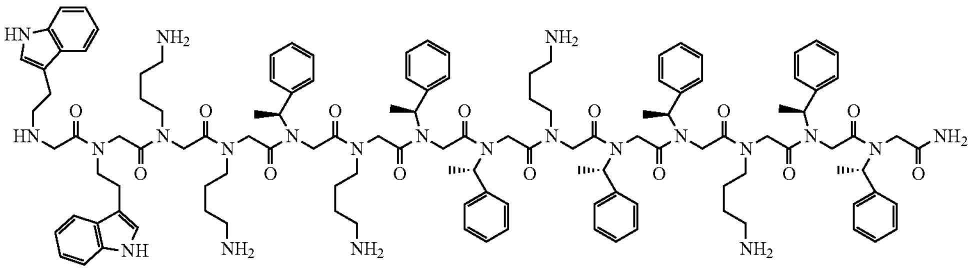 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(CCCCN)C(=O)CN(CCCCN)C(=O)CN(CCc1c[nH]c2ccccc12)C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 36 |
| Peptoid 37 | 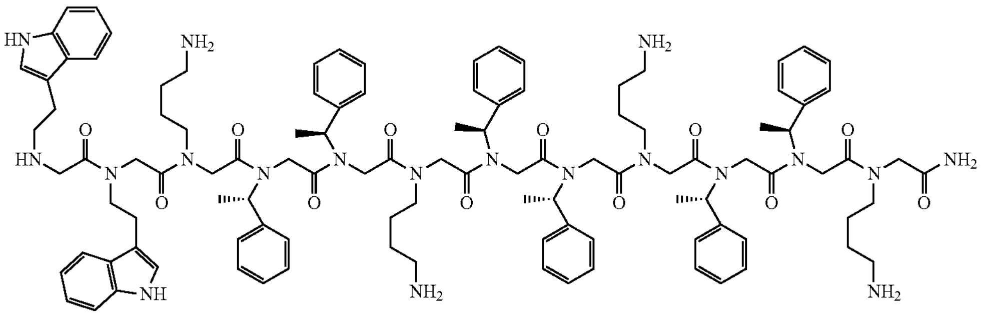 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(N)=O)[C@@H](C)c1ccccc1)[C@@H](C)c1ccccc1)[C@@H](C)c1ccccc1)[C@@H](C)c1ccccc1)C(=O)CN(C(=O)CN(CCCCN)C(=O)CN(CCc1c[nH]c2ccccc12)C(=O)CNCCc1c[nH]c2ccccc12)[C@@H](C)c1ccccc1] 37 |
| Peptoid 38 | 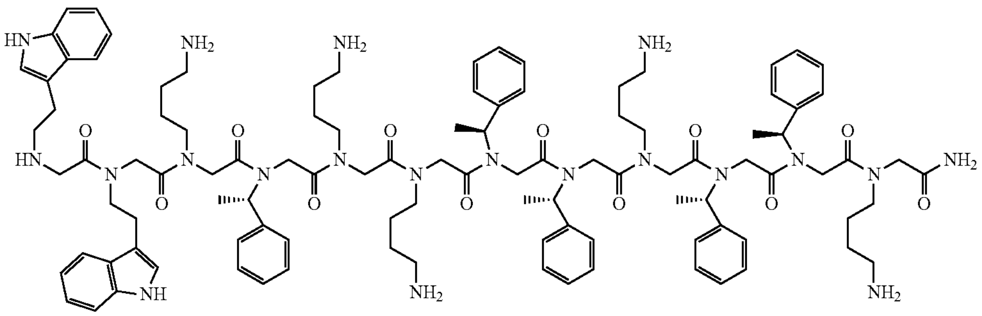 [SMILES: C[C@@H](c1ccccc1)N(CC(=O)N(CCCCN)CC(=O)N(CCCCN)CC(=O)N(CC(=O)N(CC(=O)N(CCCCN)CC(=O)N(CC(=O)N(CC(=O)N(CCCCN)CC(N)=O)[C@@H](C)c1ccccc1)[C@@H](C)c1ccccc1)[C@@H](C)c1ccccc1)[C@@H](C)c1ccccc1)C(=O)CN(CCCCN)C(=O)CN(CCc1c[nH]c2ccccc12)C(=O)CNCCc1c[nH]c2ccccc12] 38 |

TABLE 6-continued
| Classification | Chemical Structure |
| --- | --- |
| Peptoid 39 | 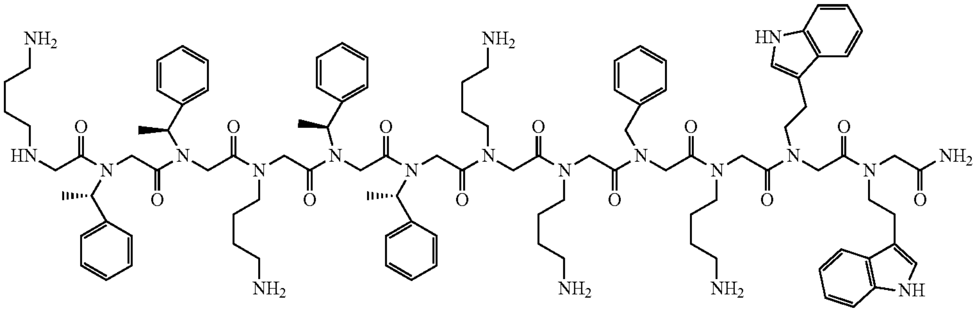 [SMILES: C[C@@H](c1ccccc1)N(CC(=O)N(CCCCN)CC(=O)N(CC(=O)N(CC(=O)N(CCCCN)CC(=O)N(CCCCN)CC(=O)N(CC(=O)N(CCCCN)CC(=O)N(CCc1c[nH]c2ccccc12)CC(=O)N(CCc1c[nH]c2ccccc12)CC(N)=O)Cc1ccccc1)[C@@H](C)c1ccccc1)[C@@H](C)c1ccccc1)C(=O)CN(C(=O)CNCCCCN)[C@@H](C)c1ccccc1] 39 |
| Peptoid 40 | 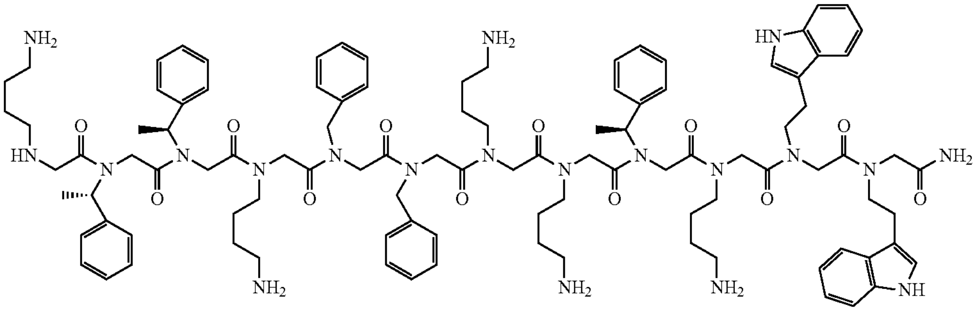 [SMILES: C[C@@H](c1ccccc1)N(CC(=O)N(CCCCN)CC(=O)N(CCc1c[nH]c2ccccc12)CC(=O)N(CCc1c[nH]c2ccccc12)CC(N)=O)C(=O)CN(CCCCN)C(=O)CN(CCCCN)C(=O)CN(Cc1ccccc1)C(=O)CN(Cc1ccccc1)C(=O)CN(CCCCN)C(=O)CN(C(=O)CN(C(=O)CNCCCCN)[C@@H](C)c1ccccc1)[C@@H](C)c1ccccc1] 40 |
| Peptoid 41 | 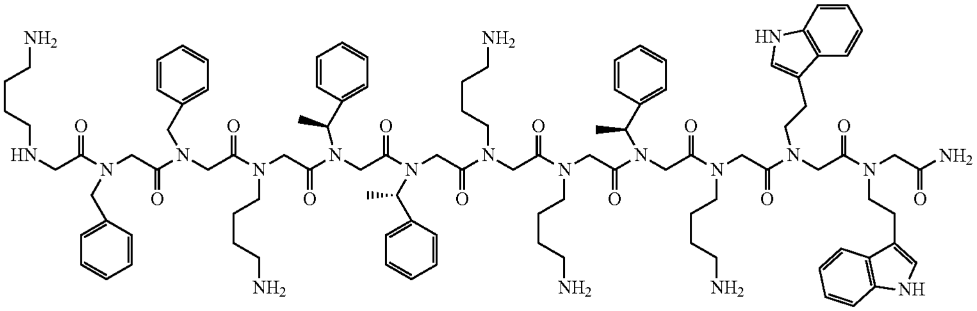 [SMILES: C[C@@H](c1ccccc1)N(CC(=O)N(CCCCN)CC(=O)N(CCc1c[nH]c2ccccc12)CC(=O)N(CCc1c[nH]c2ccccc12)CC(N)=O)C(=O)CN(CCCCN)C(=O)CN(CCCCN)C(=O)CN(C(=O)CN(C(=O)CN(CCCCN)C(=O)CN(Cc1ccccc1)C(=O)CN(Cc1ccccc1)C(=O)CNCCCCN)[C@@H](C)c1ccccc1)[C@@H](C)c1ccccc1] 41 |
| Peptoid 42 | 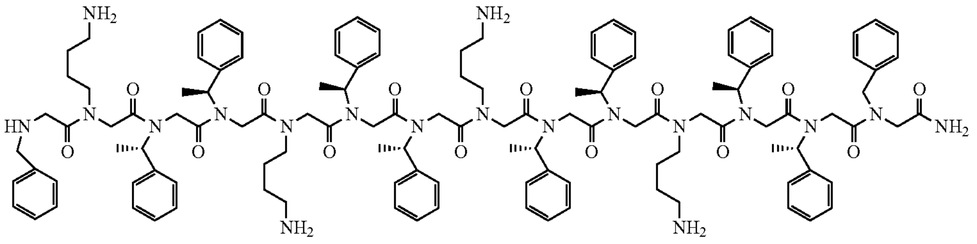 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(=O)N(CC(N)=O)Cc1ccccc1)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)C(=O)CN(C(=O)CN(CCCCN)C(=O)CNCc1ccccc1)[C@@H](C)c1ccccc1] 42 |

TABLE 6-continued
| Classification | Chemical Structure |
| --- | --- |
| Peptoid 43 | 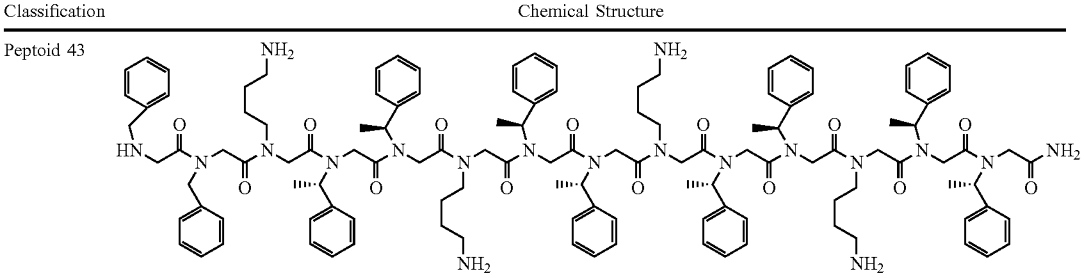 43 |
| Peptoid 44 | 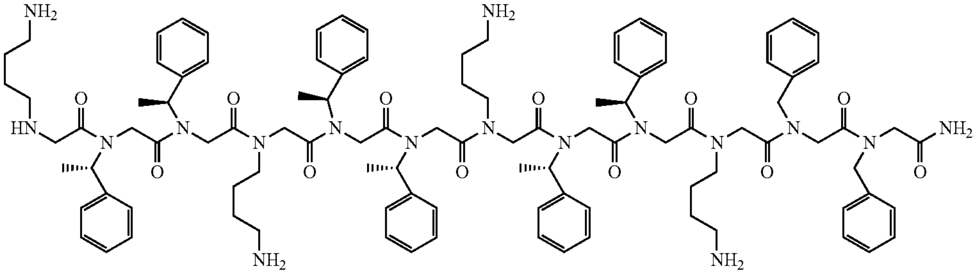 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(N)=O)Cc1ccccc1)Cc1ccccc1)[C@@H](C)c1ccccc1)[C@@H](C)c1ccccc1)[C@@H](C)c1ccccc1)[C@@H](C)c1ccccc1)C(=O)CN(C(=O)CNCCCCN)[C@@H](C)c1ccccc1] 44 |
| Peptoid 45 | 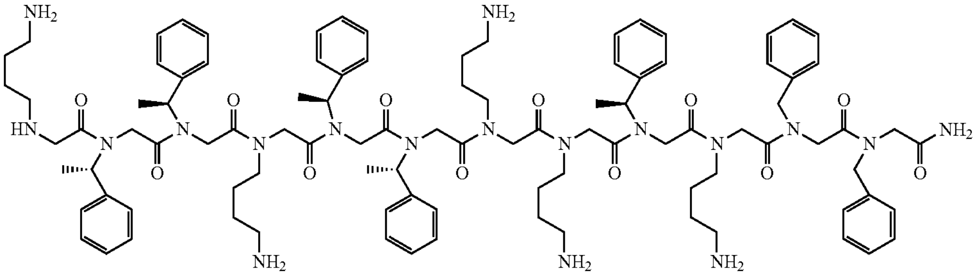 [SMILES: C[C@@H](c1ccccc1)N(CC(=O)N(CCCCN)CC(=O)N(CC(=O)N(CC(N)=O)Cc1ccccc1)Cc1ccccc1)C(=O)CN(CCCCN)C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1] 45 |
| Peptoid 46 | 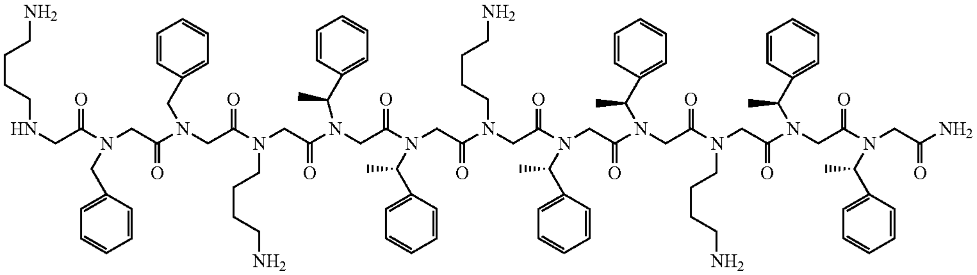 [SMILES: C[C@@H](c1ccccc1)N(CC(N)=O)C(=O)CN(C(=O)CN(CCCCN)C(=O)CN(C(=O)CN(C(=O)CN(CCCCN)C(=O)CN(C(=O)CN(C(=O)CN(CCCCN)C(=O)CN(Cc1ccccc1)C(=O)CN(Cc1ccccc1)C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 46 |
| Peptoid 47 | 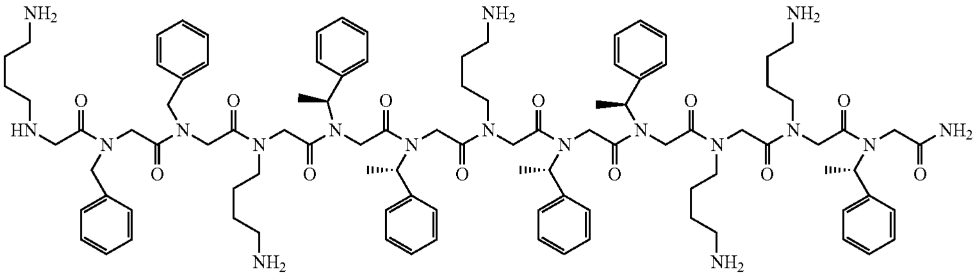 [SMILES: C[C@@H](c1ccccc1)N(CC(N)=O)C(=O)CN(CCCCN)C(=O)CN(CCCCN)C(=O)CN(C(=O)CN(C(=O)CN(CCCCN)C(=O)CN(C(=O)CN(C(=O)CN(CCCCN)C(=O)CN(Cc1ccccc1)C(=O)CN(Cc1ccccc1)C(=O)CNCCCCN)[C@@H](C)c1ccccc1)[C@@H](C)c1ccccc1)[C@@H](C)c1ccccc1)[C@@H](C)c1ccccc1] 47 |

TABLE 6-continued
| Classification | Chemical Structure |
|---|---|
| Peptoid 48 | 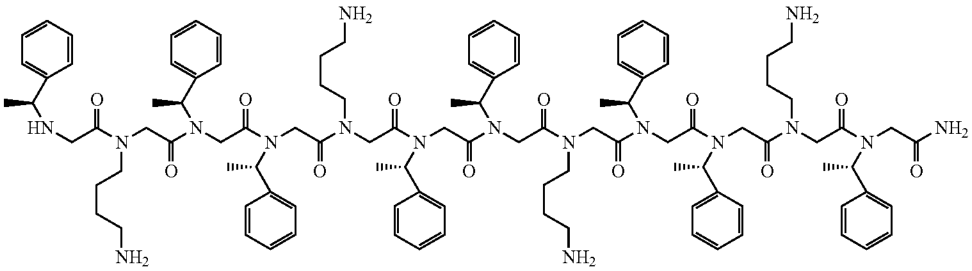 [SMILES: C[C@H](NCC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(=O)N(CCCCN)CC(=O)N(CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)c1ccccc1] 48 |
TABLE 7
| Classification | Chemical Structure |
|---|---|
| Peptoid 49 | 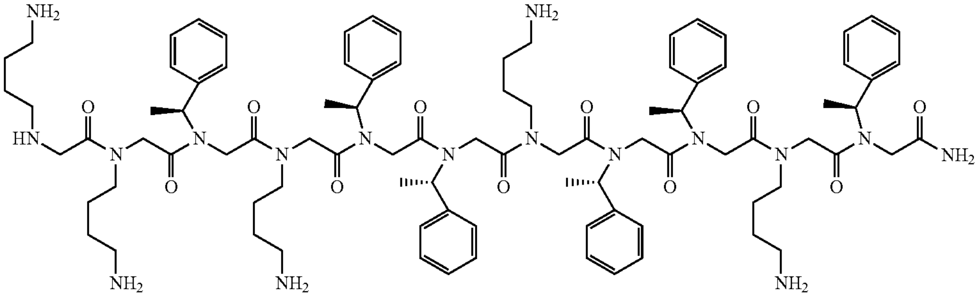 [SMILES: C[C@@H](c1ccccc1)N(CC(N)=O)C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(CCCCN)C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 49 |
| Peptoid 50 | 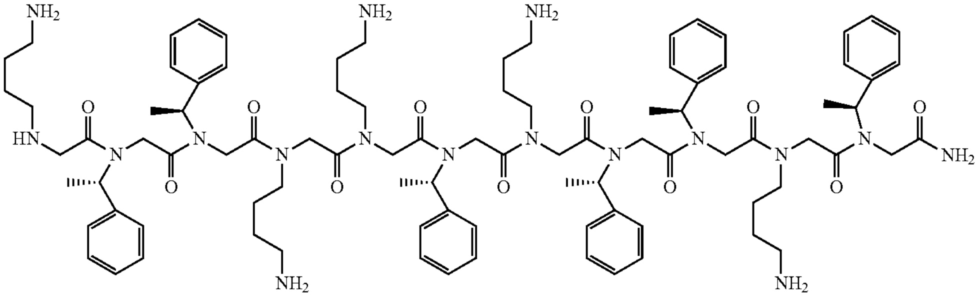 [SMILES: C[C@@H](c1ccccc1)N(CC(N)=O)C(=O)CN(CCCCN)C(=O)CN(C(=O)CN(C(=O)CN(CCCCN)C(=O)CN(C(=O)CN(CCCCN)C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 50 |
| Peptoid 51 | 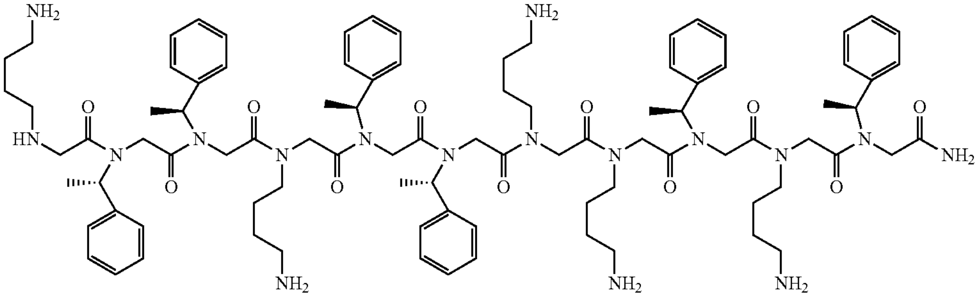 [SMILES: C[C@@H](c1ccccc1)N(CC(N)=O)C(=O)CN(CCCCN)C(=O)CN(C(=O)CN(CCCCN)C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1)[C@@H](C)c1ccccc1] 51 |

TABLE 7-continued
| Classification | Chemical Structure |
| --- | --- |
| Peptoid 52 | 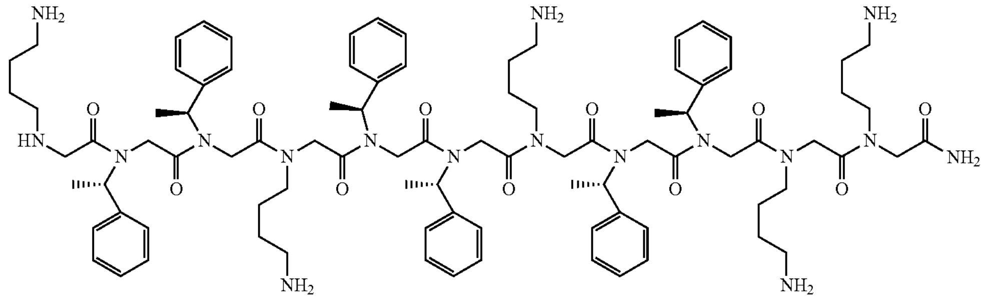 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CCCCN)CC(N)=O)[C@@H](C)c1ccccc1)[C@@H](C)c1ccccc1)[C@@H](C)c1ccccc1)[C@@H](C)c1ccccc1)C(=O)CN(C(=O)CNCCCCN)[C@@H](C)c1ccccc1] 52 |
| Peptoid 53 | 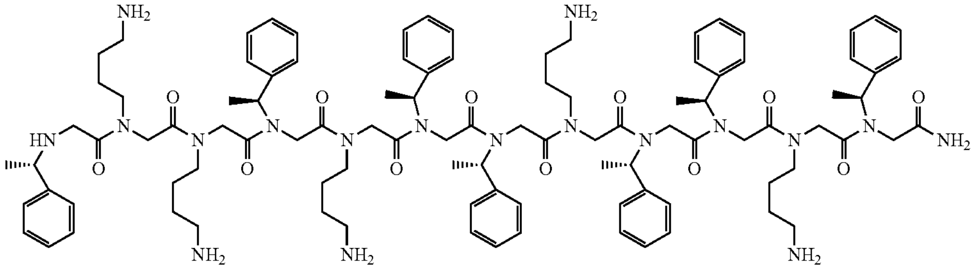 [SMILES: C[C@H](NCC(=O)N(CCCCN)CC(=O)N(CCCCN)CC(=O)N(CC(=O)N(CCCCN)CC(=O)N(CC(=O)N(CC(=O)N(CCCCN)CC(=O)N(CC(=O)N(CC(=O)N(CCCCN)CC(=O)N(CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)c1ccccc1] 53 |
| Peptoid 54 | 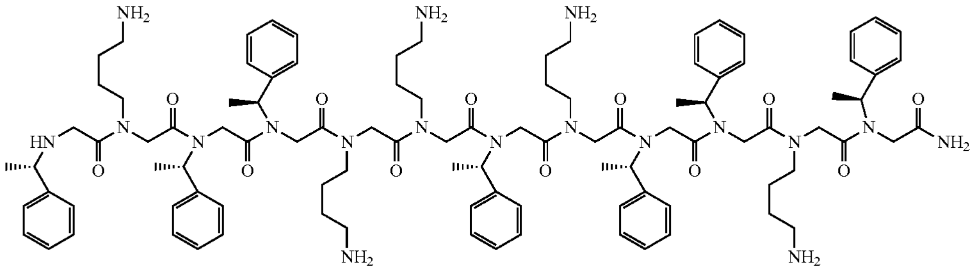 [SMILES: C[C@H](NCC(=O)N(CCCCN)CC(=O)N(CC(=O)N(CC(=O)N(CCCCN)CC(=O)N(CCCCN)CC(=O)N(CC(=O)N(CCCCN)CC(=O)N(CC(=O)N(CC(=O)N(CCCCN)CC(=O)N(CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)c1ccccc1] 54 |
| Peptoid 55 | 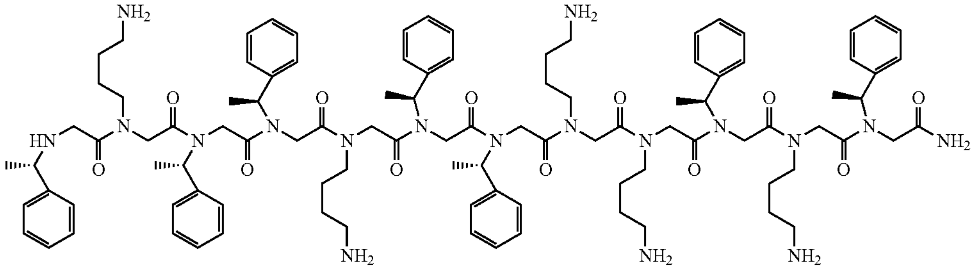 [SMILES: C[C@H](NCC(=O)N(CCCCN)CC(=O)N(CC(=O)N(CC(=O)N(CCCCN)CC(=O)N(CC(=O)N(CC(=O)N(CCCCN)CC(=O)N(CCCCN)CC(=O)N(CC(=O)N(CCCCN)CC(=O)N(CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)c1ccccc1] 55 |
| Peptoid 56 | 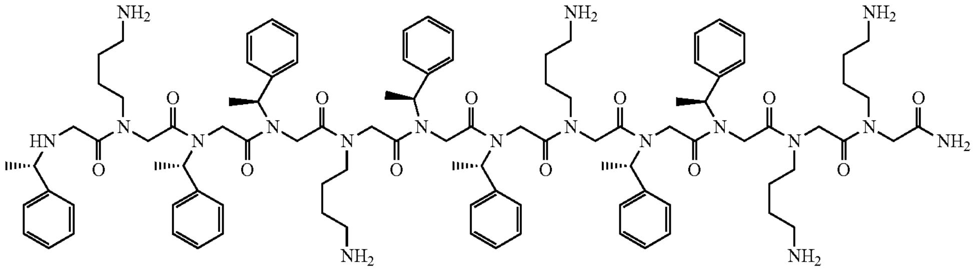 [SMILES: C[C@H](NCC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(=O)N(CCCCN)CC(=O)N(CCCCN)CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)c1ccccc1] |

TABLE 7-continued
| Classification | Chemical Structure |
| --- | --- |
| | 56 |
| Peptoid 57 | 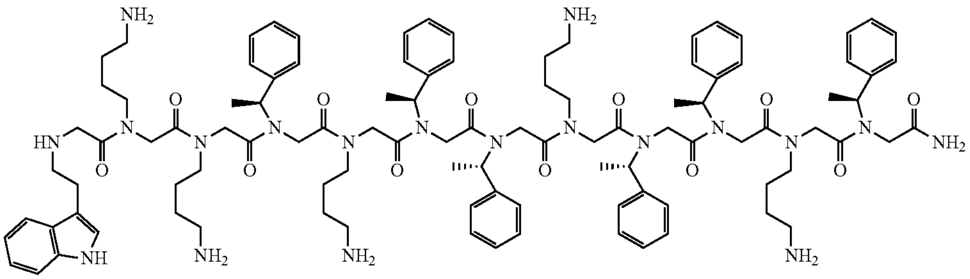 [SMILES: C[C@@H](c1ccccc1)N(CC(N)=O)C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(CCCCN)C(=O)CN(CCCCN)C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1] 57 |
| Peptoid 58 | 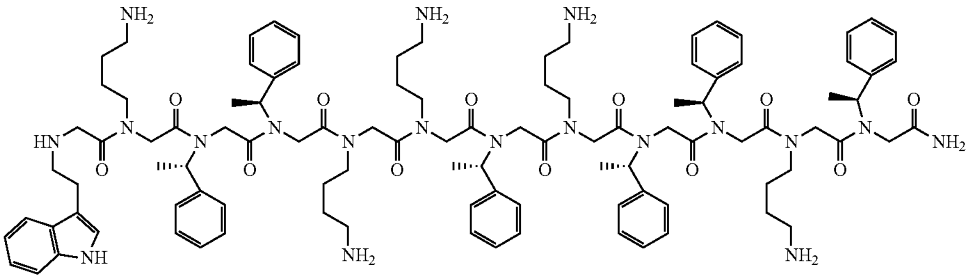 [SMILES: C[C@@H](c1ccccc1)N(CC(N)=O)C(=O)CN(CCCCN)C(=O)CN(C(=O)CN(C(=O)CN(CCCCN)C(=O)CN(C(=O)CN(CCCCN)C(=O)CN(CCCCN)C(=O)CN(C(=O)CN(C(=O)CN(CCCCN)C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1] 58 |
| Peptoid 59 | 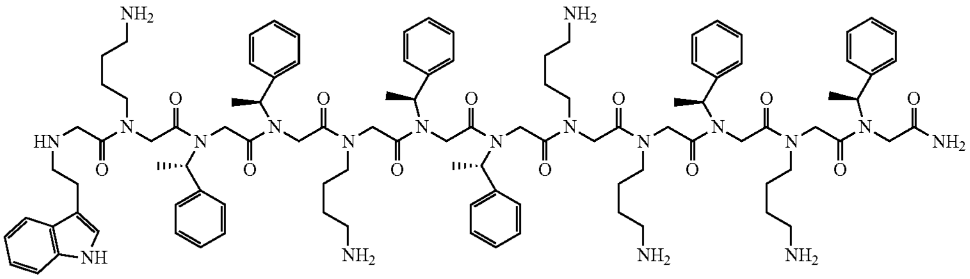 [SMILES: C[C@@H](c1ccccc1)N(CC(N)=O)C(=O)CN(CCCCN)C(=O)CN(C(=O)CN(CCCCN)C(=O)CN(CCCCN)C(=O)CN(C(=O)CN(C(=O)CN(CCCCN)C(=O)CN(C(=O)CN(C(=O)CN(CCCCN)C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1] 59 |
| Peptoid 60 | 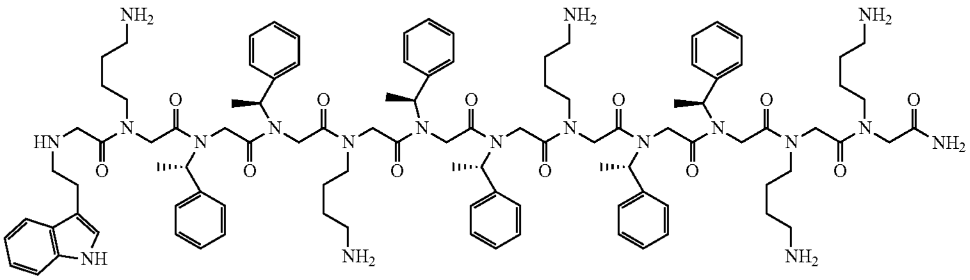 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CCCCN)CC(N)=O)[C@@H](C)c1ccccc1)[C@@H](C)c1ccccc1)[C@@H](C)c1ccccc1)[C@@H](C)c1ccccc1)C(=O)CN(C(=O)CN(CCCCN)C(=O)CNCCc1c[nH]c2ccccc12)[C@@H](C)c1ccccc1] 60 |

TABLE 7-continued
| Classification | Chemical Structure |
| --- | --- |
| Peptoid 61 | 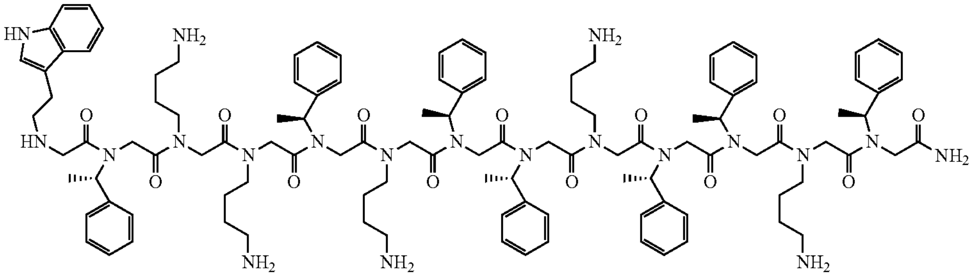 [SMILES: C[C@@H](c1ccccc1)N(CC(N)=O)C(=O)CN(CCCCN)C(=O)CN(C(=O)CN(C(=O)CN(CCCCN)C(=O)CN(C(=O)CN(C(=O)CN(CCCCN)C(=O)CN(C(=O)CN(CCCCN)C(=O)CN(CCCCN)C(=O)CN(C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 61 |
| Peptoid 62 | 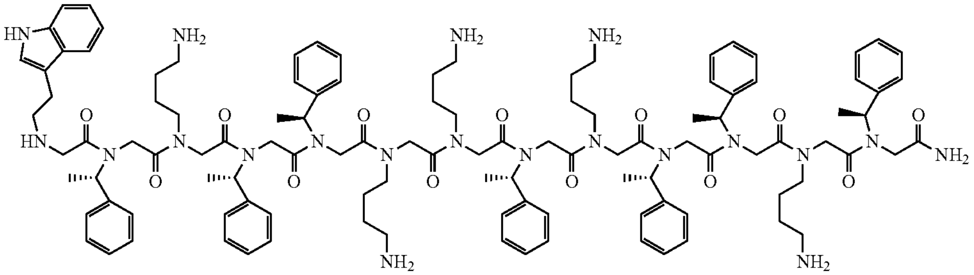 [SMILES: C[C@@H](c1ccccc1)N(CC(N)=O)C(=O)CN(CCCCN)C(=O)CN(C(=O)CN(C(=O)CN(CCCCN)C(=O)CN(C(=O)CN(CCCCN)C(=O)CN(CCCCN)C(=O)CN(C(=O)CN(C(=O)CN(CCCCN)C(=O)CN(C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 62 |
| Peptoid 63 | 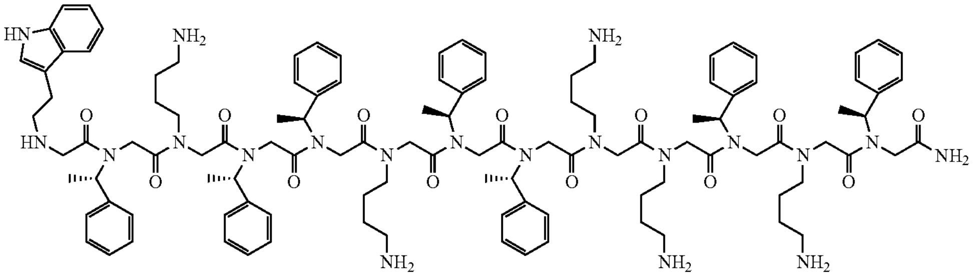 [SMILES: C[C@@H](c1ccccc1)N(CC(N)=O)C(=O)CN(CCCCN)C(=O)CN(C(=O)CN(CCCCN)C(=O)CN(CCCCN)C(=O)CN(C(=O)CN(C(=O)CN(CCCCN)C(=O)CN(C(=O)CN(C(=O)CN(CCCCN)C(=O)CN(C(=O)CNCCc1c[nH]c2ccccc12)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1] 63 |
| Peptoid 64 | 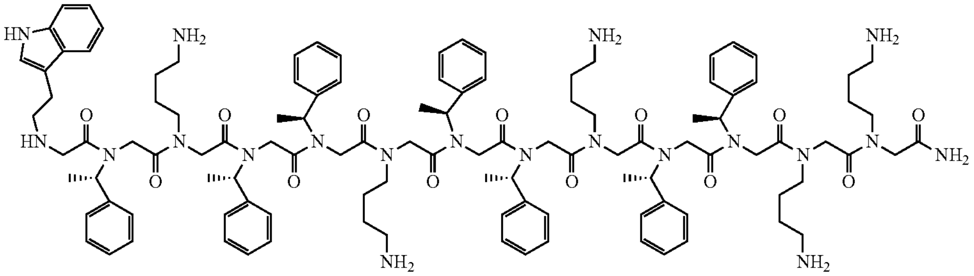 [SMILES: C[C@@H](c1ccccc1)N(CC(=O)N(CCCCN)CC(=O)N(CC(=O)N(CC(=O)N(CCCCN)CC(=O)N(CC(=O)N(CC(=O)N(CCCCN)CC(=O)N(CC(=O)N(CC(=O)N(CCCCN)CC(=O)N(CCCCN)CC(N)=O)[C@@H](C)c1ccccc1)[C@@H](C)c1ccccc1)[C@@H](C)c1ccccc1)[C@@H](C)c1ccccc1)[C@@H](C)c1ccccc1)[C@@H](C)c1ccccc1)C(=O)CNCCc1c[nH]c2ccccc12] 64 |

TABLE 7-continued

| Classification | Chemical Structure |
|---|---|
| Peptoid 65 | 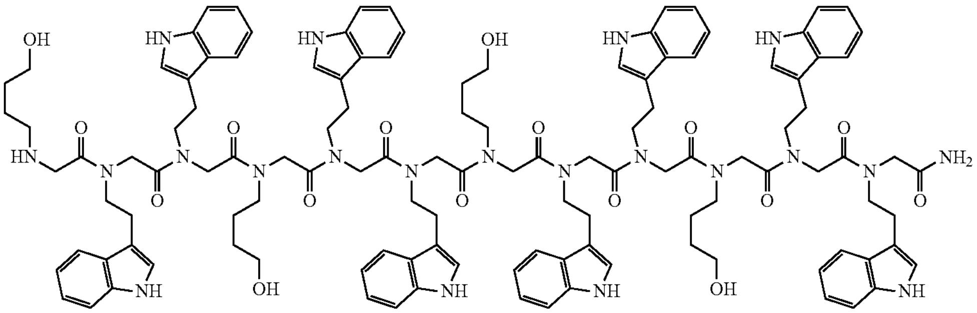 [SMILES: NC(=O)CN(CCc1c[nH]c2ccccc12)C(=O)CN(CCc1c[nH]c2ccccc12)C(=O)CN(CCCCO)C(=O)CN(CCc1c[nH]c2ccccc12)C(=O)CN(CCc1c[nH]c2ccccc12)C(=O)CN(CCCCO)C(=O)CN(CCc1c[nH]c2ccccc12)C(=O)CN(CCc1c[nH]c2ccccc12)C(=O)CN(CCCCO)C(=O)CN(CCc1c[nH]c2ccccc12)C(=O)CN(CCc1c[nH]c2ccccc12)C(=O)CNCCCCO] 65 |
| Peptoid 66 | 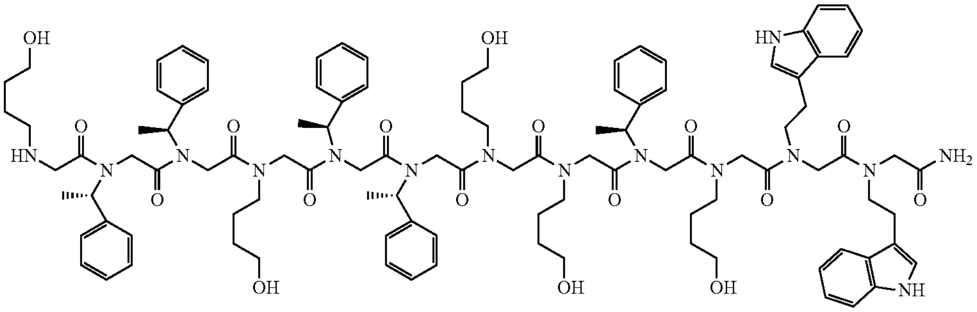 [SMILES: C[C@@H](c1ccccc1)N(CC(=O)N(CCCCO)CC(=O)N(CCc1c[nH]c2ccccc12)CC(=O)N(CCc1c[nH]c2ccccc12)CC(N)=O)C(=O)CN(CCCCO)C(=O)CN(CCCCO)C(=O)CN(C(=O)CN(C(=O)CN(CCCCO)C(=O)CN(C(=O)CN(C(=O)CNCCCCO)[C@@H](C)c1ccccc1)[C@@H](C)c1ccccc1)[C@@H](C)c1ccccc1)[C@@H](C)c1ccccc1] 66 |

TABLE 8

| Classification | Number of NhTrps | CTLR | HPLC elution (% ACN) |
|---|---|---|---|
| Peptoid 1 | 0 | 0.33 | 54.5 |
| Peptoid 2 | 0 | 0.33 | 50.7 |
| Peptoid 3 | 1 | 0.31 | 55.8 |
| Peptoid 4 | 1 | 0.31 | 57 |
| Peptoid 5 | 2 | 0.29 | 58.6 |
| Peptoid 6 | 2 | 0.29 | 57.2 |
| Peptoid 7 | 1 | 0.33 | 54.1 |
| Peptoid 8 | 1 | 0.33 | 54.5 |
| Peptoid 9 | 1 | 0.33 | 54.6 |
| Peptoid 10 | 1 | 0.33 | 54.9 |
| Peptoid 11 | 2 | 0.33 | 54 |
| Peptoid 12 | 2 | 0.33 | 55.9 |
| Peptoid 13 | 2 | 0.33 | 56 |
| Peptoid 14 | 2 | 0.33 | 55.6 |
| Peptoid 15 | 2 | 0.33 | 53.7 |
| Peptoid 16 | 2 | 0.33 | 54.7 |
| Peptoid 17 | 2 | 0.33 | 56 |
| Peptoid 18 | 4 | 0.33 | 53.8 |
| Peptoid 19 | 4 | 0.33 | 52.8 |
| Peptoid 20 | 1 | 0.33 | 52.7 |
| Peptoid 21 | 4 | 0.33 | 53.2 |
| Peptoid 22 | 4 | 0.33 | 54.1 |
| Peptoid 23 | 8 | 0.33 | 153 |

TABLE 9

| Classification | Number of NhTrps | CTLR | HPLC elution (% ACN) |
|---|---|---|---|
| Peptoid 24 | 1 | 0.42 | 49.4 |
| Peptoid 25 | 1 | 0.42 | 50.8 |
| Peptoid 26 | 1 | 0.42 | 49.5 |
| Peptoid 27 | 1 | 0.42 | 50.7 |
| Peptoid 28 | 2 | 0.42 | 48.6 |

TABLE 9-continued

| Classification | Number of NhTrps | CTLR | HPLC elution (% ACN) |
|---|---|---|---|
| Peptoid 29 | 2 | 0.42 | 48.6 |
| Peptoid 30 | 2 | 0.42 | 48.8 |
| Peptoid 31 | 2 | 0.42 | 50.2 |
| Peptoid 32 | 2 | 0.42 | 48.4 |
| Peptoid 33 | 2 | 0.42 | 47.9 |
| Peptoid 34 | 2 | 0.42 | 48.6 |
| Peptoid 35 | 2 | 0.36 | 51.8 |
| Peptoid 36 | 2 | 0.36 | 52.4 |
| Peptoid 37 | 2 | 0.33 | 52.7 |
| Peptoid 38 | 2 | 0.42 | 47.8 |
| Peptoid 39 | 2 | 0.42 | 47.8 |
| Peptoid 40 | 2 | 0.42 | 47.5 |
| Peptoid 41 | 2 | 0.42 | 47.5 |
| Peptoid 42 | 0 | 0.29 | 57.7 |
| Peptoid 43 | 0 | 0.29 | 56.8 |
| Peptoid 44 | 0 | 0.33 | 53.1 |
| Peptoid 45 | 0 | 0.42 | 47.3 |
| Peptoid 46 | 0 | 0.33 | 53.7 |
| Peptoid 47 | 0 | 0.42 | 47.8 |
| Peptoid 48 | 0 | 0.33 | 53.4 |

TABLE 10

| Classification | Number of NhTrps | CTLR | HPLC elution (% ACN) |
|---|---|---|---|
| Peptoid 49 | 0 | 0.45 | 46.6 |
| Peptoid 50 | 0 | 0.45 | 46.1 |
| Peptoid 51 | 0 | 0.45 | 45.3 |
| Peptoid 52 | 0 | 0.45 | 46.9 |
| Peptoid 53 | 0 | 0.42 | 48.5 |
| Peptoid 54 | 0 | 0.42 | 48.1 |
| Peptoid 55 | 0 | 0.42 | 47.2 |
| Peptoid 56 | 0 | 0.42 | 48 |

TABLE 10-continued

| Classification | Number of NhTrps | CTLR | HPLC elution (% ACN) |
|---|---|---|---|
| Peptoid 57 | 1 | 0.42 | 49.1 |
| Peptoid 58 | 1 | 0.42 | 48.7 |
| Peptoid 59 | 1 | 0.42 | 47.8 |
| Peptoid 60 | 1 | 0.42 | 48.6 |
| Peptoid 61 | 1 | 0.38 | 51.2 |
| Peptoid 62 | 1 | 0.38 | 50.8 |
| Peptoid 63 | 1 | 0.38 | 49.9 |
| Peptoid 64 | 1 | 0.38 | 50.5 |
| Peptoid 65 | 8 | 0 | 66.7 |
| Peptoid 66 | 2 | 0 | 64.7 |

Analysis Example 1: HPLC and LC-MS Analysis

The synthesized peptoids were purified and analyzed using an HPLC system (SunFire C18, 4.6×250 mm, 5 μm; Waters Corp, USA). The structure and HPLC analysis results of the synthesized peptoids are shown in Tables 8 to 10. Here, CTLR refers to a charge-to-length-ratio, defined as a ratio of the number of cationic residues to the number of total residues in each sequence. In addition, in HPLC elution analysis, water (containing 0.1% TFA) and acetonitrile (containing 0.1% TFA) were used as mobile phases. As a result, the synthesized peptoids generally showed a retention time within the range of 45 minutes to 60 minutes in the HPLC elution analysis, confirming the degree of hydrophobicity of the synthesized peptoids.

Analysis Example 2: Circular Dichroism (CD) Spectroscopy

CD spectroscopy is a spectroscopic analysis method used to identify the secondary structure of a biomolecule such as a protein, a peptide, or a nucleic acid, and CD spectra were measured using a Jasco model 815 spectropolarimeter (Jasco, USA). CD spectroscopy was performed on a peptoid salt (50 μM in ACN) at room temperature. For the peptoid concentration, the dry weight of a lyophilized peptoid based on a TFA salt was used.

Figure 2:
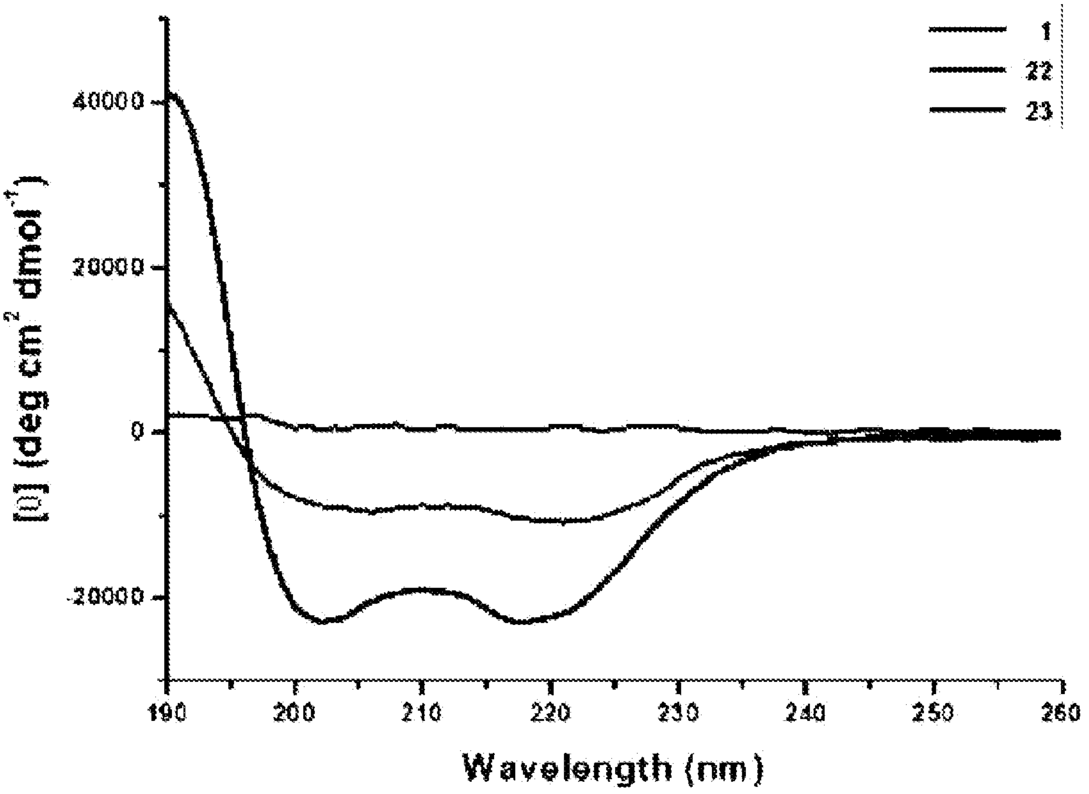
FIGS. 2 to 4 are graphs showing circular dichroism spectra in the range of 190 nm to 260 nm of an antimicrobial peptoid according to one embodiment of the present inventive concept.
Figure 3:
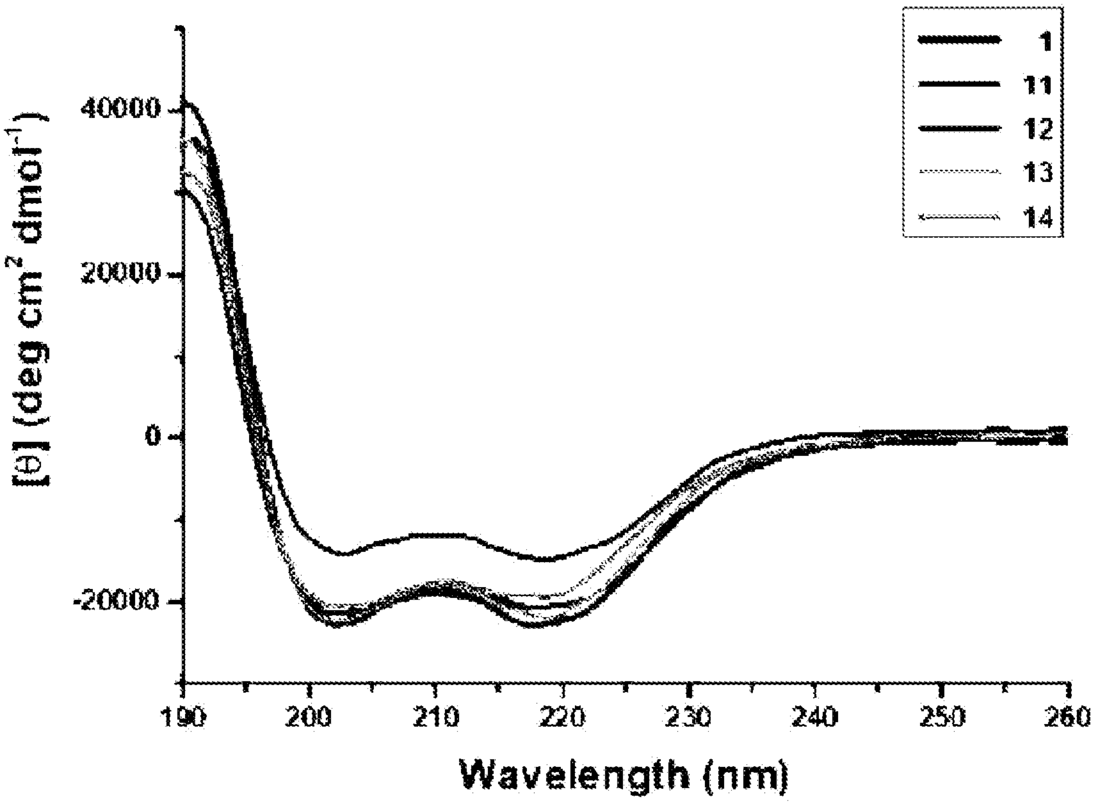
Figure 4:
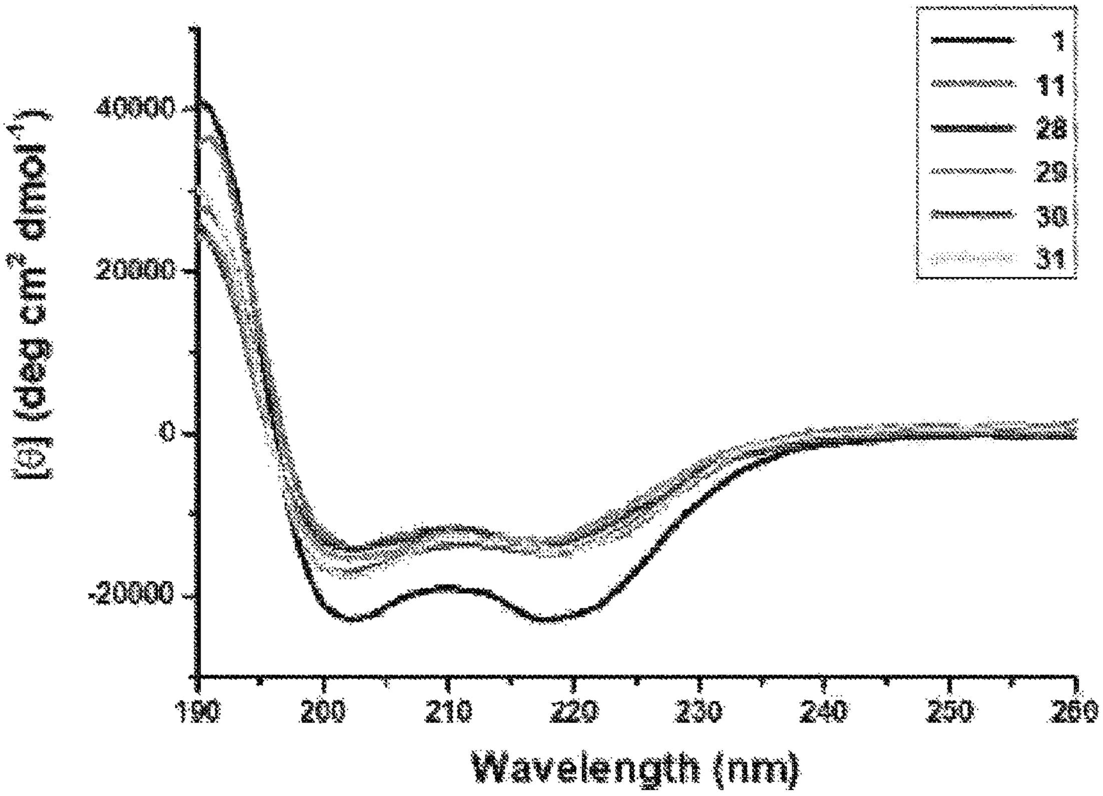

FIGS. 2 to 4 are graphs showing CD spectra for examples at 190 nm to 260 nm.

Referring to FIG. 2, it can be seen that a peak is shown at 200 nm and 220 nm, indicating that Peptoid 1 has an alpha helix. Meanwhile, it can be confirmed that, in Peptoids 22 and 23 having a peptoid group substituted with NhTrp, peak intensities at 200 nm and 220 nm were reduced, and peaks disappeared.

In addition, referring to FIG. 3, the CD spectra of Peptoids 11 to 14 were measured to determine a structural change according to the position of NhTrp substituted in Peptode 1. In the case of Peptoid 11, compared to other peptoid isomers, the peak intensities at 200 nm and 220 nm were greatly reduced when the C-terminus was replaced with NhTrp. Accordingly, it can be seen that two adjacent NhTrps of C-terminus included in the Peptoid 11 affect the secondary structure of the peptoid.

Meanwhile, referring to FIG. 4, CD spectra for Peptoids 28 to 31 in which cationic charges are increased by replacing Nspe in Peptoid 11 with NLys are shown. There were no significant differences in Peptoids 28 to 31, compared to Peptoid 11.

Analysis Example 3: Antimicrobial Activity Assay

To measure the antimicrobial activity of the peptoids synthesized in Example 1, an *E. coli* ATCC25922 strain as gram-negative bacteria and an *S. aureus* KCTC25923 strain as gram-positive bacteris, were treated with the peptoids, followed by measuring the minimum inhibitory concentration (MIC). Peptoids 1 and 2 are antimicrobial peptoids known in the art, and used as controls for comparing antimicrobial activity with a novel peptoid.

Specifically, the *S. aureus* KCTC25923 or *E. coli* ATCC25922 strain was inoculated into a Mueller Hinton Broth (MHB2) liquid medium in which cations had been adjusted in the medium, cultured at 37 °C for 18 hours, subcultured, and then incubated for 4 hours. Afterward, for each bacterial strain, an optical density (OD, 0.001) was adjusted so that the bacterial count became $2\times10^5$ to $5\times10^5$ colony-forming units (CFU) per mL, which was then diluted with a MHB2 liquid medium containing 0.02% bovine serum albumin and 0.001% acetic acid, and dispensed at 100 μL into a 96-well microplate. Using sterile water, a peptoid stock 40 times stronger than a concentration to be tested was subjected to two-fold serial dilution and assessed at six different concentrations, and the maximum value of the peptoid concentrations was 25 μM. Subsequently, the plate was incubated at 37 °C for 24 hours. Afterward, optical density (OD) values at 600 nm were measured using a microplate reader (Bio-Rad).

The lowest peptoid concentration preventing turbidity observed by visual inspection was recorded as the minimum inhibitory concentration (MIC), and the measurement results are shown in Tables 11 to 13 below. Each MIC value was determined as the average value of a value obtained through three independent experiments.

As a result, Peptoids 3 to 6 obtained by adding NhTrp to Peptoid 1 showed increased MIC values for *E. coli*, compared to Peptoid 1. However, MIC and $HC_{10}$ values for *S. aureus* were reduced or maintained constant.

Particularly, Peptoids 5 and 6 lost antimicrobial activities against *E. coli* even though only two NhTrps were added to Peptoid 1. Peptoids 7 to 10 in which one Nspe in Peptoid 1 was substituted with NhTrp exhibited very similar or stronger antimicrobial activities and cytotoxicity against red blood cells. Peptoids 11 to 14, and 15 to 17 in which two Nspes were substituted with NhTrp exhibited similar antimicrobial activity and cytotoxicity, compared to Peptoid 1.

On the other hand, Peptoids 18 to 22 in which four Nspe groups were substituted with NhTrp had decreased antimicrobial activity against *E. coli*, but the other aspect, cytotoxicity, remained the same.

When all Nspe groups of Peptoid 1 were replaced with NhTrp (Peptoid 23), along with the minimal change in antimicrobial activity against *S. aureus* or red blood cells, the antimicrobial activity against *E. coli* was reduced.

That is, it can be seen that the antimicrobial activity against *E. coli* tended to decrease when the helical structure is weakened by replacement of an Nspe with an indole ring, but the toxicities against gram-positive bacteria and red blood cells were maintained at a level similar to that of a benzene ring compound, Peptoid 1 (Nspe).

In addition, when samples have the same ionic charges, it was confirmed that a helical structure is associated with the MIC against *E. coli*. Accordingly, it can be seen that, as more NhTrps are substituted, the MIC against *E. coli* is lowered, and it can be confirmed that, as the position of the substituted NhTrp approaches the N-terminus, antimicrobial activity increases.

Analysis Example 4: Hemolysis Assay

To confirm cytotoxicity by the hemolytic activity of each peptoid synthesized in Example 1, hemolysis analysis was performed. The used blood was collected from a 13-week-old male Sprague-Dawley mouse in a tube containing 158 UPS sodium heparin for preventing coagulation, and centrifuged at 4 °C for 10 minutes at 1,000 rpm. Afterward, the plasma was carefully removed, red blood cells were washed with phosphate-buffered saline (PBS: a mixed solution of 35 mM phosphate-buffered solution/150 mM NaCl, pH 7.4) three times and centrifuged at 1,000 rpm for 10 minutes. A 10% (v/v) red blood cell solution diluted in PBS was dispensed at 150 μL into a 96-well plate (microtiter plate), a peptoid solution was added at 50 μL, and 1% Triton X-100 was added.

Afterward, the red blood cells were incubated at 37 °C for 1 hour, and the incubated 96-well plate was centrifuged at 1,000 rpm for 15 minutes. A supernatant was obtained and transferred to a new 96-well plate at 150 μL, and absorbance was measured using a spectrophotometer at 540 nm. Percent hemolysis may be calculated by the following Equation 1, and the corresponding results are shown in Tables 11 to 13.

$$\% \text{ Hemolysis}=(A-C)/(B-C)\times 100 \quad \text{[Equation 1]}$$

In Equation 1, A is the absorbance of the peptoid solution at 540 nm, B is the absorbance of the 0.1% Triton X-100 at 540 nm, and C is the absorbance of the PBS solution at 540 nm.

In Tables 11 to 13 below, $HC_{10}$ indicates the concentration of a peptoid that induces hemolysis in 10% red blood cells, and $HC_{50}$ indicates the concentration of a peptoid that induces hemolysis in 50% red blood cells. In addition, $H_{max}$ is the hemolysis rate (%) at 200 μM, which is the maximum concentration of a peptoid used in the experiment. The term "nd" in the following Tables 11 to 13 is the abbreviation for not determined, and indicates a value that is too small or too large to be measured.

Analysis Example 5: Analysis of Selectivity of Peptoid

The term "selectivity" used herein refers to a comparative value for antimicrobial activity and mammalian cytotoxicity, and the higher the selectivity value, the lower the toxicity. To confirm peptoid selectivity, the selectivity of each peptoid was calculated using the results measured in Experimental Examples 1 and 2. For selectivity, values calculated by dividing $HC_{10}$ values by MIC against *E. coli* were shown in Tables 11 to 13 below. All values were determined by the average value of the numbers obtained through three independent experiments, and an experimental error was less than 10%.

Referring to Tables 11 to 13 below, the highest selectivity was shown in Peptoids 29 and 32. Accordingly, among Peptoids 1 to 66, Peptoids 29 and 32 were able to be selected as peptoids with high antimicrobial activity and low red blood cell toxicity.

TABLE 11

| Peptoid | MIC (μM) *E. coli* ATCC 25922 | MIC (μM) *S. aureus* ATCC 25923 | $HC_{10}/HC_{50}$ (μM) | $H_{max}$ (100 μM) | Selectivity [$HC_{10}$/MIC (*E. coli*)] |
|---|---|---|---|---|---|
| 1 | 6.3 | 1.6 | 8.3/22.9 | 112.3 ± 0.7 | 1.3 |
| 2 | 12.5 | 3.1 | 20.4/>100.0 | 17.7 ± 1.1 | 1.6 |
| 3 | 6.3 | 1.6 | 6.3/13.9 | 100.5 ± 9.9 | 1 |
| 4 | 12.5 | 1.6 | <6.3/6.7 | 103.2 ± 0.9 | <0.5 |
| 5 | >25 | 3.1 | <6.3/15.3 | 108.1 ± 2.7 | <0.3 |
| 6 | 25 | <0.8 | 9.6/22.0 | 101.6 ± 5.8 | 10.4 |

TABLE 11-continued

| Peptoid | MIC (μM) *E. coli* ATCC 25922 | MIC (μM) *S. aureus* ATCC 25923 | $HC_{10}/HC_{50}$ (μM) | $H_{max}$ (100 μM) | Selectivity [$HC_{10}$/MIC (*E. coli*)] |
|---|---|---|---|---|---|
| 7 | 6.3 | 3.1 | 7.8/23.8 | 94.1 ± 4.3 | 1.2 |
| 8 | 6.3 | 1.6 | 12.8/28.4 | 105.1 ± 2.2 | 2 |
| 9 | 3.1 | 1.6 | 10.6/31.9 | 106.4 ± 0.6 | 3.4 |
| 10 | 3.1 | 1.6 | 6.6/17.0 | 108.1 ± 1.7 | 2.1 |
| 11 | 6.3 | 1.6 | 8.3/22.2 | 103.4 ± 3.2 | 1.3 |
| 12 | 6.3 | 1.6 | 29.1/65.2 | 87.4 ± 2.4 | 4.6 |
| 13 | 6.3 | <0.8 | 20.2/41.3 | 96.8 ± 1.6 | 3.2 |
| 14 | 3.1 | <0.8 | 23.6/43.4 | 90.0 ± 7.3 | 7.6 |
| 15 | 6.3 | 1.6 | 28.1/60.9 | 91.0 ± 2.5 | 14.5 |
| 16 | 6.3 | 1.6 | 13.8/25.0 | 100.3 ± 1.7 | 2.2 |
| 17 | 6.3 | 1.6 | 18.0/39.7 | 87.3 ± 6.7 | 2.9 |
| 18 | 12.5 | 3.1 | 14.3/37.8 | 103.5 ± 4.3 | 1.1 |
| 19 | 12.5 | 0.8 | 3.8/12.5 | 101.5 ± 1.3 | 0.3 |
| 20 | 6.3 | 1.6 | 8.2/33.9 | 106.7 ± 3.5 | 1.3 |
| 21 | 6.3 | 1.6 | 23.2/64.9 | 83.7 ± 2.0 | 3.7 |
| 22 | 12.5 | 1.6 | 6.9/19.4 | 108.6 ± 1.1 | 0.6 |
| 23 | 25 | 1.6 | 17.1/45.2 | 72.2 ± 0.3 | 0.7 |

TABLE 12

| Peptoid | MIC (μM) *E. coli* ATCC 25922 | MIC (μM) *S. aureus* ATCC 25923 | $HC_{10}/HC_{50}$ (μM) | $H_{max}$ (100 μM) | Selectivity [$HC_{10}$/MIC (*E. coli*)] |
|---|---|---|---|---|---|
| 24 | >25 | 6.3 | >100/>100 | 1.5 ± 0.0 | nd |
| 25 | >25 | 3.1 | >100/>100 | 2.7 ± 0.4 | nd |
| 25 | >25 | 6.3 | >100/>100 | 0.7 ± 0.1 | nd |
| 27 | 25 | 3.1 | >100/>100 | 5.9 ± 0.2 | nd |
| 28 | 12.5 | 6.3 | >100/>100 | 8.9 ± 1.4 | >8.0 |
| 29 | 6.3 | 6.3 | >100/>100 | 9.8 ± 1.8 | >15.9 |
| 30 | 12.5 | 3.1 | >100/>100 | 8.4 ± 0.5 | >8.0 |
| 31 | 6.3 | 3.1 | 59.0/>100 | 18.4 ± 5.0 | 9.3 |
| 32 | 6.3 | 3.1 | 77.7/>100 | 15.9 ± 1.5 | 12.3 |
| 33 | 12.5 | 3.1 | >100/>100 | 5.0 ± 0.2 | >8.0 |
| 34 | 25 | 3.1 | >100/>100 | 8.5 ± 1.1 | 4 |
| 35 | 3.1 | 10.8 | 20.4/63.0 | 82.6 ± 3.2 | 6.6 |
| 36 | 3.1 | <0.8 | 15.3/39.4 | 89.1 ± 3.4 | 4.9 |
| 37 | 3.1 | 1.6 | 21.1/57.0 | 97.4 ± 6.5 | 6.8 |
| 38 | 12.5 | 6.3 | >100/>100 | 5.9 ± 0.5 | >8.0 |
| 39 | 25 | 6.3 | 100/>100 | 10.2 ± 0.3 | 4 |
| 40 | 12.5 | 12.5 | >100/>100 | 8.9 ± 0.2 | >8.0 |
| 41 | 25 | 6.3 | >100/>100 | 7.1 ± 0.1 | >4.0 |
| 42 | 25 | 0.8 | <3.1/6.6 | 105.9 ± 1.1 | <0.1 |
| 43 | 12.5 | 0.8 | <3.1/6.4 | 105.6 ± 3.8 | <0.2 |
| 44 | 6.3 | 1.6 | 6.3/28.6 | 97.9 ± 3.7 | 1 |
| 45 | >25 | 25 | >100/>100 | 4.5 ± 0.2 | nd |
| 46 | 6.3 | 0.8 | 6.9/36.5 | 90.8 ± 2.7 | 1.1 |
| 47 | 25 | 12.5 | >100/>100 | 4.8 ± 0.2 | >4.0 |
| 48 | 12.5 | 3.1 | 25.7/48.4 | 79.9 ± 3.6 | 2.1 |

TABLE 13

| Peptoid | MIC (μM) *E. coli* ATCC 25922 | MIC (μM) *S. aureus* ATCC 25923 | $HC_{10}/HC_{50}$ (μM) | $H_{max}$ (100 μM) | Selectivity [$HC_{10}$/MIC (*E. coli*)] |
|---|---|---|---|---|---|
| 49 | >25 | >25 | >100/>100 | 0.3 ± 0.3 | nd |
| 50 | >25 | >25 | Nd | nd | nd |
| 51 | >25 | >25 | Nd | nd | nd |
| 52 | 25 | >25 | Nd | nd | nd |
| 53 | 25 | >25 | Nd | nd | nd |
| 54 | 25 | >25 | Nd | nd | nd |
| 55 | 25 | >25 | Nd | nd | nd |
| 56 | 25 | 25 | Nd | nd | nd |
| 57 | 25 | 12.5 | Nd | nd | nd |

TABLE 13-continued

| Peptoid | MIC (μM) E. coli ATCC 25922 | S. aureus ATCC 25923 | $HC_{10}/HC_{50}$ (μM) | $H_{max}$ (100 μM) | Selectivity [$HC_{10}$/MIC (*E. coli*)] |
|---|---|---|---|---|---|
| 58 | 25 | 12.5 | Nd | nd | nd |
| 59 | >25 | 25 | Nd | nd | nd |
| 60 | >25 | 12.5 | Nd | nd | nd |
| 61 | 6.3 | 3.1 | 19.3/65.4 | 79.9 ± 0.7 | 3.1 |
| 62 | 6.3 | 3.1 | 36.2/>100 | 44.8 ± 8.1 | 5.7 |
| 63 | 12.5 | 3.1 | 85.0/>100 | 12.7 ± 0.9 | 6.8 |
| 64 | 12.5 | 3.1 | 70.7/>100 | 18.9 ± 2.9 | 5.7 |
| 65 | >25 | >25 | Nd | nd | nd |
| 56 | >25 | >25 | Nd | nd | nd |

Analysis Example 6: Confirmation of Antimicrobial Activity of Peptoid in Multidrug-Resistant Bacteria The MIC of the prepared peptoid in multidrug-resistant bacteria was measured using a modified microdilution method in a Difco Mueller Hinton medium, and a test was performed on a bacterial pathogen panel with resistant and tolerance to general antibiotics.

Briefly, a medium containing bovine serum albumin and 0.001% acetic acid was used to continuously dilute a peptoid concentrate 10-times stronger than the final concentration. 10 μL of the 10-time stronger peptoid concentrate and 90 μL of a Muleller Hinton medium were added to each well of a 96-well plate. Bacteria were added to the plate until the final concentration reached $2\times10^5$ CFU/mL and then incubated at 3 °C overnight. MIC was defined as a concentration at which bacterial growth is not observed.

In the following Table 14, the antimicrobial activity of a peptoid against multidrug-resistant bacteria is shown. Similar to the antimicrobial activities against the gram-negative bacteria, *E. coli* ATCC 25922, and the gram-positive bacteria, *S. aureus* ATCC 25923, Peptoid 1 showed a relatively low MIC against multidrug-resistant bacteria. The antimicrobial peptoid of the present inventive concept showed an MIC against gram-negative bacteria, such as *Enterobacter* SP KCTC 2625 and *E. coli* KCTC 2411, which is similar to that of Peptoid 1. Meanwhile, for the gram-positive bacteria, *Enterococcus Faecium* KCTC 13225 and *Enterococcus faecalis* KCTC 3511, a relatively high MIC was confirmed in the peptoid of the present inventive concept, compared to Peptoid 1.

TABLE 14

| Peptoid Peptoid | Enterobacter SP KCTC 2625 | *Enterococcus Faecium* KCTC 13225 | *Enterococcus faecalis* KCTC 3511 | *E. coli* KCTC 2411 | *P. aeruginosa* KCTC 1637 |
|---|---|---|---|---|---|
| 1 | 6.3 | <0.8 | 0.8 | 6.3 | 25 |
| 11 | 6.3 | <0.8 | <0.8 | 12.5 | — |
| 14 | 3.1 | <0.8 | 1.6 | 6.3 | — |
| 29 | 3.1 | 1.6 | 3.1 | 6.3 | 50 |
| 32 | 3.1 | 3.1 | 6.3 | 6.3 | 25 |

Analysis Example 7: Analysis of Antimicrobial Activity Against *E. coli* According to Number and Substitution Position of NhTrp FIGS. 5 and 6 are graphs that analyze the antimicrobial activity against *E. coli* according to the number and substitution position of NhTrp of peptoids according to one embodiment of the present inventive concept.

Figure 5:
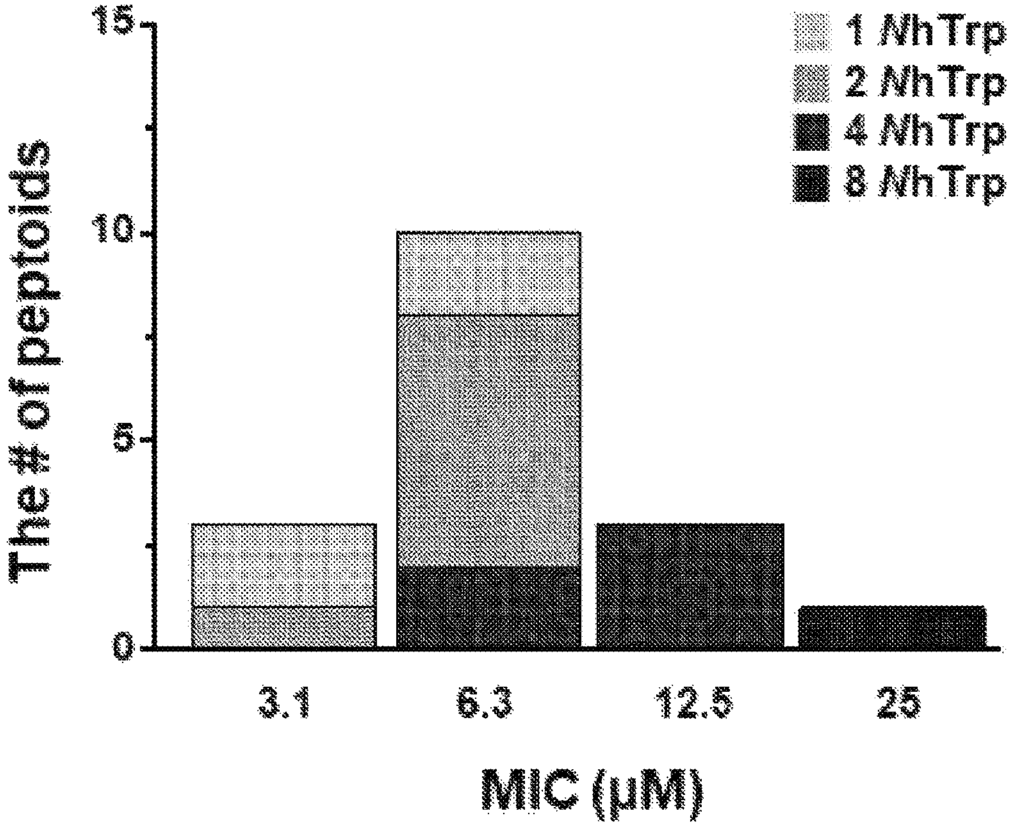
FIGS. 5 and 6 are graphs analyzing the antimicrobial activity against *E. coli* according to the substitution number and position of NhTrp of an antimicrobial peptoid according to one embodiment of the present inventive concept.
Figure 6:
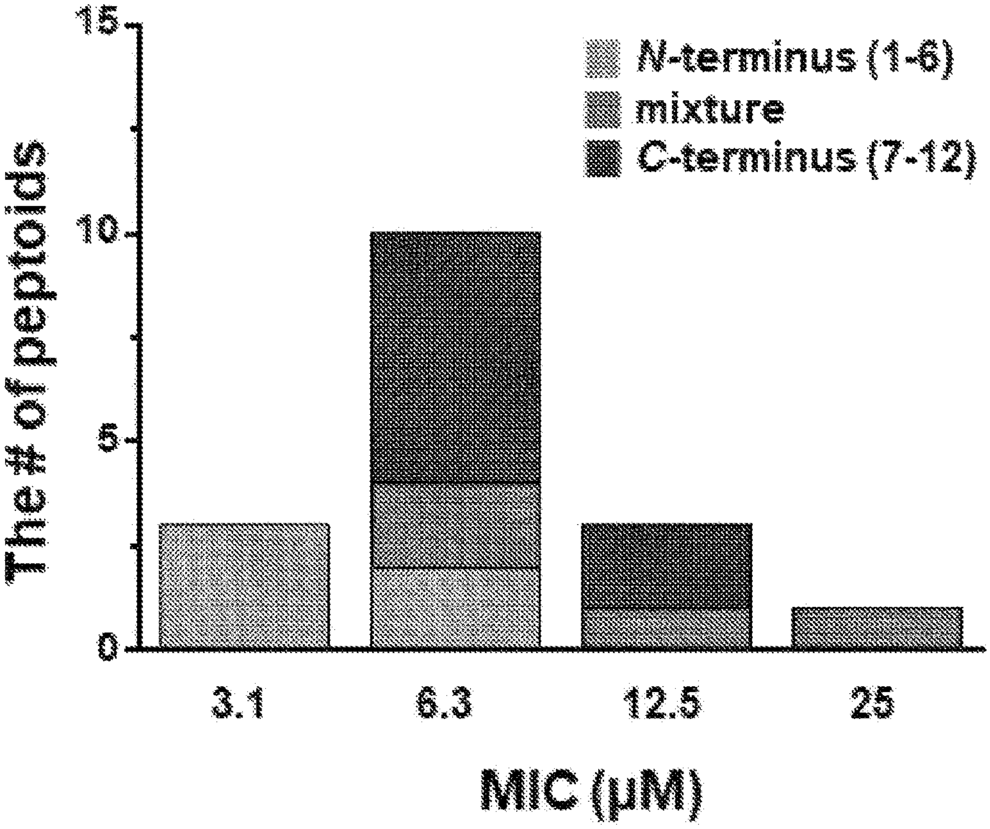

Referring to FIG. 5, for Peptoids 7 to 23 prepared according to one embodiment of the present inventive concept, MIC values against *E. coli* according to the number of substitutions of NhTrp of the peptoids are shown. Accordingly, the tendency to have a relatively low MIC value was confirmed in a peptoid with a small number of NhTrp substitutions. In addition, referring to FIG. 6, for Peptoids 1 to 41 prepared according to an embodiment of the present inventive concept, MIC values for each NhTrp substitution position of the peptoids are shown. According to this, it was confirmed that a peptoid in which NhTrp is substituted at the N-terminus position, rather than the C-terminus position, tends to have a relatively lower MIC value. Accordingly, it can be seen that a novel peptoid in which NhTrp is less substituted at the N-terminus position of the present inventive concept exhibits effective antimicrobial activity.

Analysis Example 8: Analysis of Correlation Between HPLC Elution and Antimicrobial Activity and Red Blood Cell Toxicity FIGS. 7 and 8 are graphs that analyze the relationship between the HPLC elution, and antimicrobial activity and red blood cell toxicity of a peptoid according to an embodiment of the present inventive concept.

Figure 7:
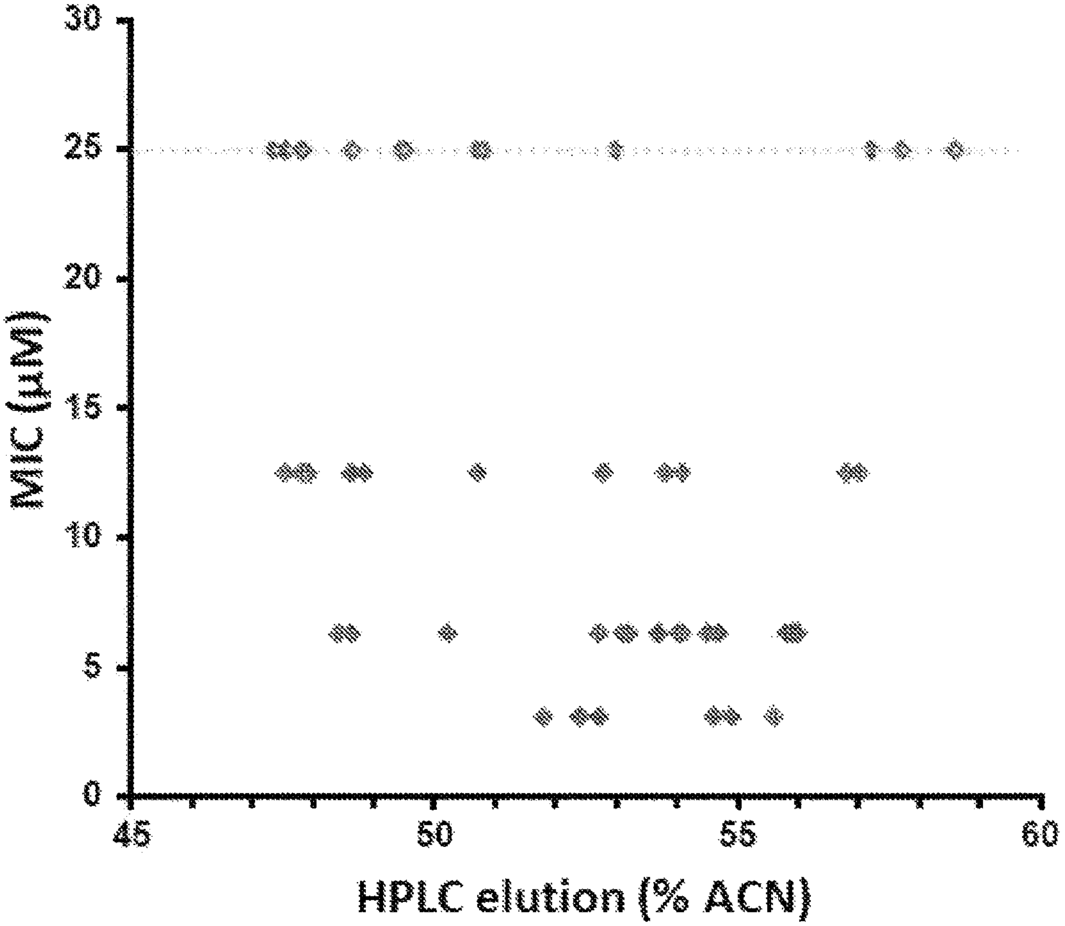
FIGS. 7 and 8 are graphs analyzing the relationships between the HPLC elution and the antimicrobial activity and the red blood cell toxicity of an antimicrobial peptoid according to one embodiment of the present inventive concept.
Figure 8:
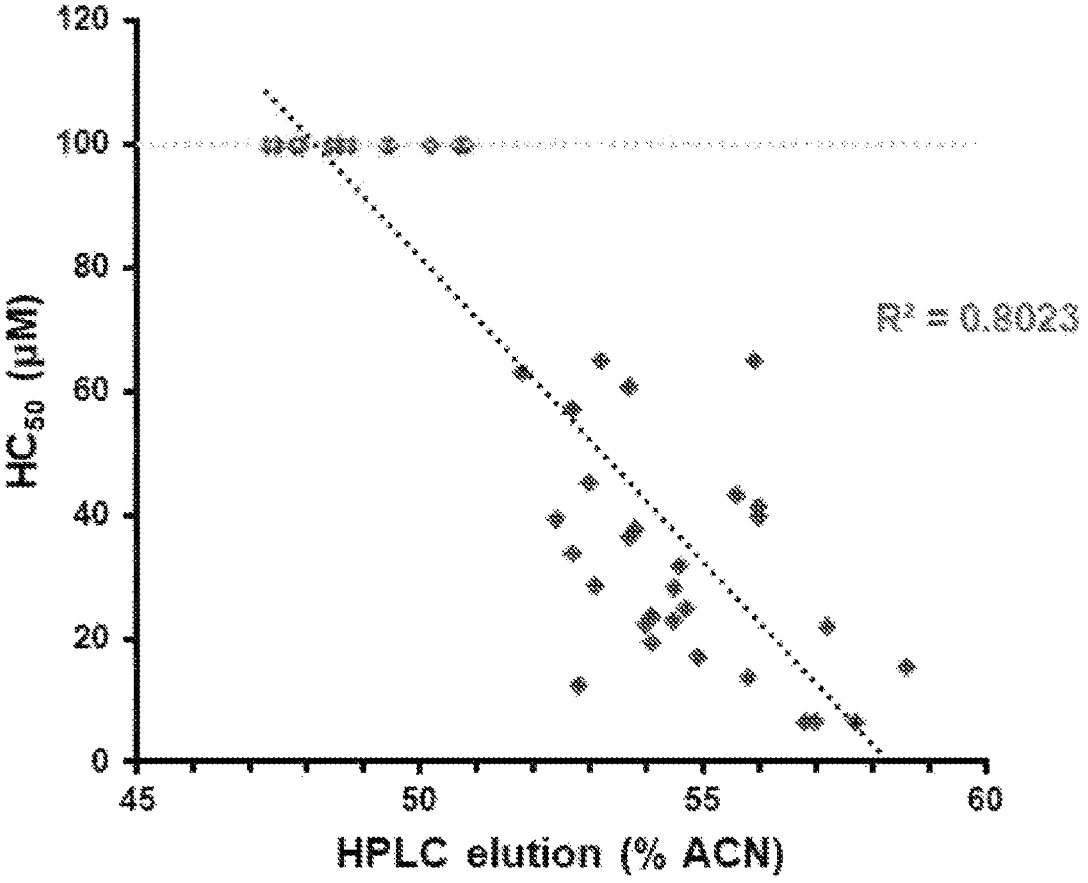

Referring to FIGS. 7 and 8, the antimicrobial activity against *E. coli* was not significantly correlated with hydrophobicity. However, in the results for red blood cell toxicity, an $HC_{50}$ value tended to decrease as the HPLC elution amount of ACN increased. Accordingly, it can be seen that, in the case of a peptoid with an increased cationic charge although having a hydrophobic residue, the lower the HPLC elution of the peptoid, the lower the cytotoxicity.

Analysis Example 9: HPLC and LC-MS Analysis

Figure 9:
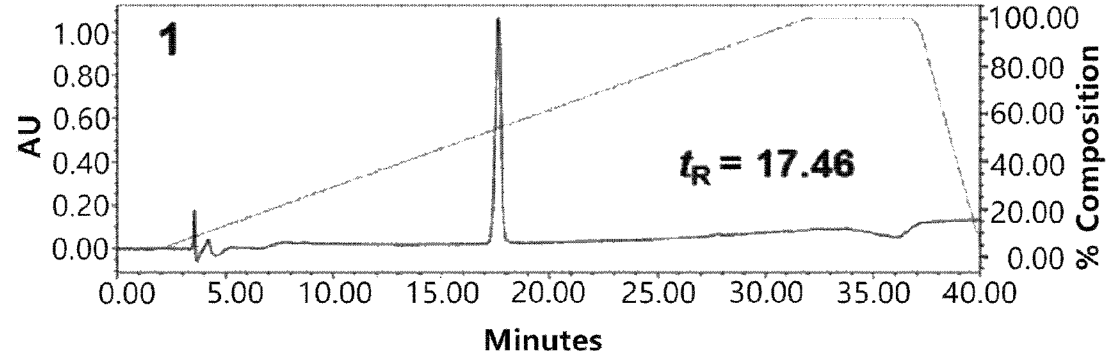
FIGS. 9 to 74 are the HPLC analysis results for antimicrobial Peptoids 1 to 66 according to one embodiment of the present inventive concept.
Figure 10:
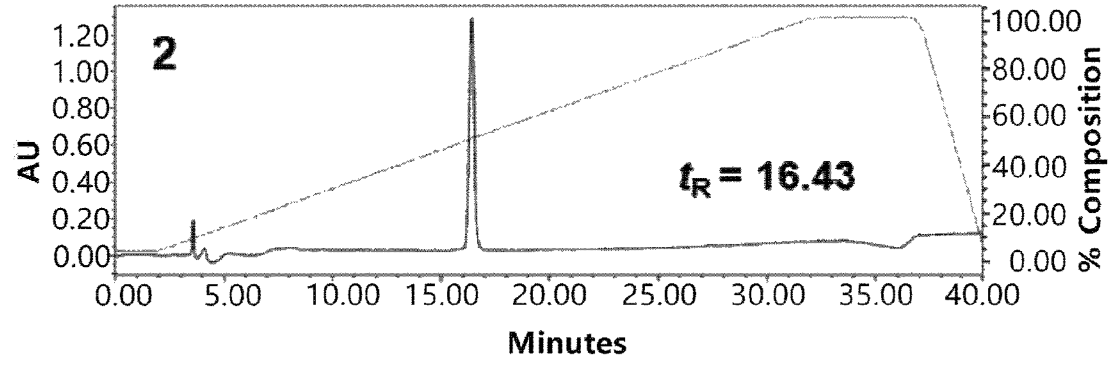
Figure 11:
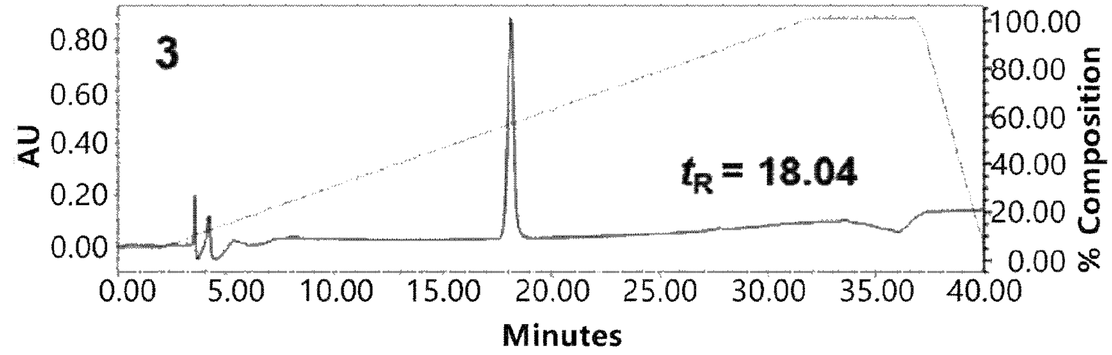
Figure 12:
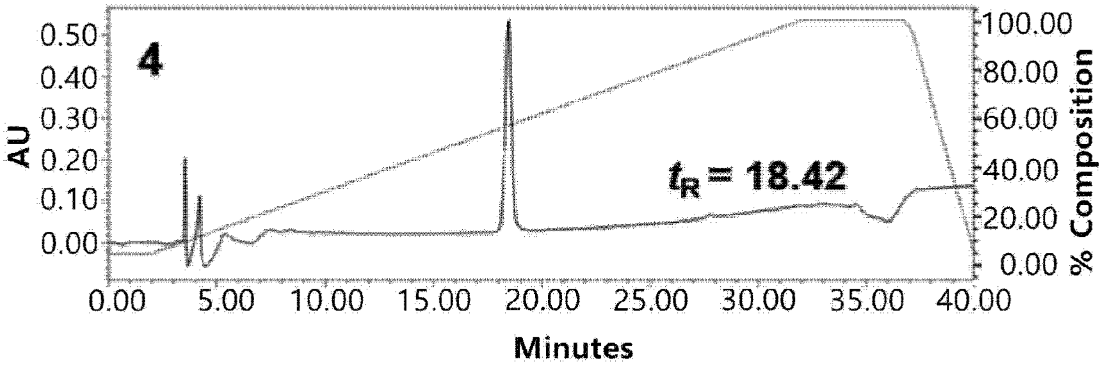
Figure 13:
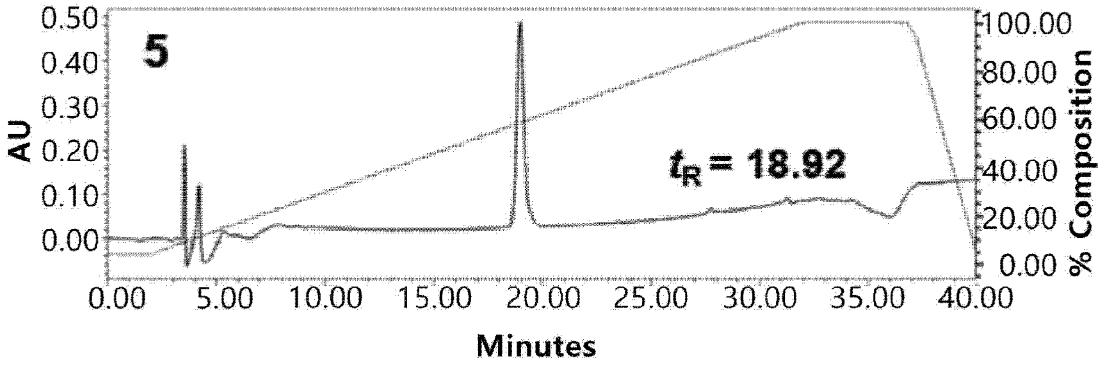
Figure 14:
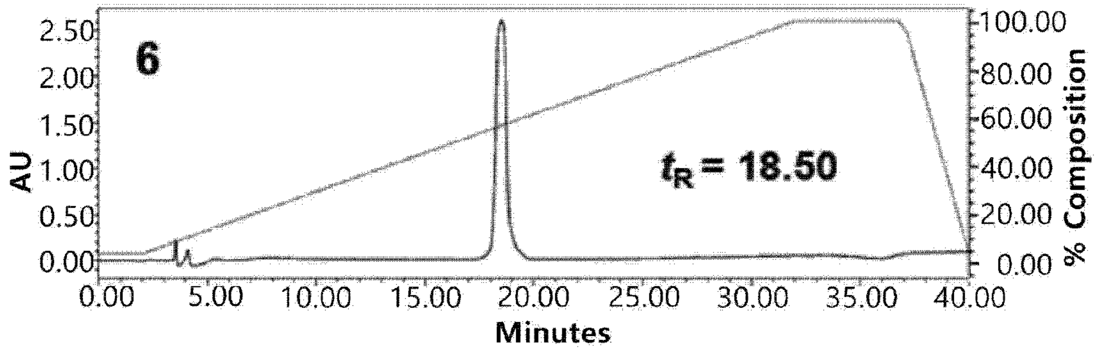
Figure 15:
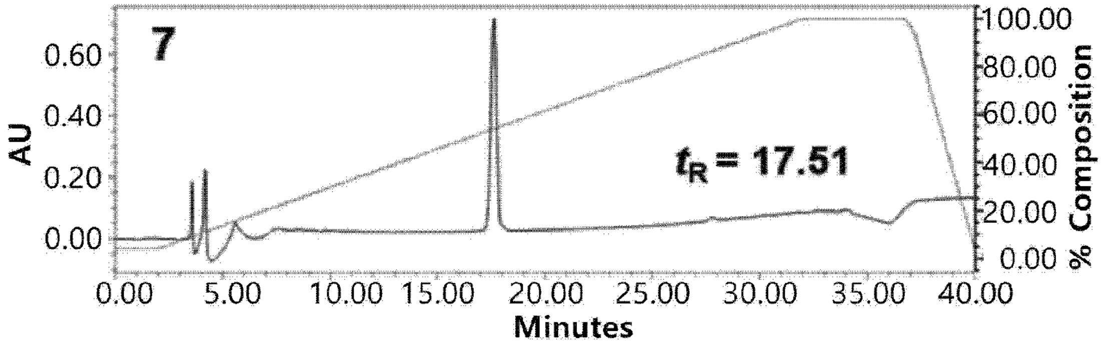
Figure 16:
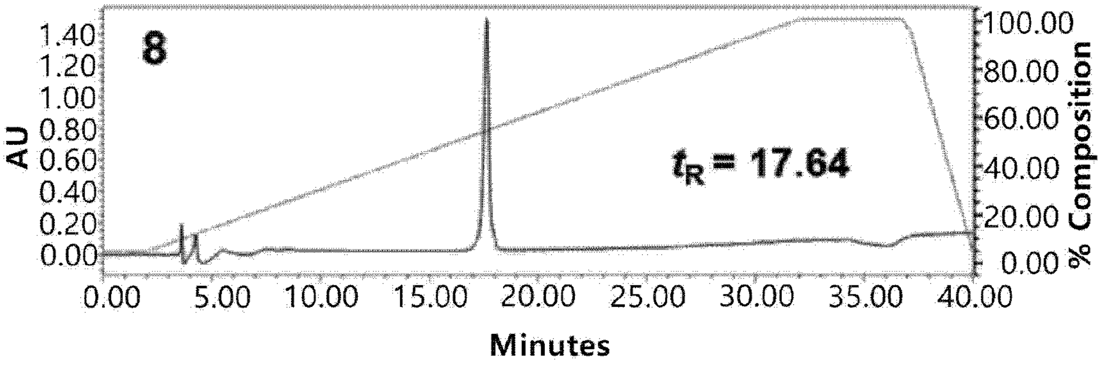
Figure 17:
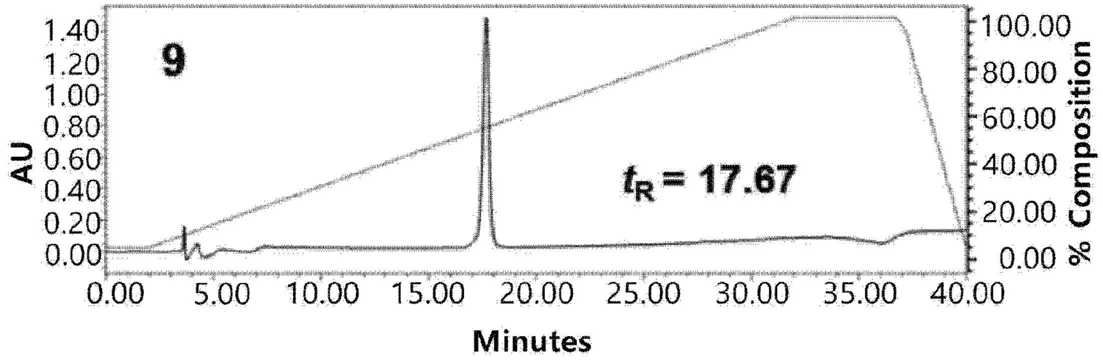
Figure 18:
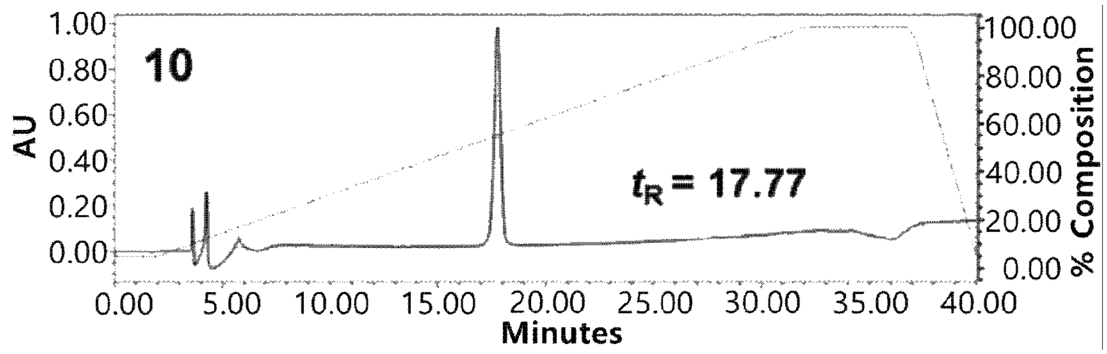
Figure 19:
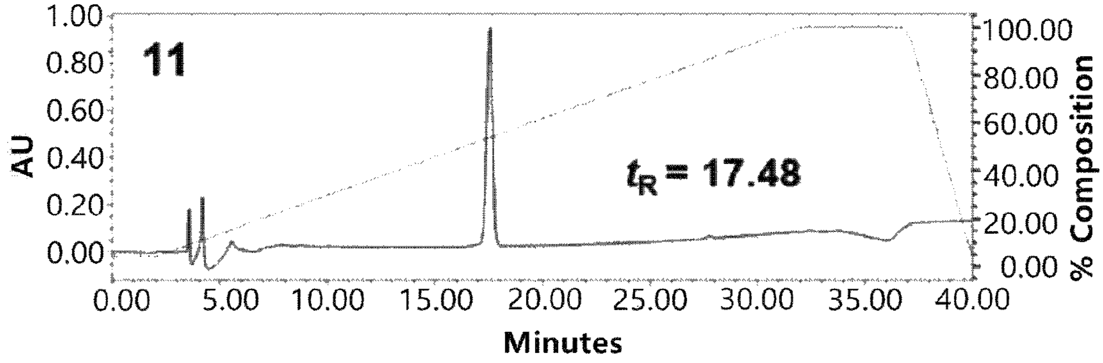
Figure 20:
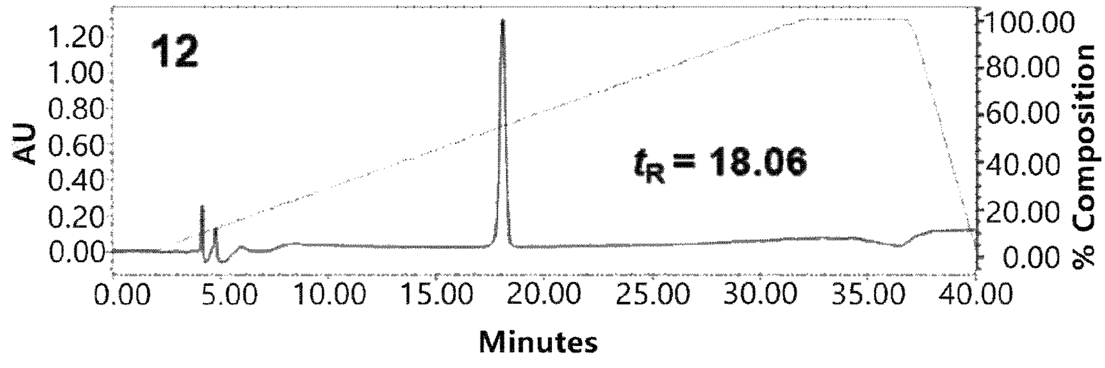
Figure 21:
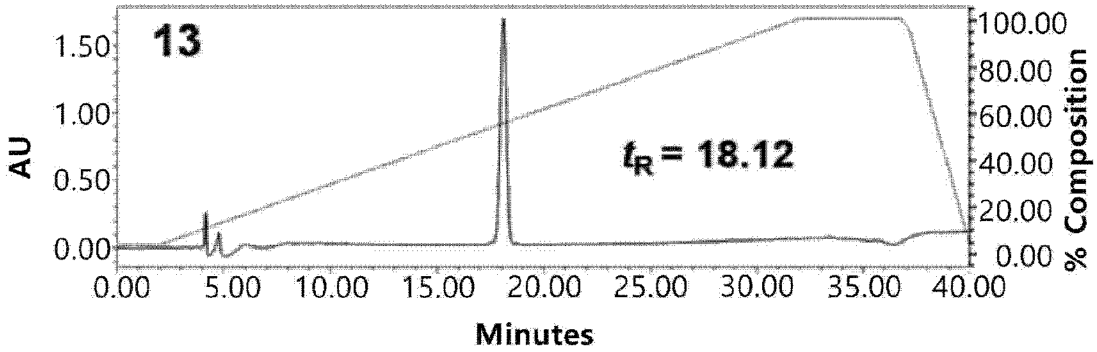
Figure 22:
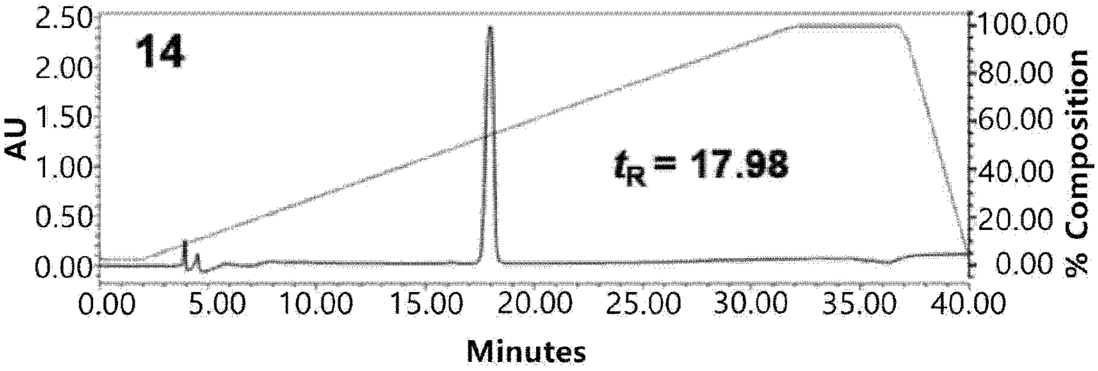
Figure 23:
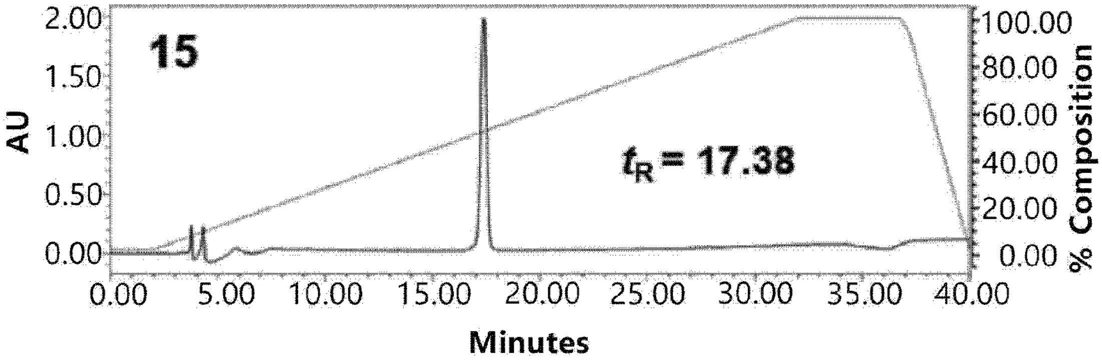
Figure 24:
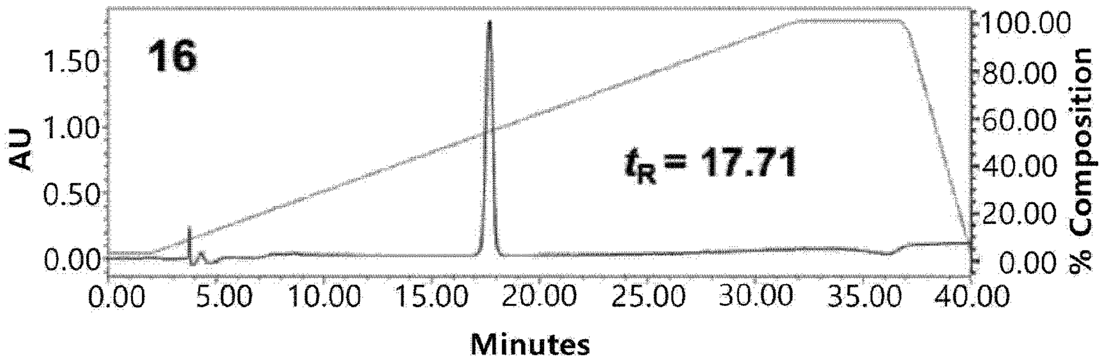
Figure 25:
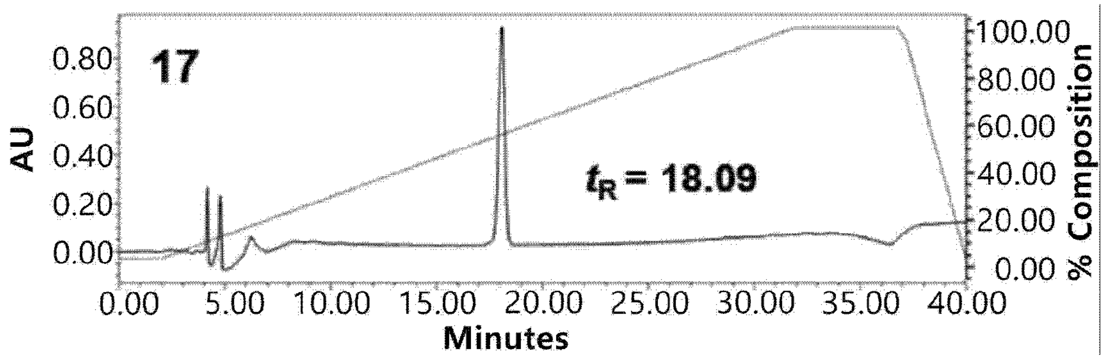
Figure 26:
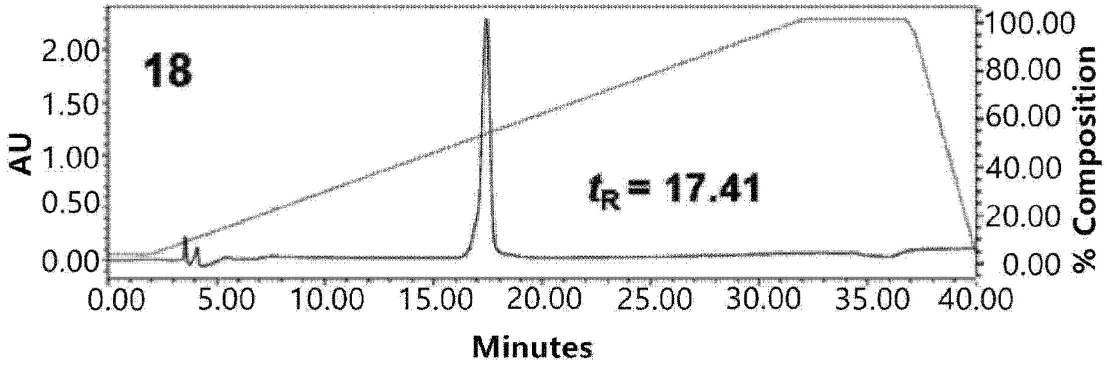
Figure 27:
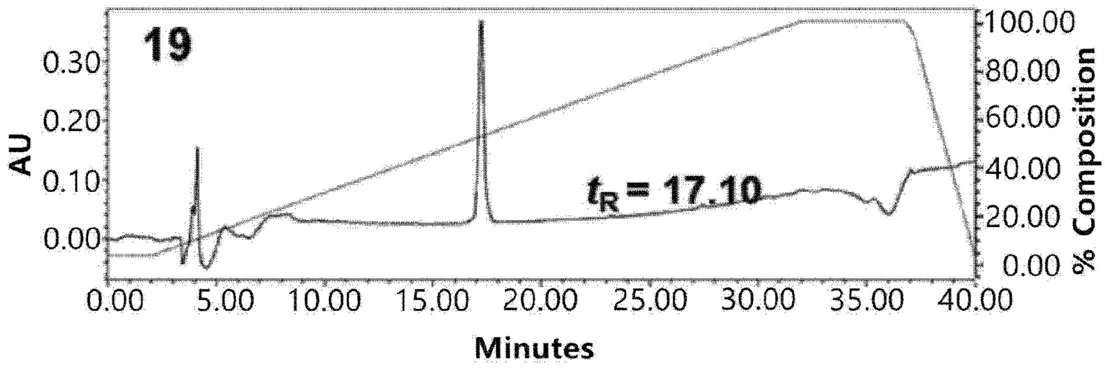
Figure 28:
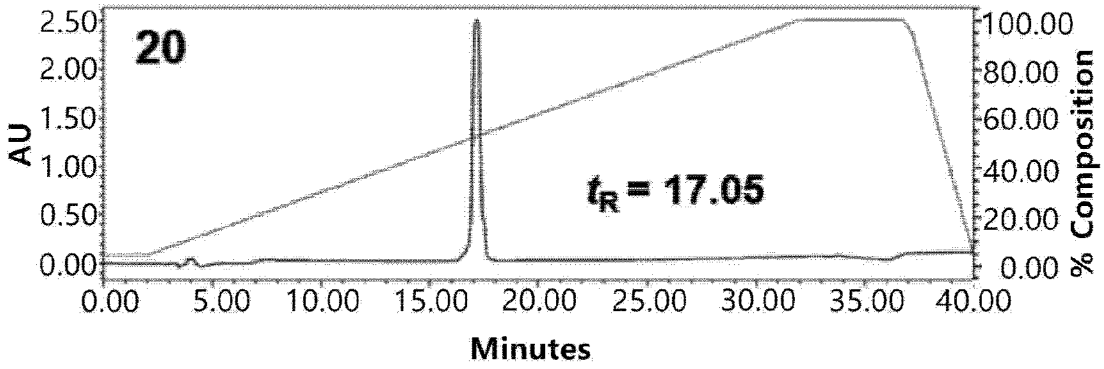
Figure 29:
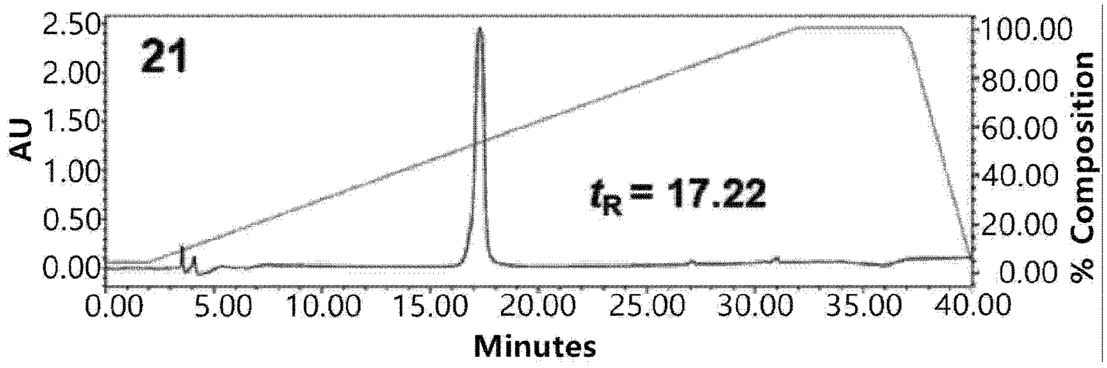
Figure 30:
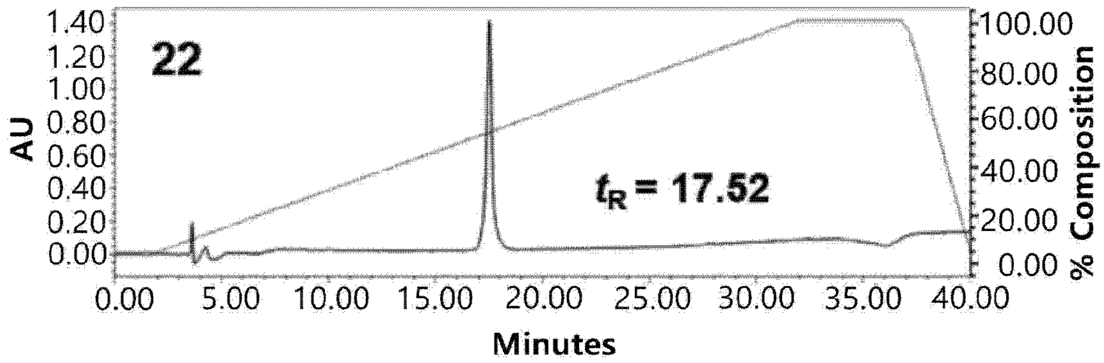
Figure 31:
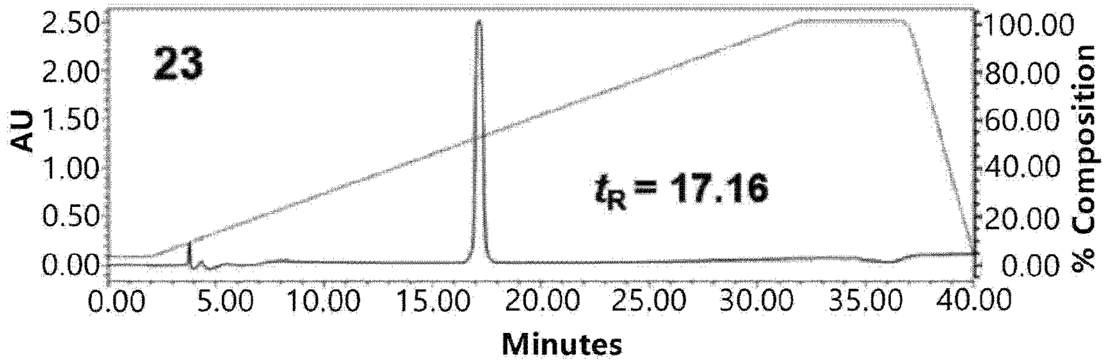
Figure 32:
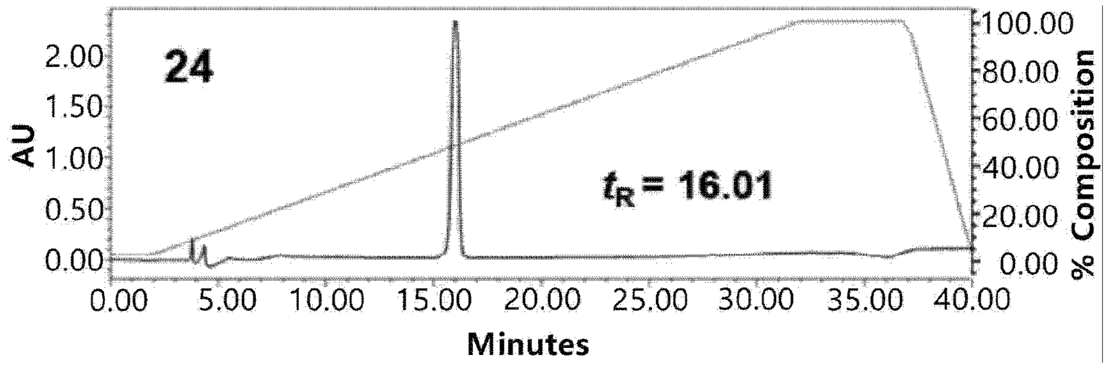
Figure 33:
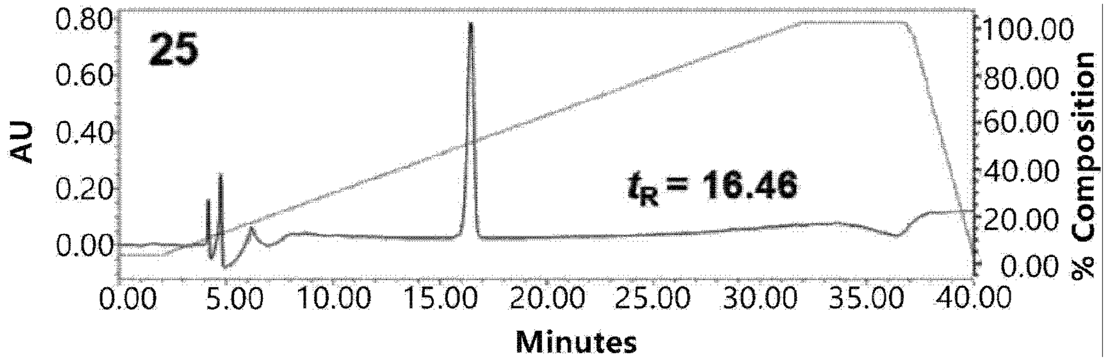
Figure 34:
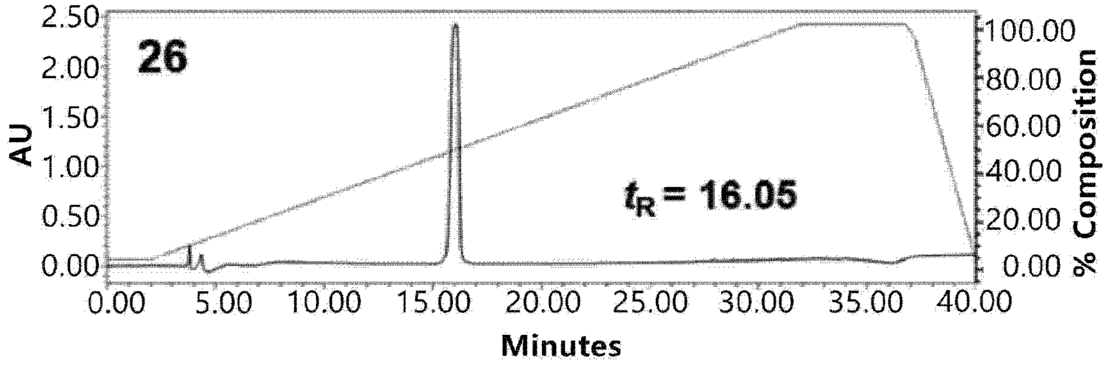
Figure 35:
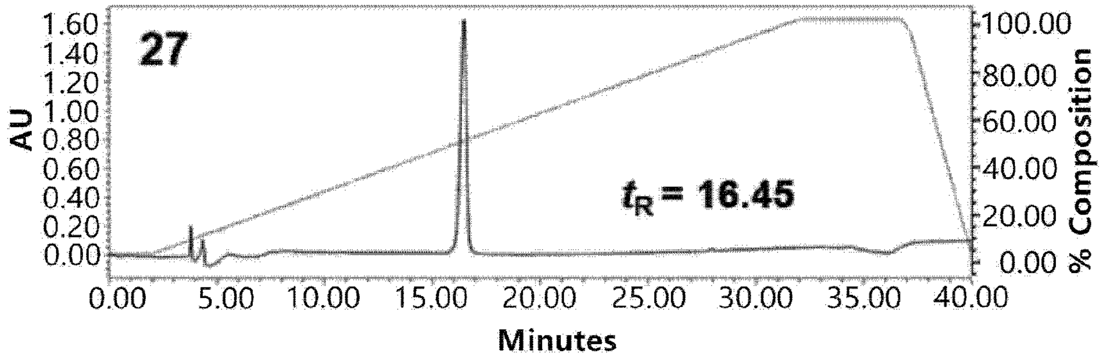
Figure 36:
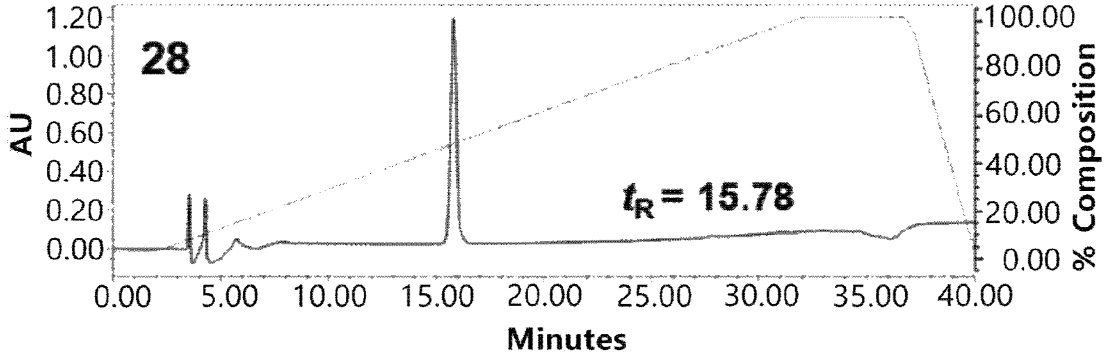
Figure 37:
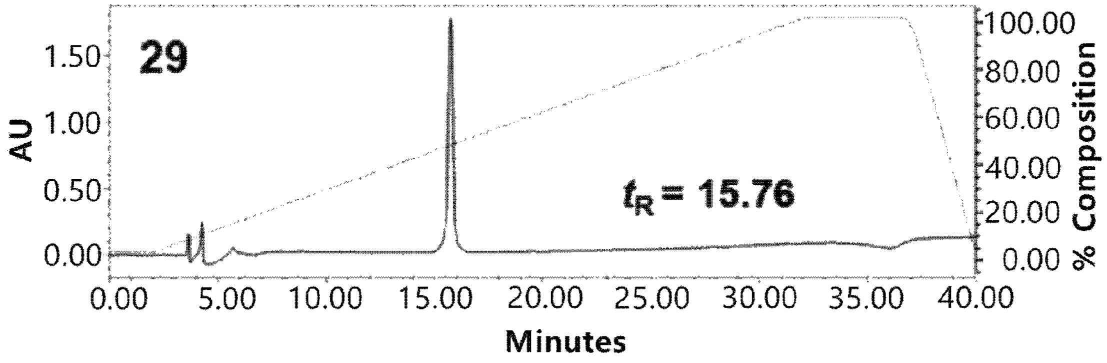
Figure 38:
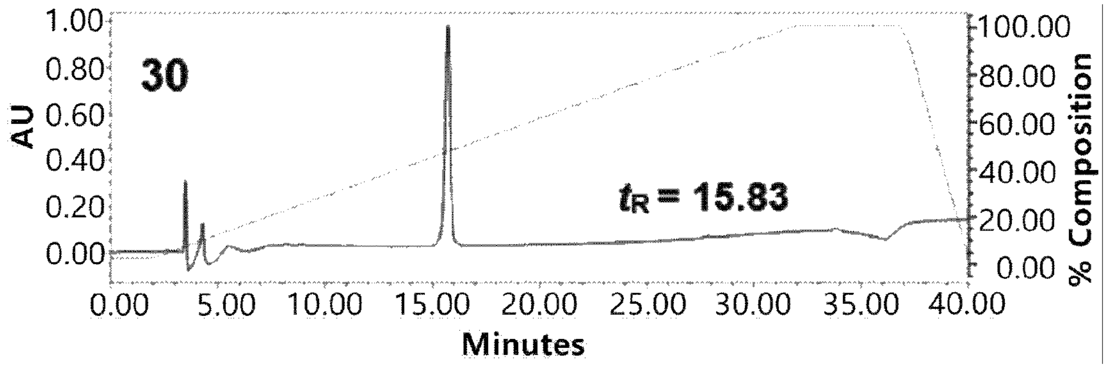
Figure 39:
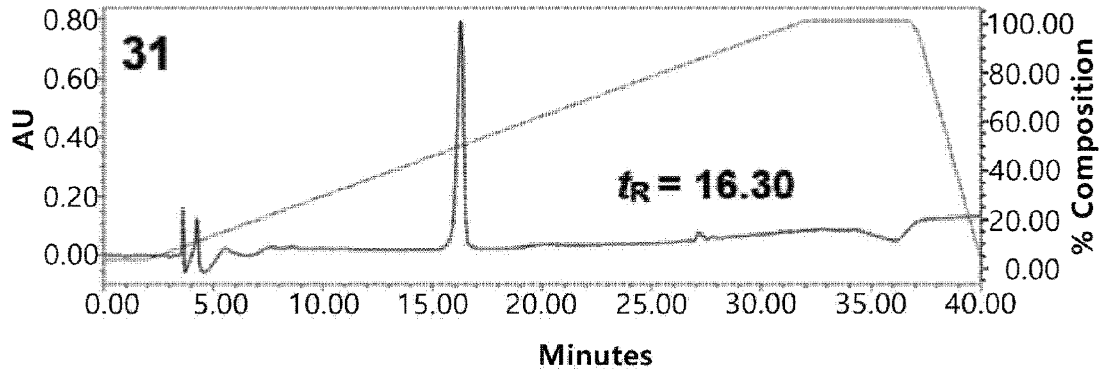
Figure 40:
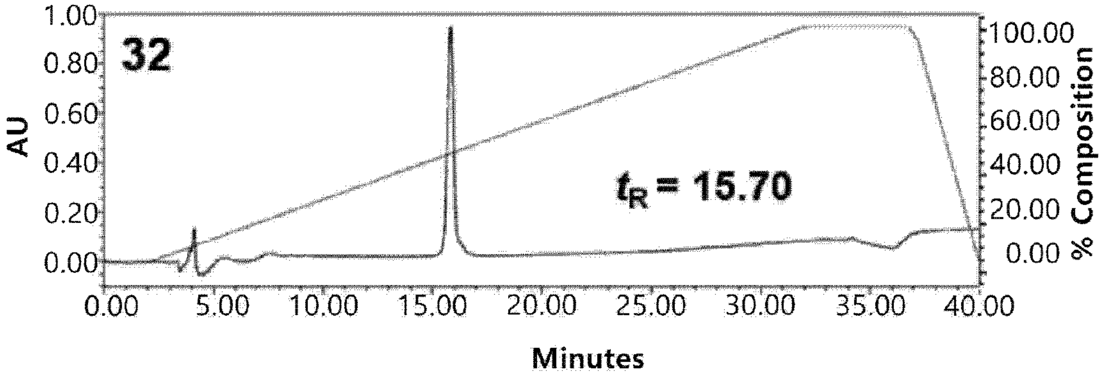
Figure 41:
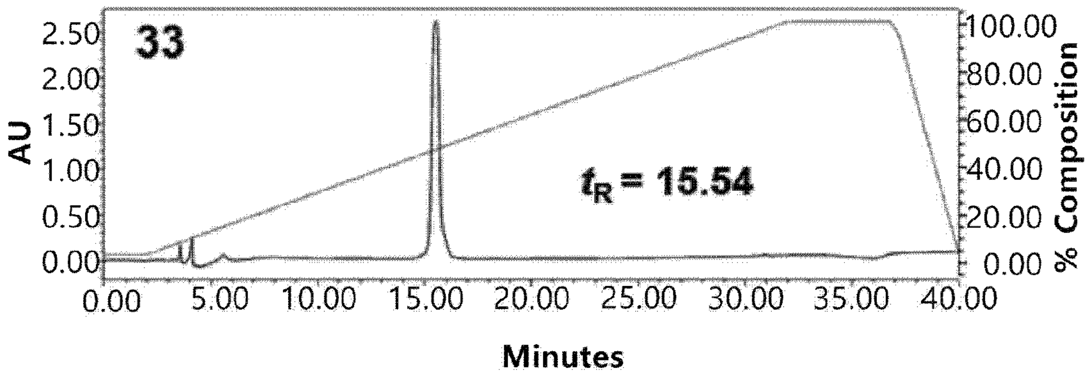
Figure 42:
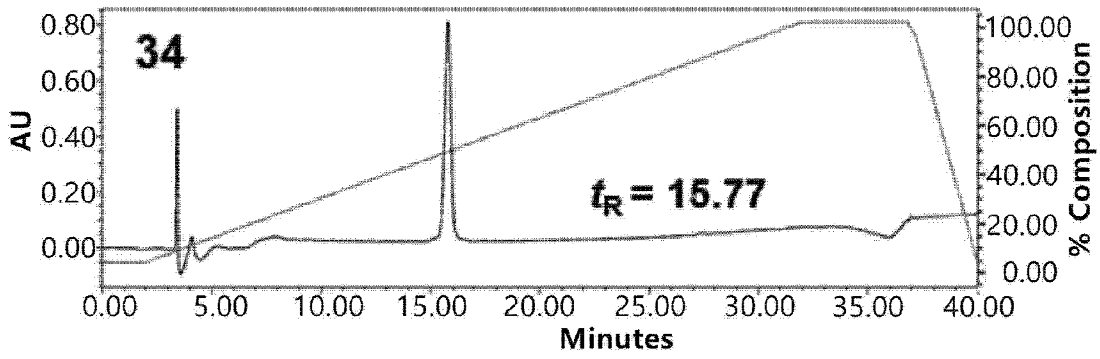
Figure 43:
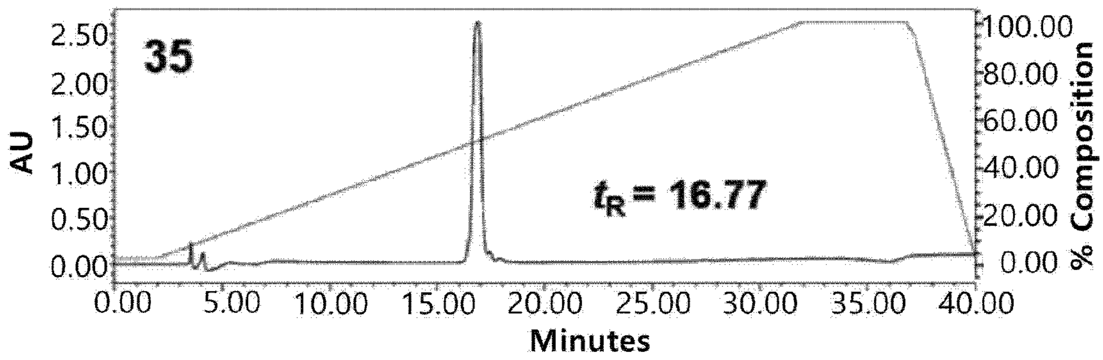
Figure 44:
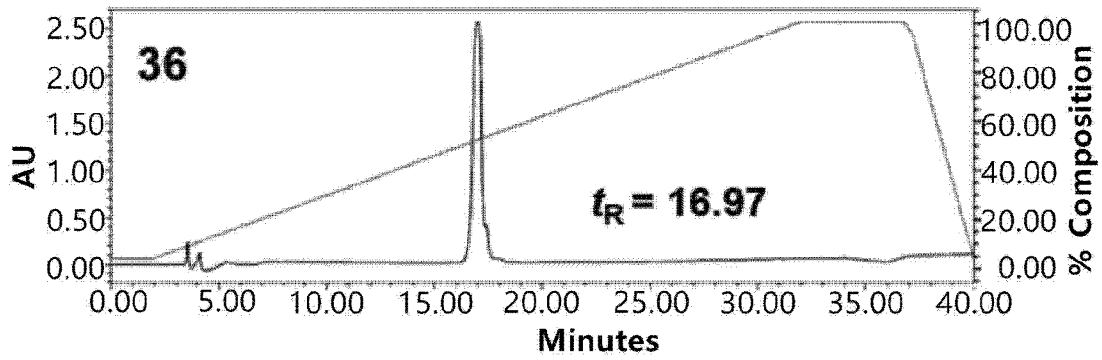
Figure 45:
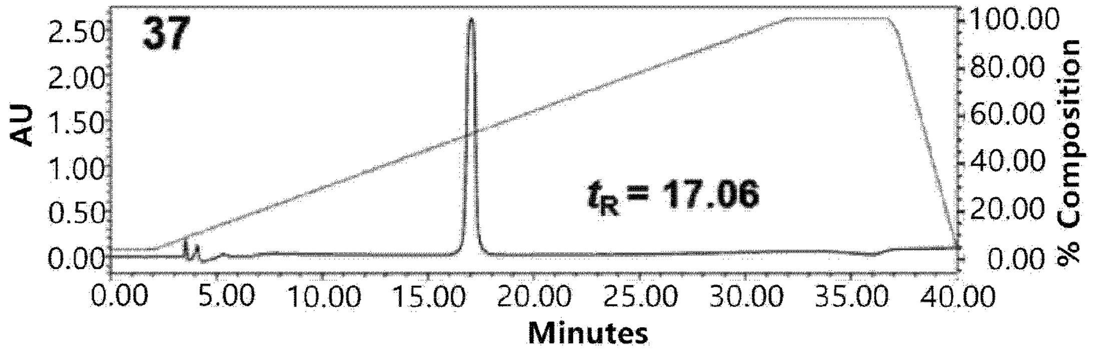
Figure 46:
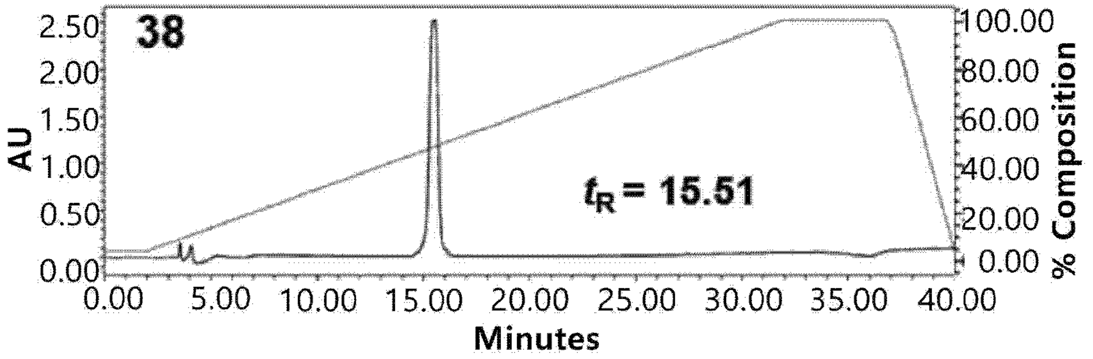
Figure 47:
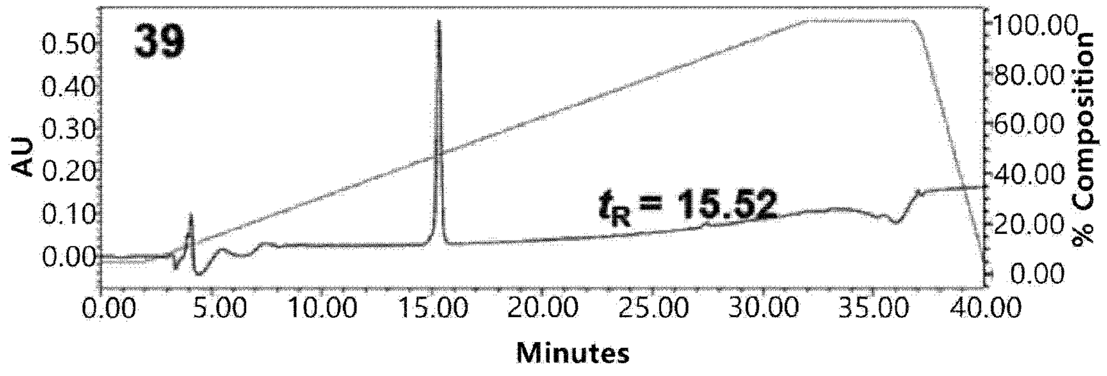
Figure 48:
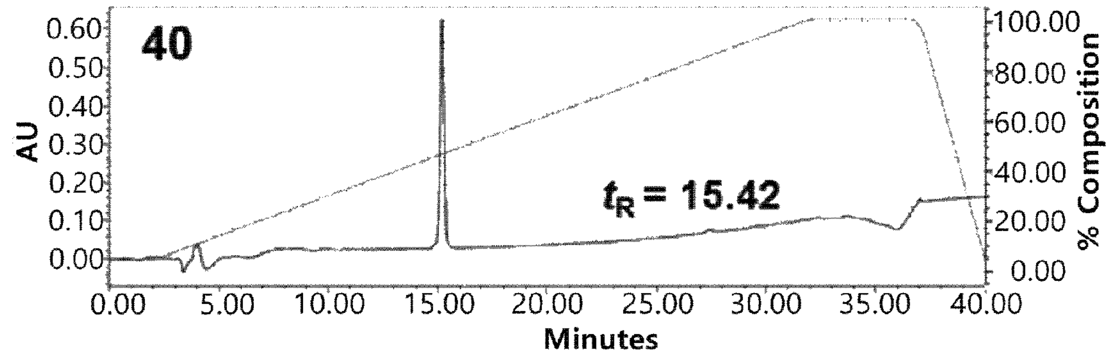
Figure 49:
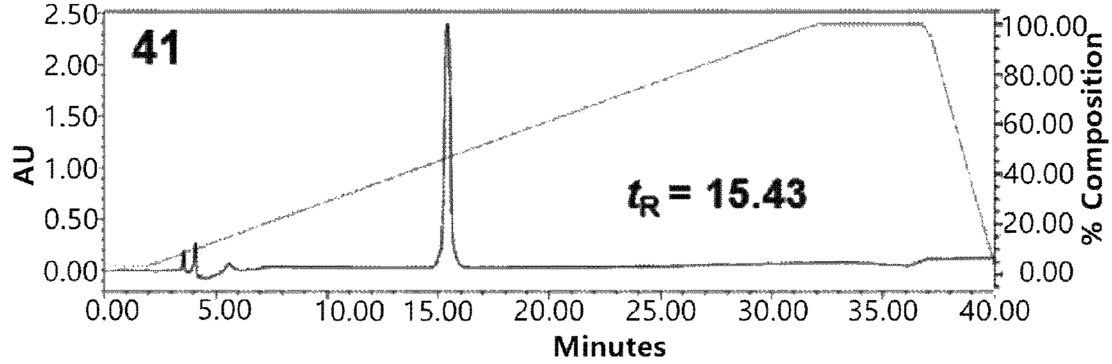
Figure 50:
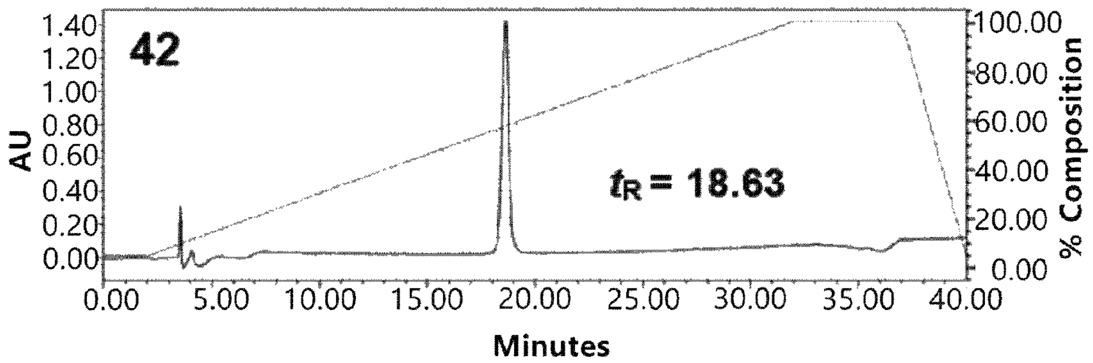
Figure 51:
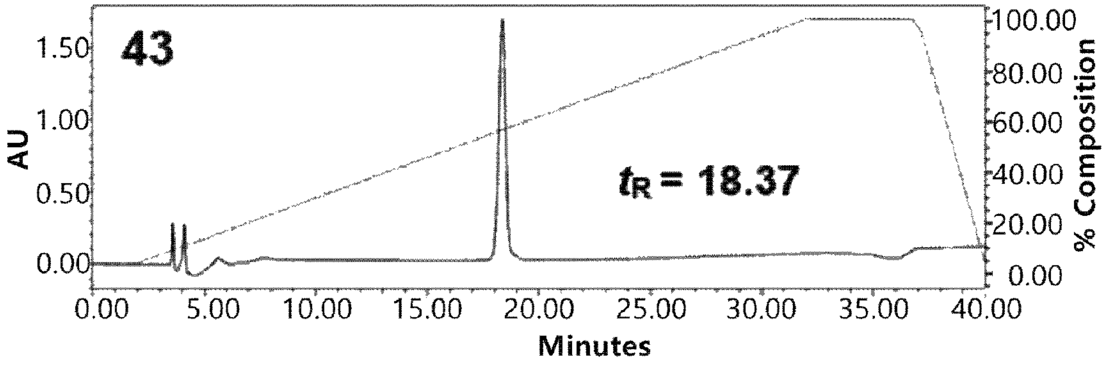
Figure 52:
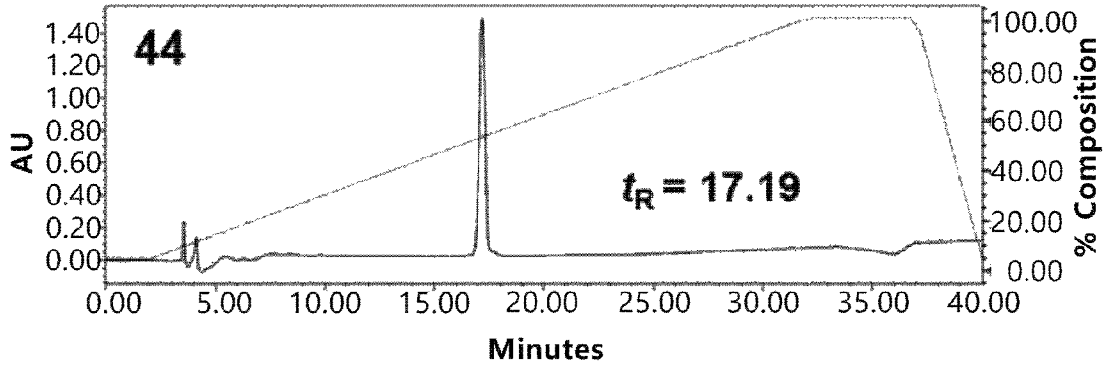
Figure 53:
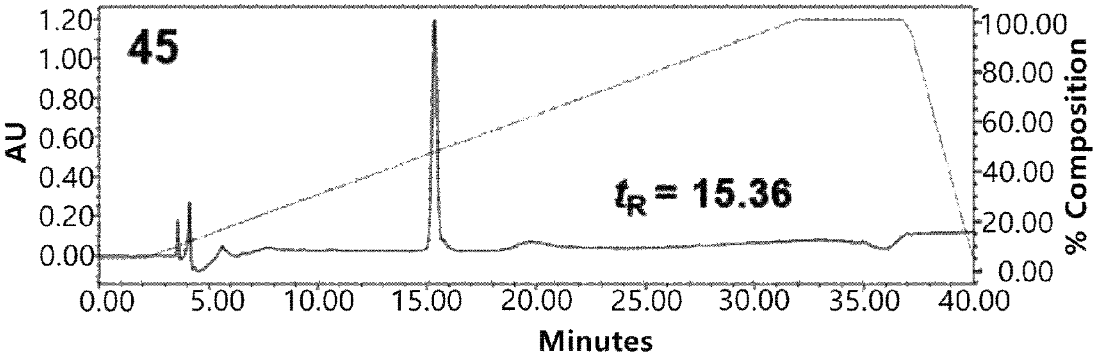
Figure 54:
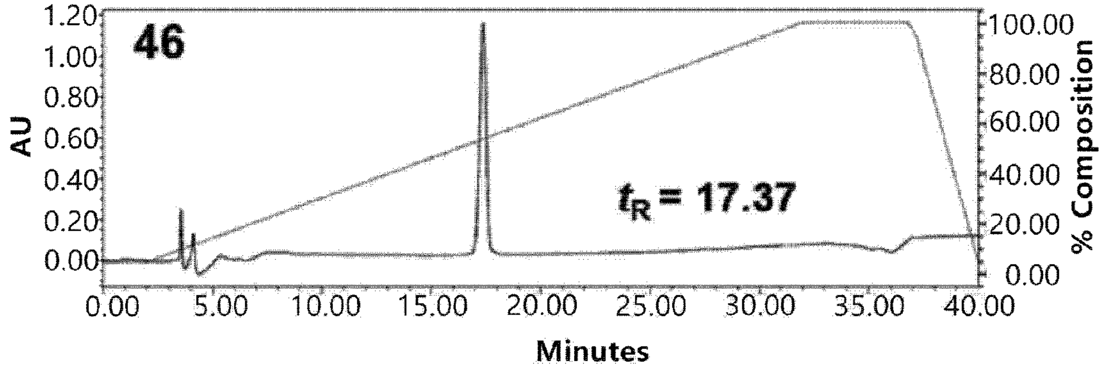
Figure 55:
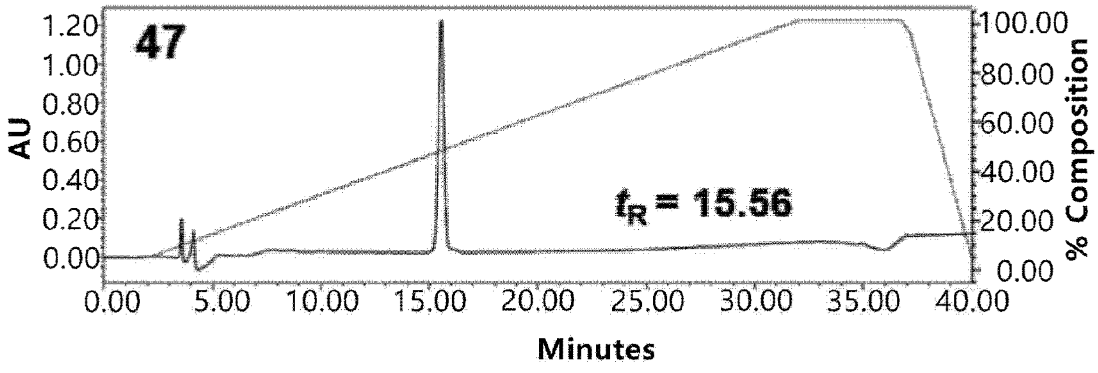
Figure 56:
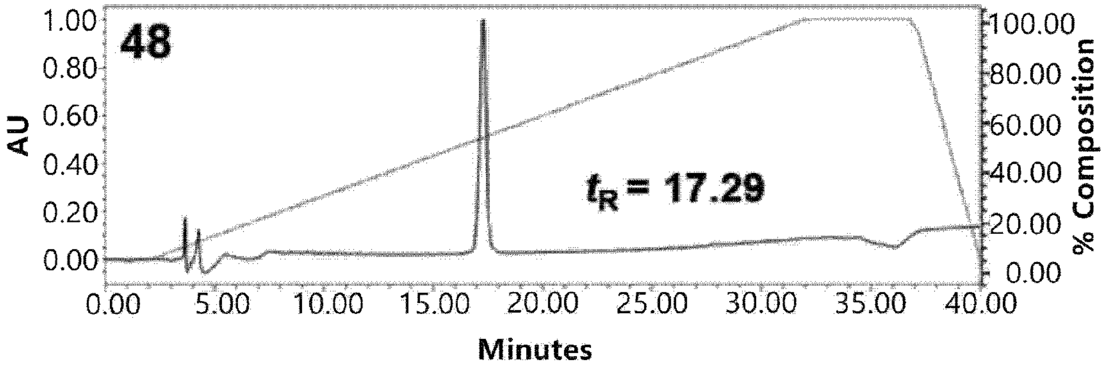
Figure 57:
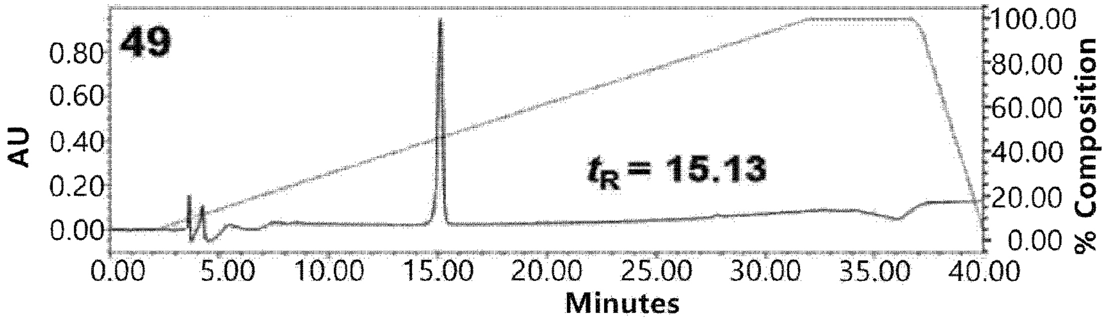
Figure 58:
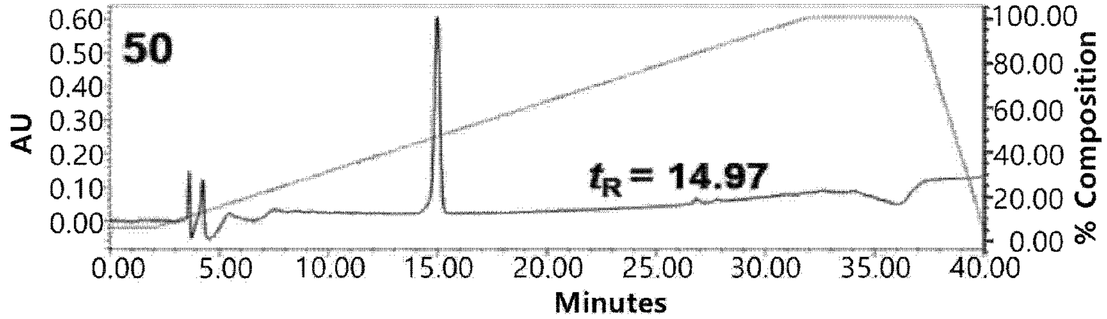
Figure 59:
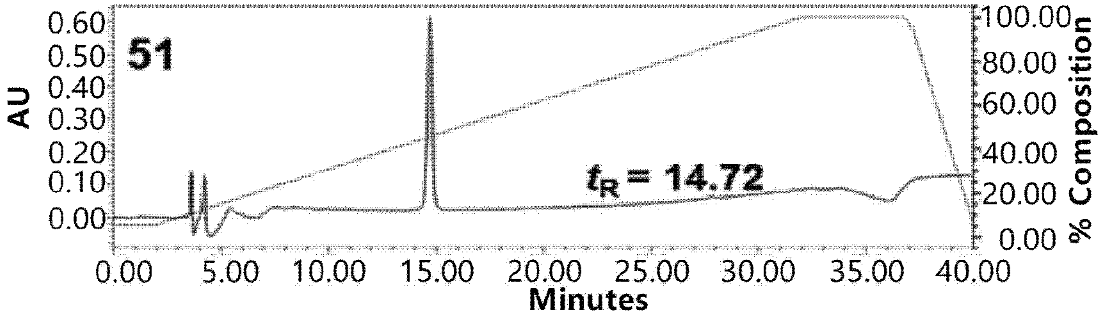
Figure 60:
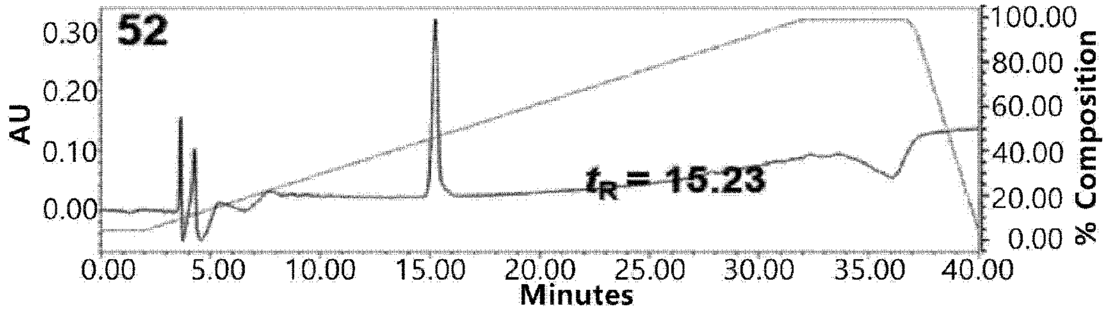
Figure 61:
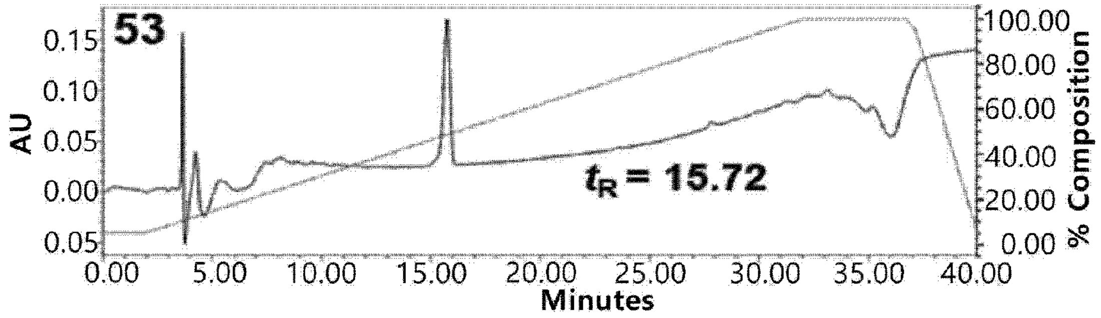
Figure 62:
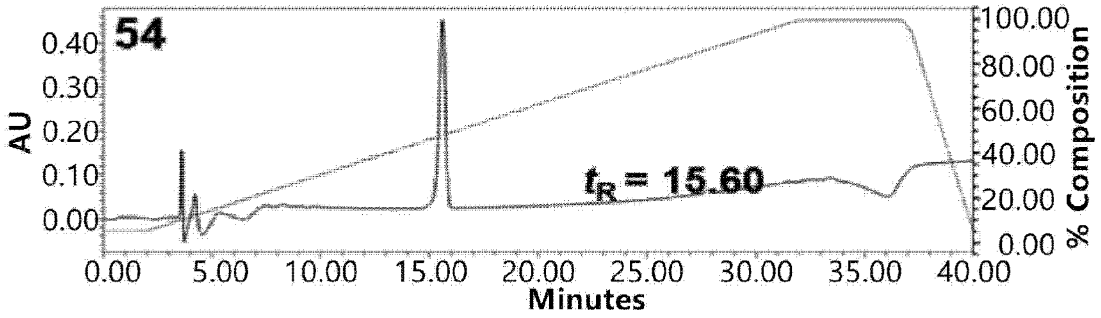
Figure 63:
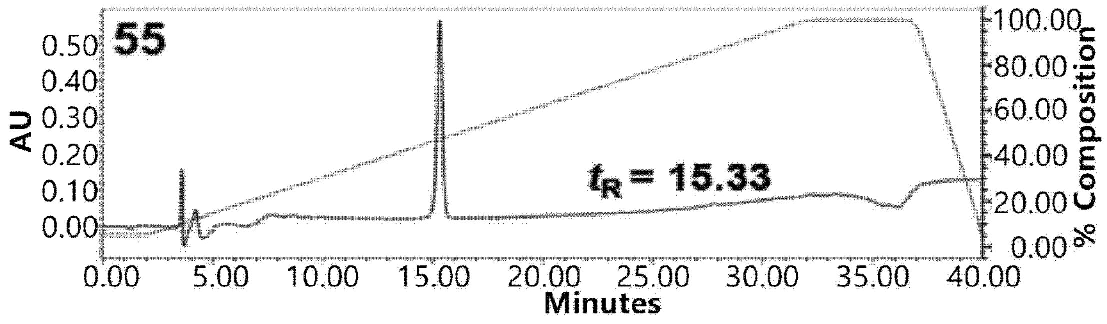
Figure 64:
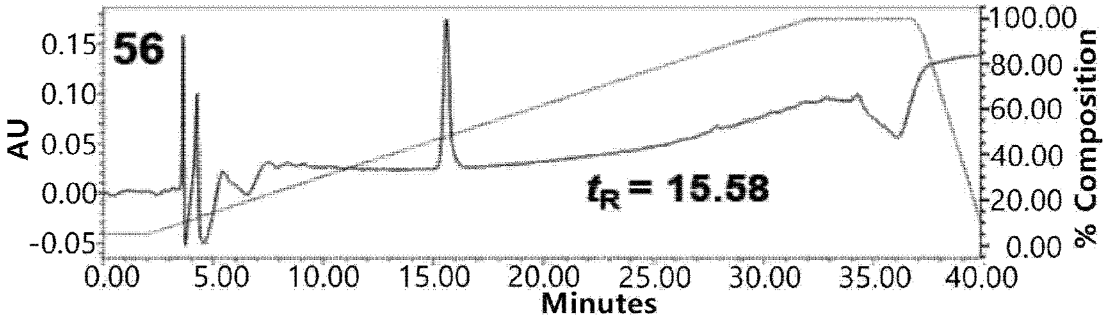
Figure 65:
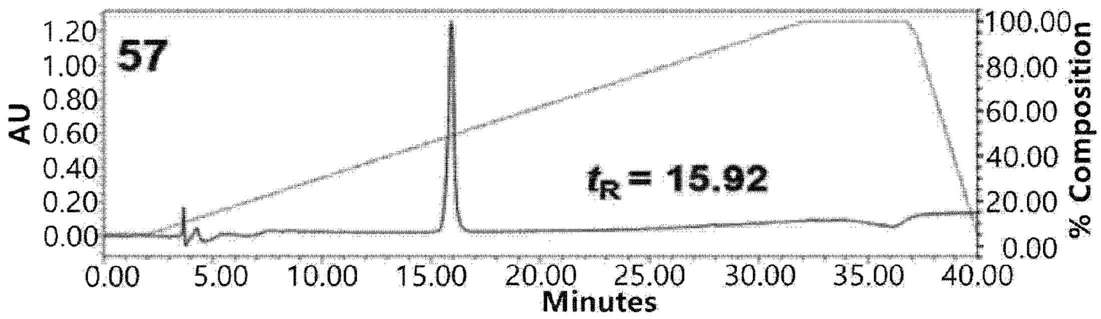
Figure 66:
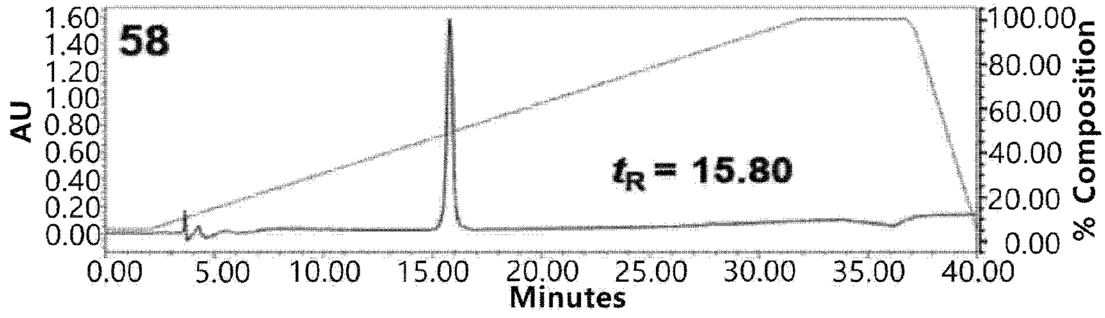
Figure 67:
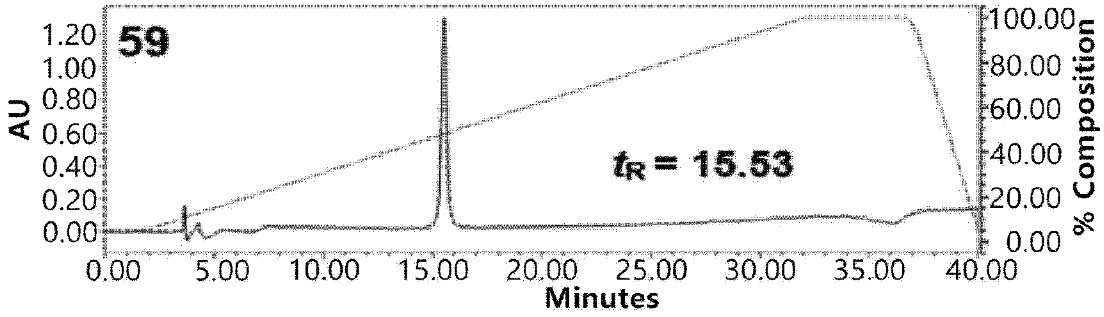
Figure 68:
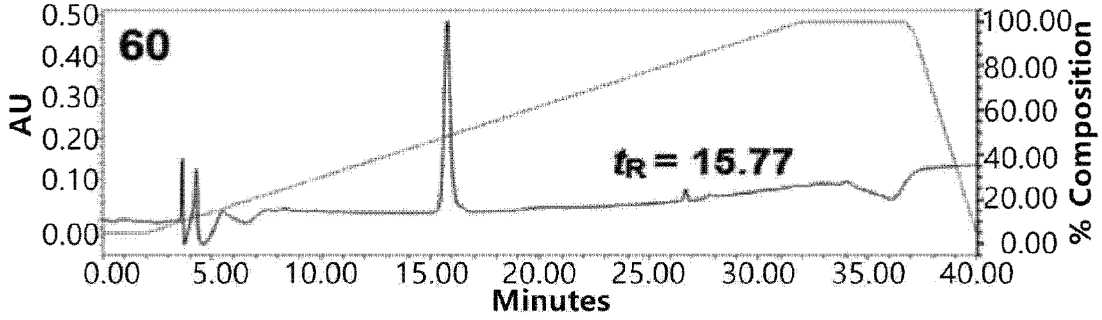
Figure 69:
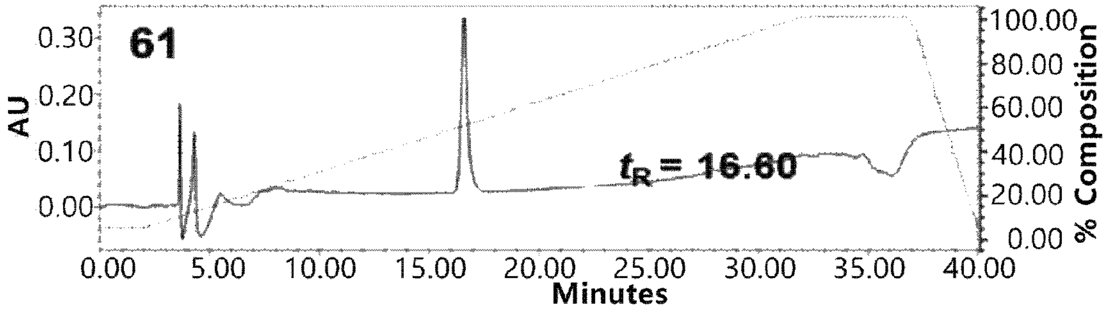
Figure 70:
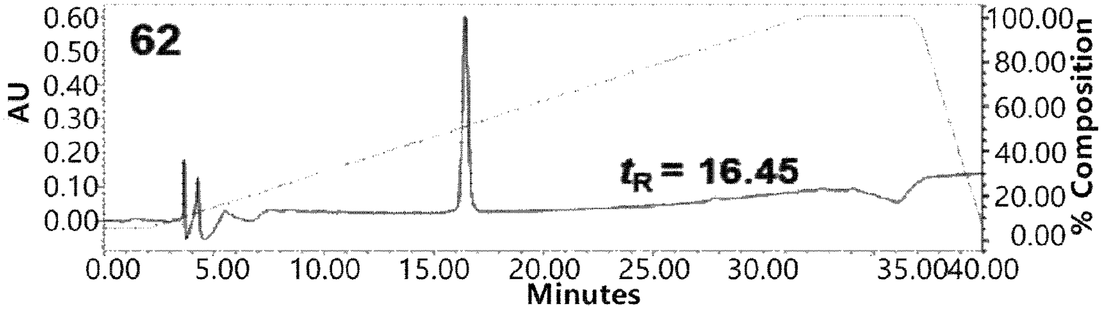
Figure 71:
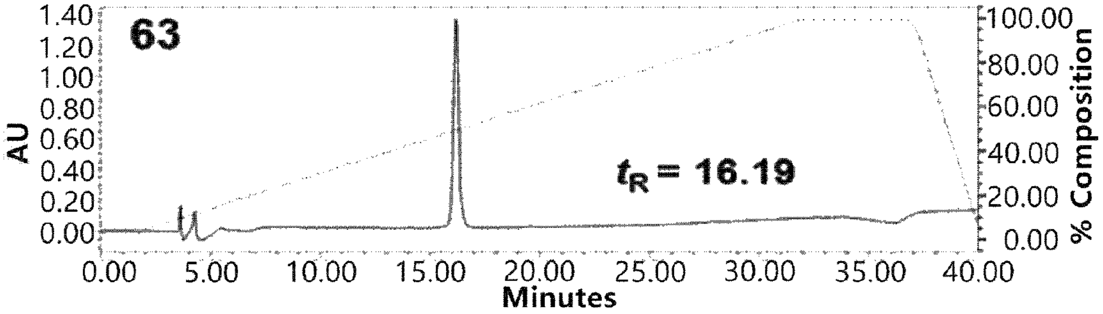
Figure 72:
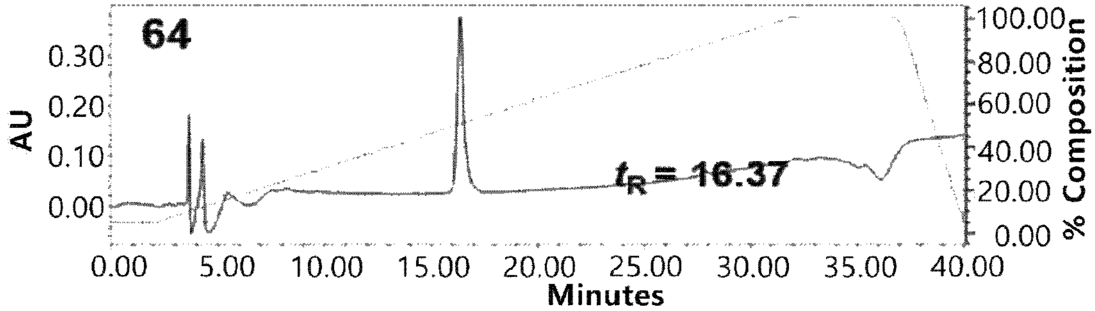
Figure 73:
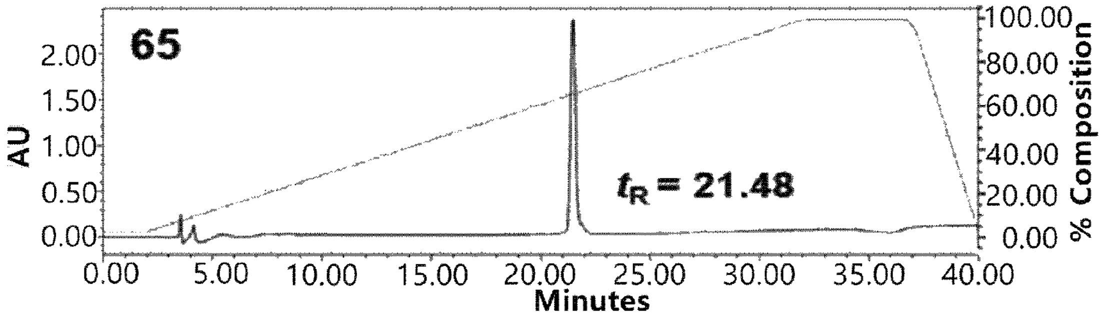
Figure 74:
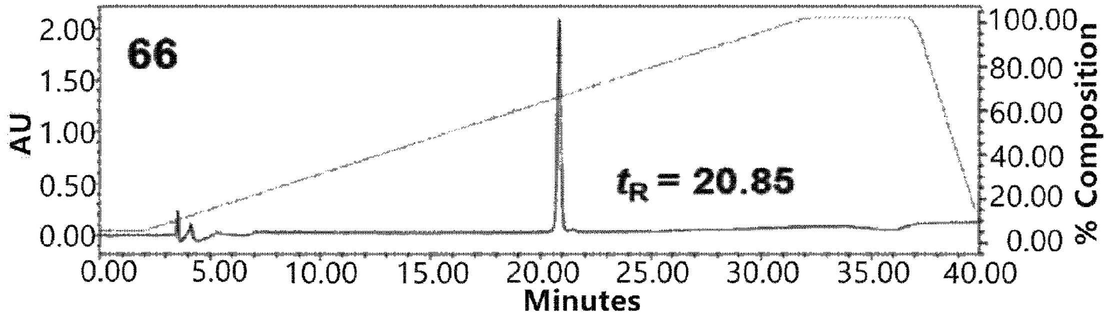
Figure 76:
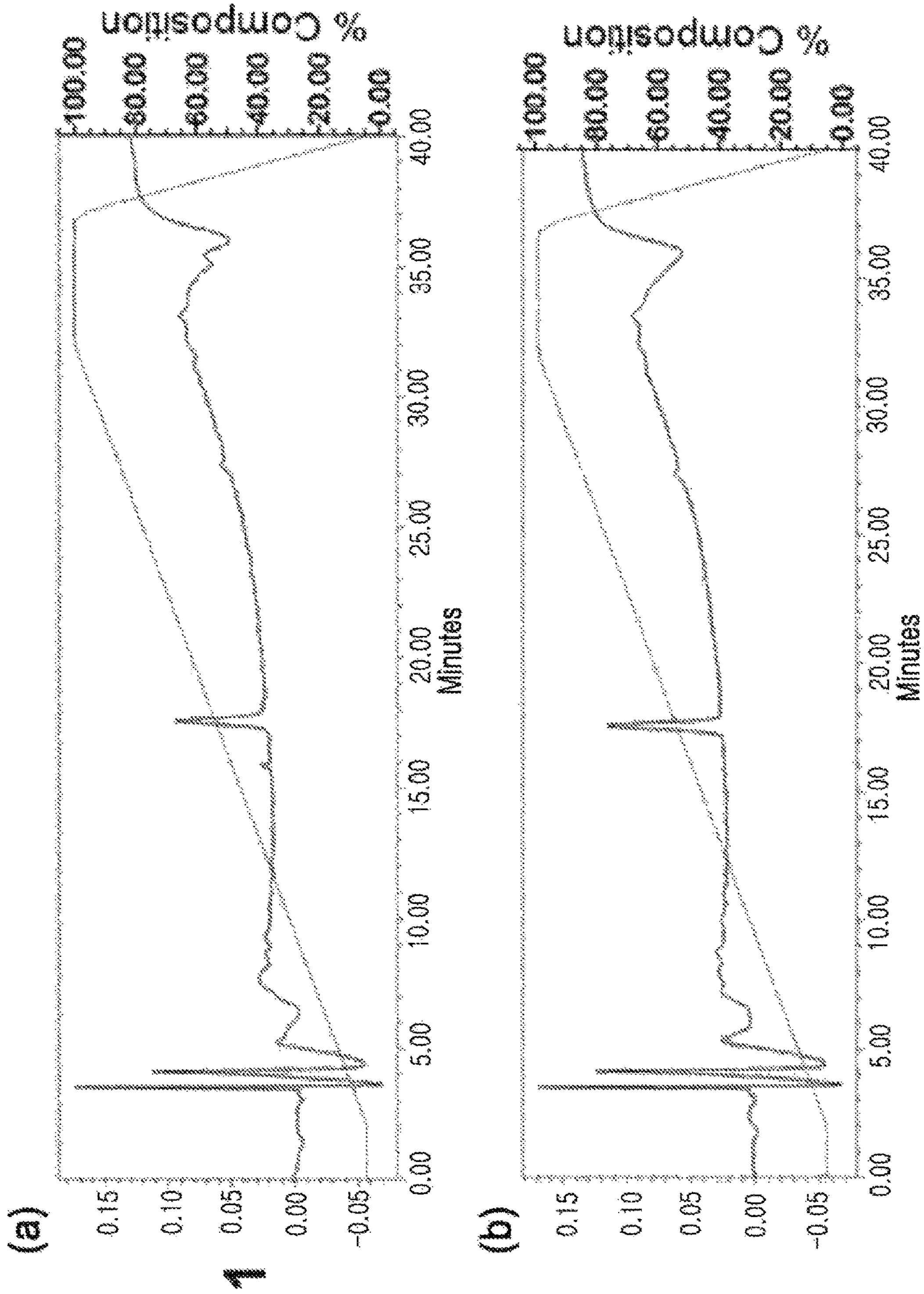
FIGS. 76 to 83 are the HPLC analysis results after a counter ion substitution reaction for Peptoids 1, 10, 11, 14, 15, 29, 32 and 37 of the present inventive concept using (a) HCl and (b) AcOH.
Figure 77:
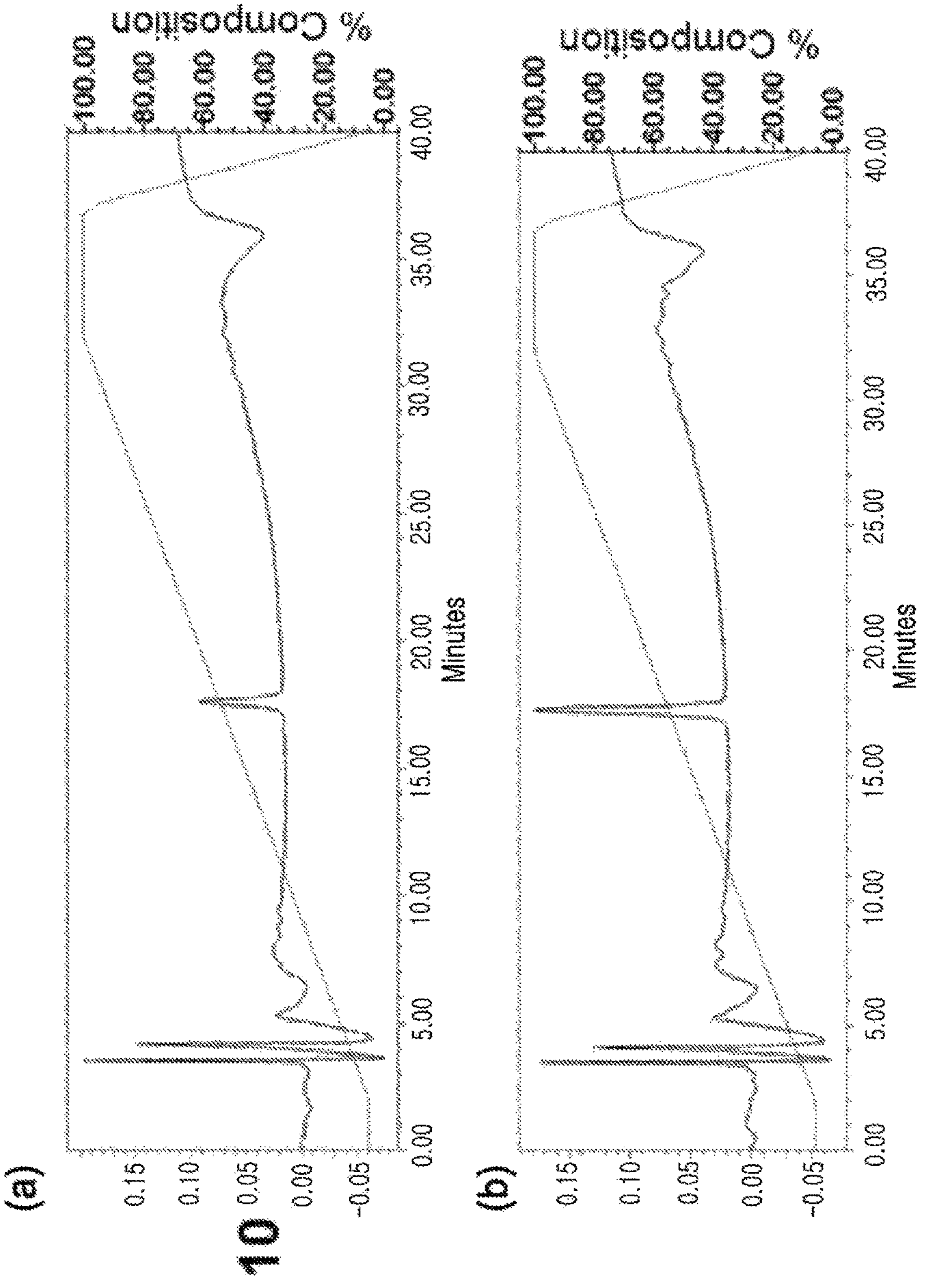
Figure 78:
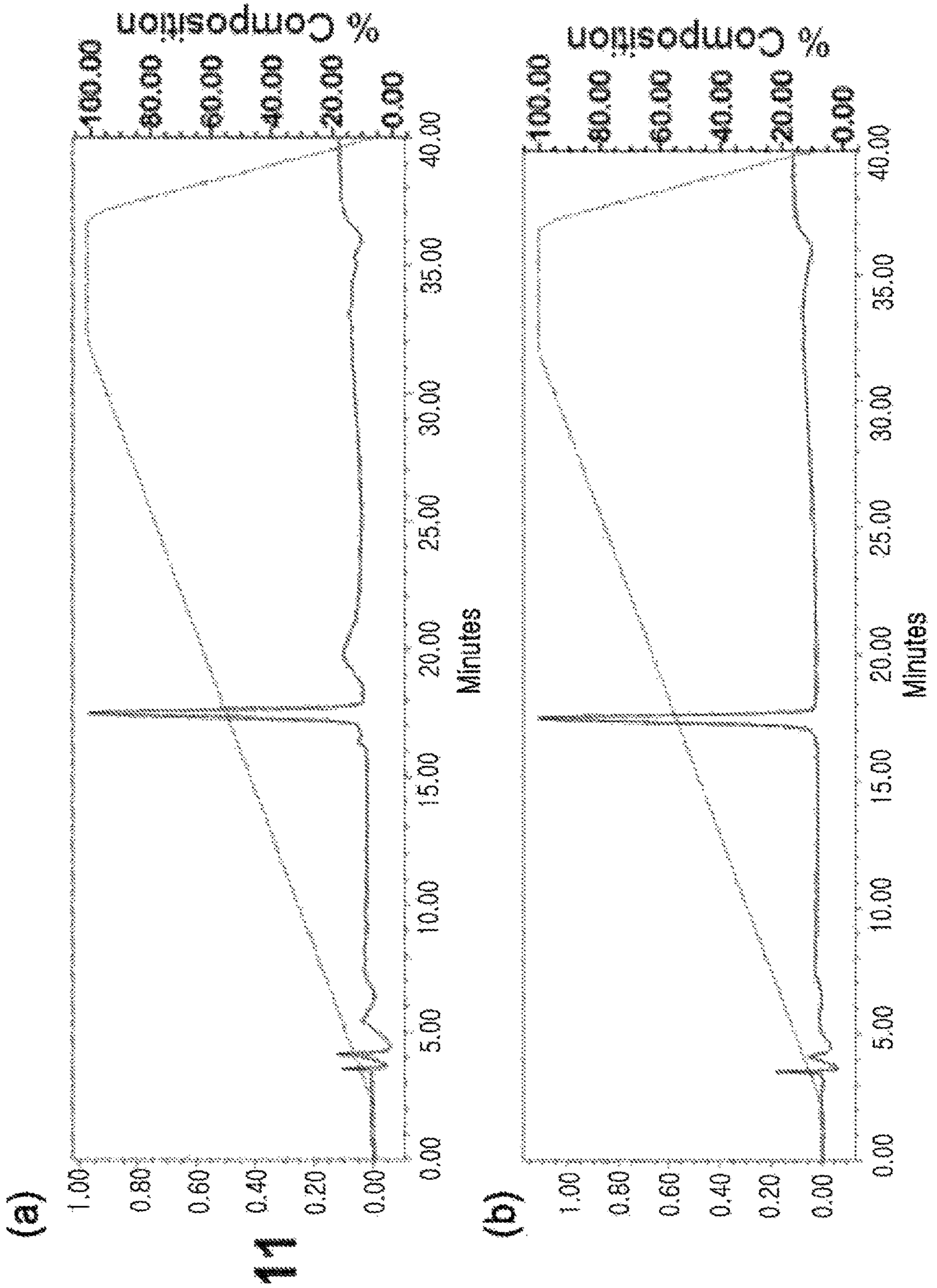
Figure 79:
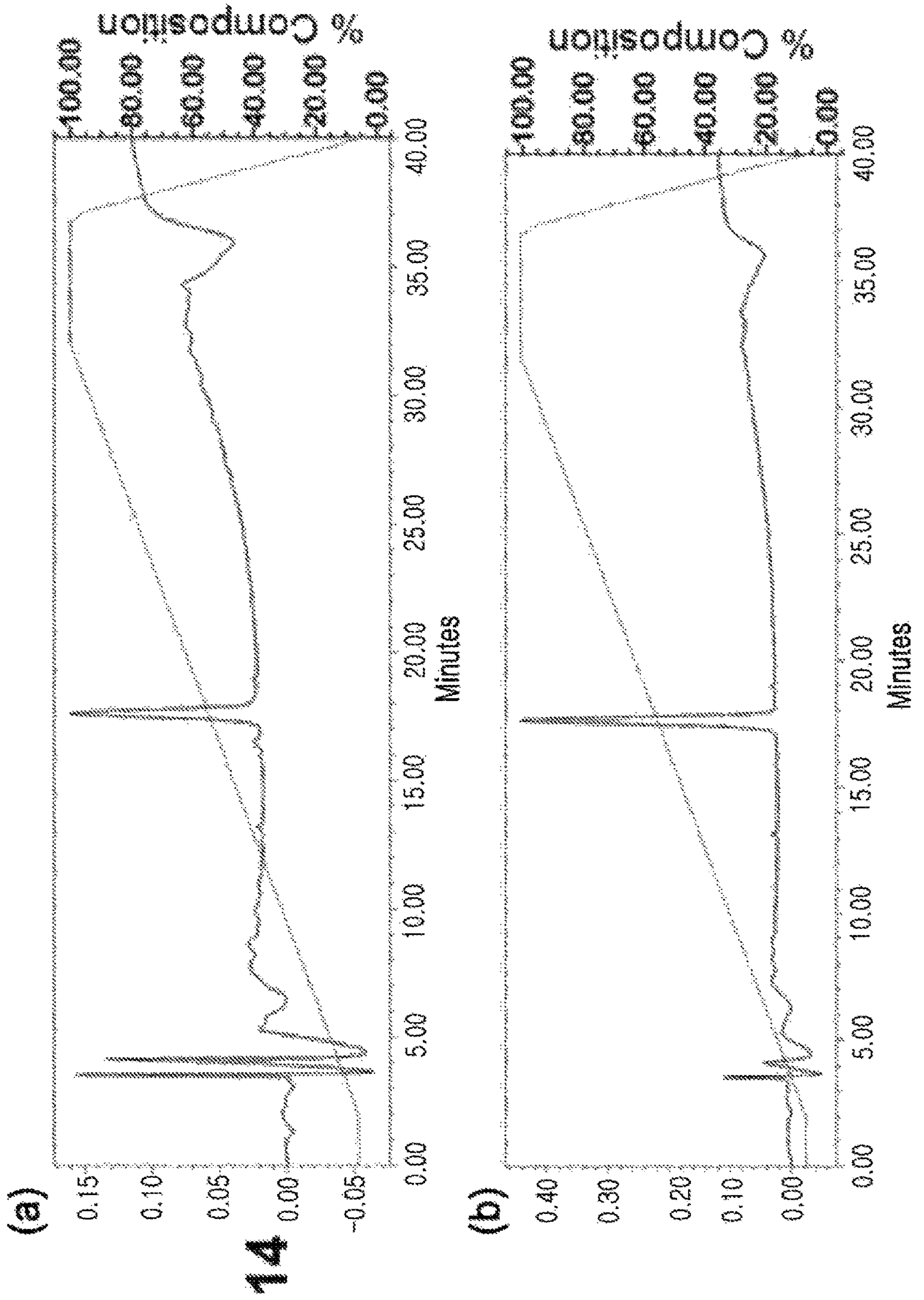
Figure 80:
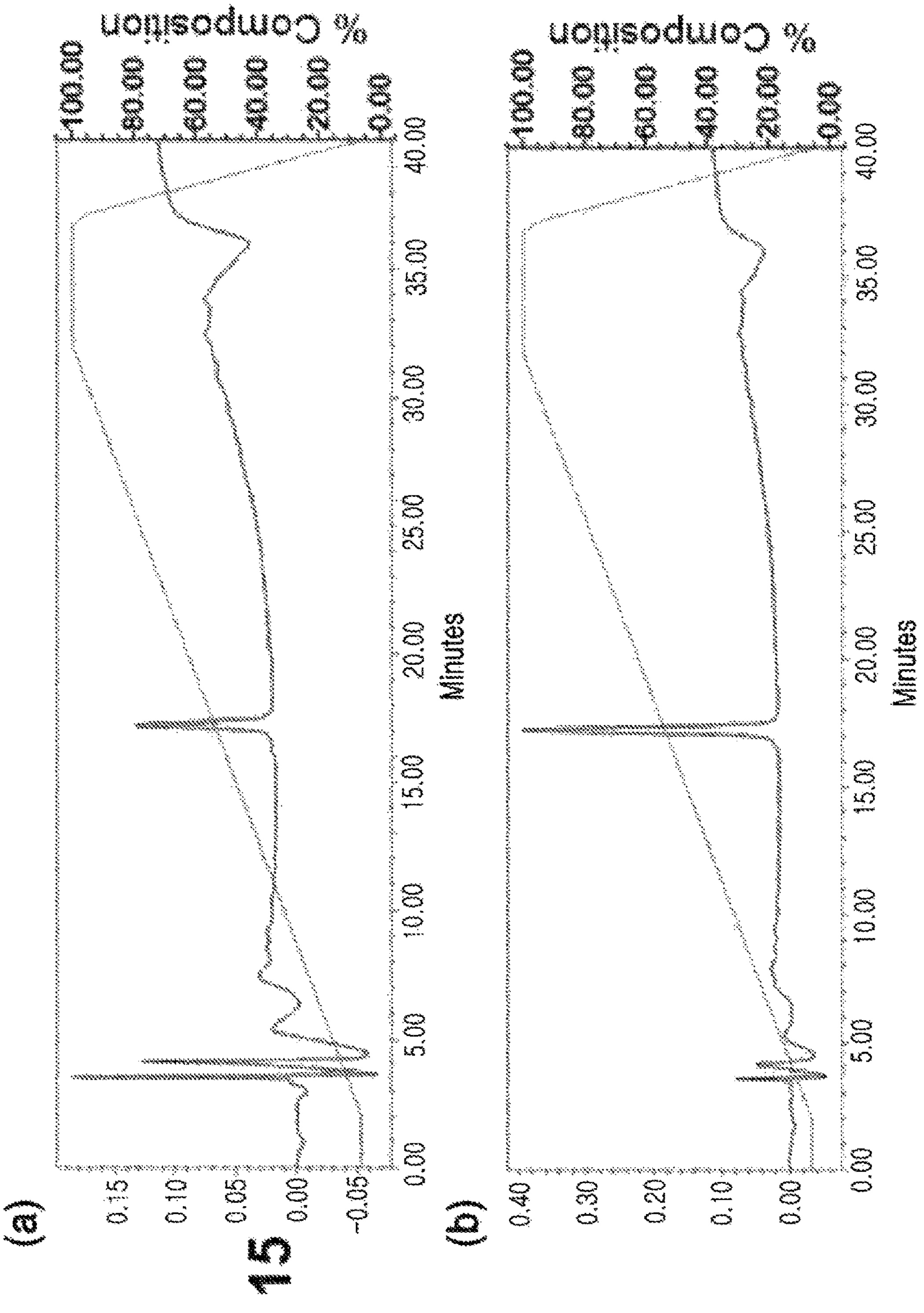
Figure 81:
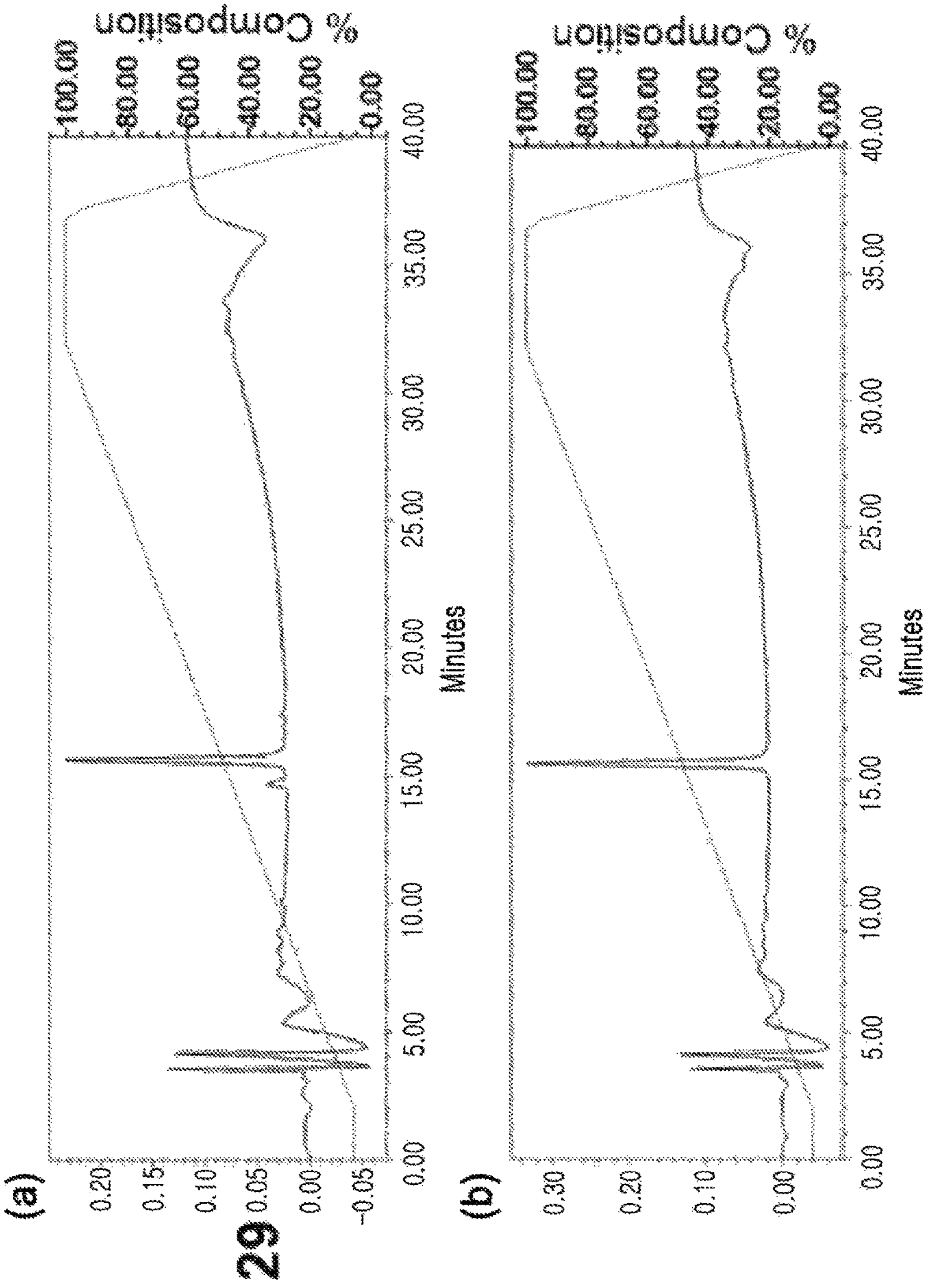
Figure 82:
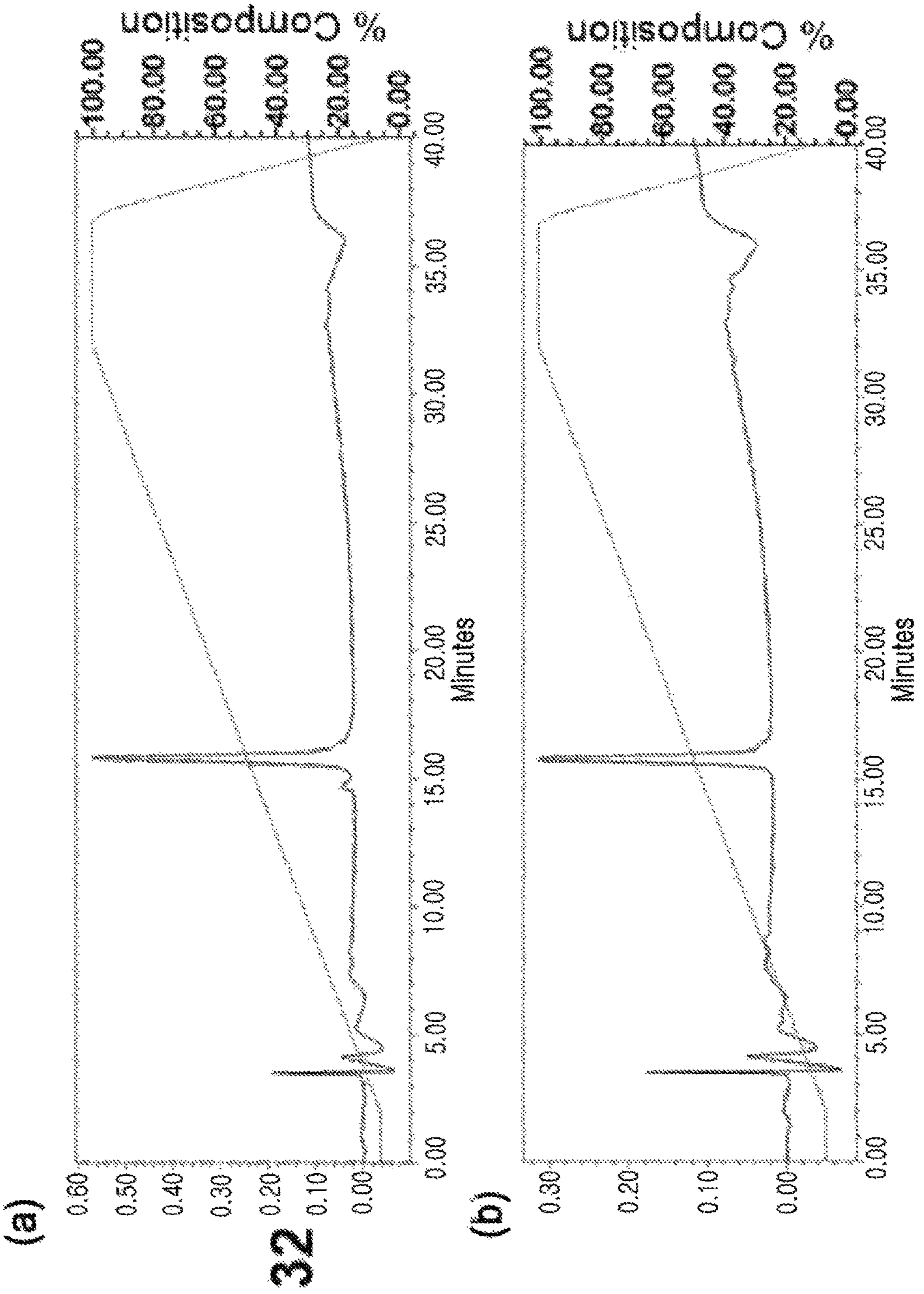
Figure 83:
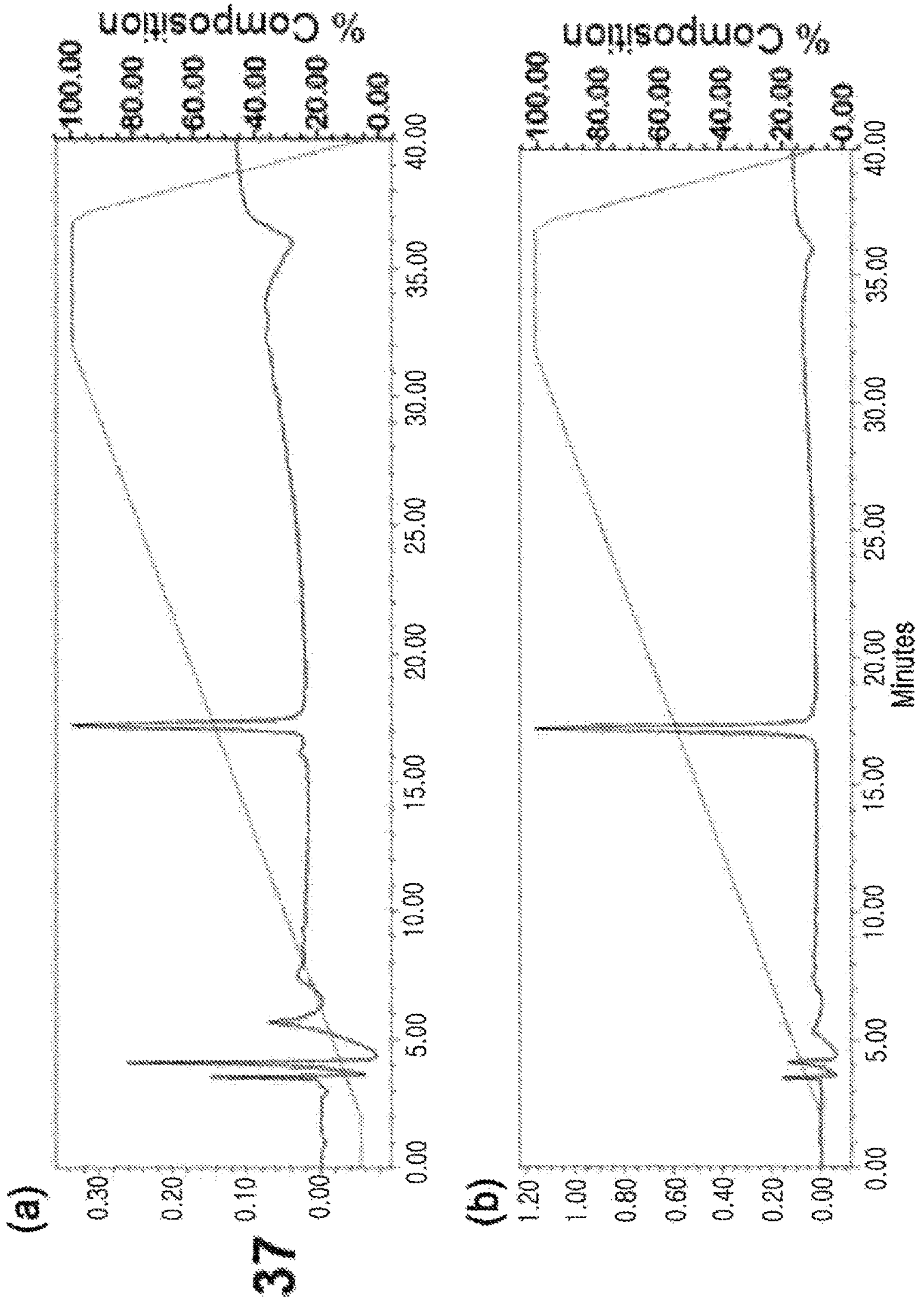

FIGS. 9 to 76 are graphs showing the HPLC and LC-MS analysis results for Peptoids 1 to 66 according to Example 1 of the present inventive concept.

Referring to FIGS. 9 to 76, in high performance liquid chromatography (HPLC) analysis, the hydrophobicity of the peptoids may be compared according to the type of monomer. When comparing the graphs of Peptoids 1 and 2, it was confirmed that, hydrophobicity is reduced as the number of carbon atoms was reduced according to the change from Nspe to Npm, the retention time (RT) slightly decreased (17.46→16.43 min).

In addition, it was confirmed that the retention time (RT) of each of Peptoids 3 to 6 in which one NhTrp monomer is added to the structure of Peptoid 1 increases, compared to Peptoid 1. In addition, it was confirmed that, compared to Peptoid 1, Peptoids 7 to 23 in which Nspe is substituted with one to four NhTrps had changes in retention time (RT) in the range of −0.4 min to +0.6 min. In addition, for Peptoids 24 to 38, compared to Peptoids 9, 11 and 14 in which one Nspe is substituted with NLys as a control, the retention time (RT) was reduced by approximately 1.5 min, and it was determined that this was a result of reducing hydrophobicity due to the removal of Nspe and the addition of NLys.

In addition, comparing Peptoids 48 to 64, the degree of hydrophobicity of each peptoid can be determined according to a monomer at the N-terminal position. Specifically, comparing Peptoid 48 with Peptoids 53 to 56, it was shown that, when Nspe is substituted with NLys, hydrophobicity was reduced. In addition, comparing Peptoids 49 to 52 with Peptoids 53 to 56, it was confirmed that the retention time (RT) was reduced after removing Nspe from the N-terminus. In Peptoids 57 to 60 in which NhTrp is substituted at the N-terminus, it was confirmed that the retention time (RT) is increased by 0.2 min compared to that of each Nspe control compound. In addition, in Peptoids 61 to 64, it was confirmed that as NhTrp was added to the N-terminus of each of Peptoids 53 to 56, compared to the control compound, the retention time (RT) was increased by approximately 0.8 min. In the case of Peptoids 65 and 66, as all of the amine groups of NLys are substituted with hydroxyl groups, the retention time (RT) was greatly increased by approximately 5 min, compared to a peptoid with an amine group, and Peptoids 65 and 66 were not dissolved in water due to a higher hydrophobicity than other peptoids.

Analysis Example 10: Electrospray Ionization-Mass Spectrometry

Electrospray ionization-mass spectrometry (ESI-MS) was performed on the antimicrobial peptoids of the present inventive concept, and the calculation and analysis results are shown in Tables 15 to 17 below. The term "nd" shown in Tables 15 to 17 below is the abbreviation for not determined, and indicates a value that is too small or too large to be measured.

TABLE 15

| | Calculated mass | | Observed mass | |
|---|---|---|---|---|
| Peptoid | $[M + H]^+$ | $[M + 2H]^{2+}$ | $[M + H]^+$ | $[M + 2H]^{2+}$ |
| 1 | 1819.1 | 910.1 | 1819.9 | 910.5 |
| 2 | 1707 | 854 | 1707.8 | 854.2 |
| 3 | 2019.2 | 1010.1 | nd | 1010.2 |
| 4 | 2019.2 | 1010.1 | nd | 1010.8 |
| 5 | 2219.3 | 1110.2 | nd | 1110.8 |
| 6 | 2219.3 | 1110.2 | nd | 1110.7 |
| 7 | 1858.1 | 929.6 | 1858.9 | 930 |
| 8 | 1858.1 | 929.6 | 1858.9 | 930 |
| 9 | 1858.1 | 929.6 | 1858.9 | 929.6 |
| 10 | 1858.1 | 929.6 | 1858.9 | 930 |
| 11 | 1897.1 | 949.1 | 1897.9 | 949.1 |
| 12 | 1897.1 | 949.1 | 1898 | 949.2 |
| 13 | 1897.1 | 949.1 | 1898 | 949.2 |
| 14 | 1897.1 | 949.1 | 1897.9 | 949.2 |
| 15 | 1897.1 | 949.1 | 1898 | 949.6 |
| 16 | 1897.1 | 949.1 | 1898 | 949.3 |
| 17 | 1897.1 | 949.1 | 1897.9 | 949.2 |
| 18 | 1975.1 | 988.1 | 1976 | 988.5 |
| 19 | 1975.1 | 988.1 | 1976 | 988.5 |
| 20 | 1975.1 | 988.1 | 1976 | 988.6 |
| 21 | 1975.1 | 988.1 | 1976 | 988.7 |
| 22 | 1975.1 | 988.1 | 1976 | 988.2 |
| 23 | 2131.2 | 1066.1 | nd | 1066.6 |

TABLE 16

| | Calculated mass | | Observed mass | |
|---|---|---|---|---|
| Peptoid | $[M + H]^+$ | $[M + 2H]^{2+}$ | $[M + H]^+$ | $[M + 2H]^{2+}$ |
| 24 | 1825.1 | 913.1 | 1826 | 913.2 |
| 25 | 1825.1 | 913.1 | 1825.9 | 913.6 |
| 26 | 1825.1 | 913.1 | 1825.9 | 913.2 |
| 27 | 1825.1 | 913.1 | 1826 | 913.2 |
| 28 | 1864.1 | 932.6 | 1864.9 | 932.6 |
| 29 | 1864.1 | 932.6 | 1865 | 932.7 |
| 30 | 1864.1 | 932.6 | 1865 | 933 |
| 31 | 1864.1 | 932.6 | 1865 | 933.1 |
| 32 | 1864.1 | 932.6 | 1864.9 | 933 |
| 33 | 1864.1 | 932.6 | 1864.9 | 932.7 |
| 34 | 1864.1 | 932.6 | 1865 | 932.7 |
| 35 | 2186.3 | 1093.7 | nd | 1094.2 |
| 36 | 2186.3 | 1093.7 | nd | 1094.2 |
| 37 | 1897.1 | 949.1 | 1897.9 | 949.2 |
| 38 | 1864.1 | 932.6 | 1864.9 | 933.1 |
| 39 | 1850.1 | 925.6 | 1851 | 925.7 |
| 40 | 1836.1 | 918.6 | 1836.9 | 919 |
| 41 | 1836.1 | 918.6 | 1836.9 | 919.1 |
| 42 | 2113.2 | 1057.1 | nd | 1057.3 |
| 43 | 2113.2 | 1057.1 | nd | 1057.3 |
| 44 | 1791.1 | 896.1 | 1791.9 | 896.6 |
| 45 | 1758.1 | 879.6 | 1758.9 | 879.7 |
| 46 | 1791.1 | 896.1 | 1791.9 | 896.6 |
| 47 | 1758.1 | 879.6 | 1758.9 | 880.1 |
| 48 | 1819.1 | 910.1 | 1818.9 | 910.1 |

TABLE 17

| | Calculated mass | | Observed mass | |
|---|---|---|---|---|
| Peptoid | $[M + H]^+$ | $[M + 2H]^{2+}$ | $[M + H]^+$ | $[M + 2H]^{2+}$ |
| 49 | 1625 | 813 | 1624.8 | 813.1 |
| 50 | 1625 | 813 | 1625.8 | 813.1 |
| 51 | 1625 | 813 | 1625.8 | 813.2 |
| 52 | 1625 | 813 | 1625.8 | 813.5 |
| 53 | 1786.1 | 893.6 | 1786.9 | 893.6 |
| 54 | 1786.1 | 893.6 | 1786.9 | 893.6 |
| 55 | 1786.1 | 893.6 | 1786.9 | 893.6 |
| 56 | 1786.1 | 893.6 | 1786.9 | 893.6 |
| 57 | 1825.1 | 913.1 | 1826 | 913.2 |
| 58 | 1825.1 | 913.1 | 1825.9 | 913.2 |
| 59 | 1825.1 | 913.1 | 1825.9 | 913.6 |
| 60 | 1825.1 | 913.1 | 1825.9 | 913.2 |
| 61 | 1986.2 | 993.6 | 1987 | 993.7 |
| 62 | 1986.2 | 993.6 | 1987 | 993.8 |
| 63 | 1986.2 | 993.6 | 1987 | 993.7 |
| 64 | 1986.2 | 993.6 | 1987 | 994 |
| 65 | 2135.1 | 1068.1 | nd | 1068.3 |
| 66 | 1869 | 935 | nd | 935.4 |

Electrospray ionization (ESI) is a method of analyzing the weight of a sample by forming a charged droplet by ionization while an organic sample is sprayed in an electric field and detecting the charged sample molecule by mass spectrometry, and is used particularly for a biomolecule with a high molecular weight and an active non-volatile compound. In Tables 15 to 17, $[M+H]^+$ indicates a value (m/z) obtained by dividing the measured mass of an ionized sample molecule to which one proton is attached by an electric charge, and $[M+2H]^{2+}$ indicates a value (m/z) obtained by dividing the measured mass of an ionized sample molecule to which two protons are attached by an electric charge. Each peptoid sample was prepared by being dissolved at a concentration of 10 μM in a solvent in which water and acetonitrile were mixed at 1:1 (v/v). Referring to Tables 15 to 17, the result of analyzing each peptoid sample revealed that a calculated mass is the same as an observed mass, thereby confirming that a peptoid with a predicted structure and a peptoid with an actual structure are manufactured in the same manner.

II. Confirmation of Change in Activity of Peptoid According to Counter Ion Substitution Preparation of Counter Ion-Substituted Peptoid The method of preparing an antimicrobial composition of the present inventive concept may further include, after S500 described above, a counter ion substitution process (S600) of removing trifluoroacetate (TFA) ions included in a composition using a carbonate ion exchange resin and adding an acidic solution.

The acidic solution may be acetic acid or hydrochloric acid.

Similar to a peptide, a peptoid is synthesized through the above-described solid-phase synthesis, in which trifluoroacetate (TFA) is included in a cleavage solution in the cleavage and removal of a protecting group such as an Fmoc or tert-butyl group. In addition, TFA is used as a mobile phase additive for ion pairing with amino groups of basic side chains and the N-terminus in reverse-phase high performance liquid chromatography (RP-HPLC). However, the presence of the TFA ion in the peptoid compound may change the behavior or shape of the peptoid, degrading analysis accuracy. In the present inventive concept, to improve the selectivity of a peptoid, counter ion substitution was performed.

Example 2: Preparation of Counter Ion-Substituted Peptoid

For Peptoids 1, 10, 11, 14, 15, 29, 32 and 37 selected from among Peptoids 1 to 66 prepared in Example 1, TFA ions were removed using a carbonate ion exchange resin (VariPure columns, USA). The peptoids were dissolved in H2O/ACN solution. The resin was adjusted with 2 to 3 bed volumes of methanol and 2 to 3 bed volumes of the desired mobile phase containing peptoids, and washed with 1 bed volume of methanol to allow the peptoid to be completely collected. Afterward, a desired fraction and a separated peptoid were combined using rotary evaporation. Subsequently, diluted acetic acid (AcOH) or hydrochloric acid (HCl) was added, and the eluent sample was dried.

Analysis Example 11: $^{19}$F-NMR Analysis for Confirming TFA Ion Removal After Counter Ion Substitution FIG. 75 is a graph showing $^{19}$F-NMR quantitative analysis for Peptoid 1 to measure a residual fluorine amount resulting from TFA ions after counter ion substitution.

Figure 75:
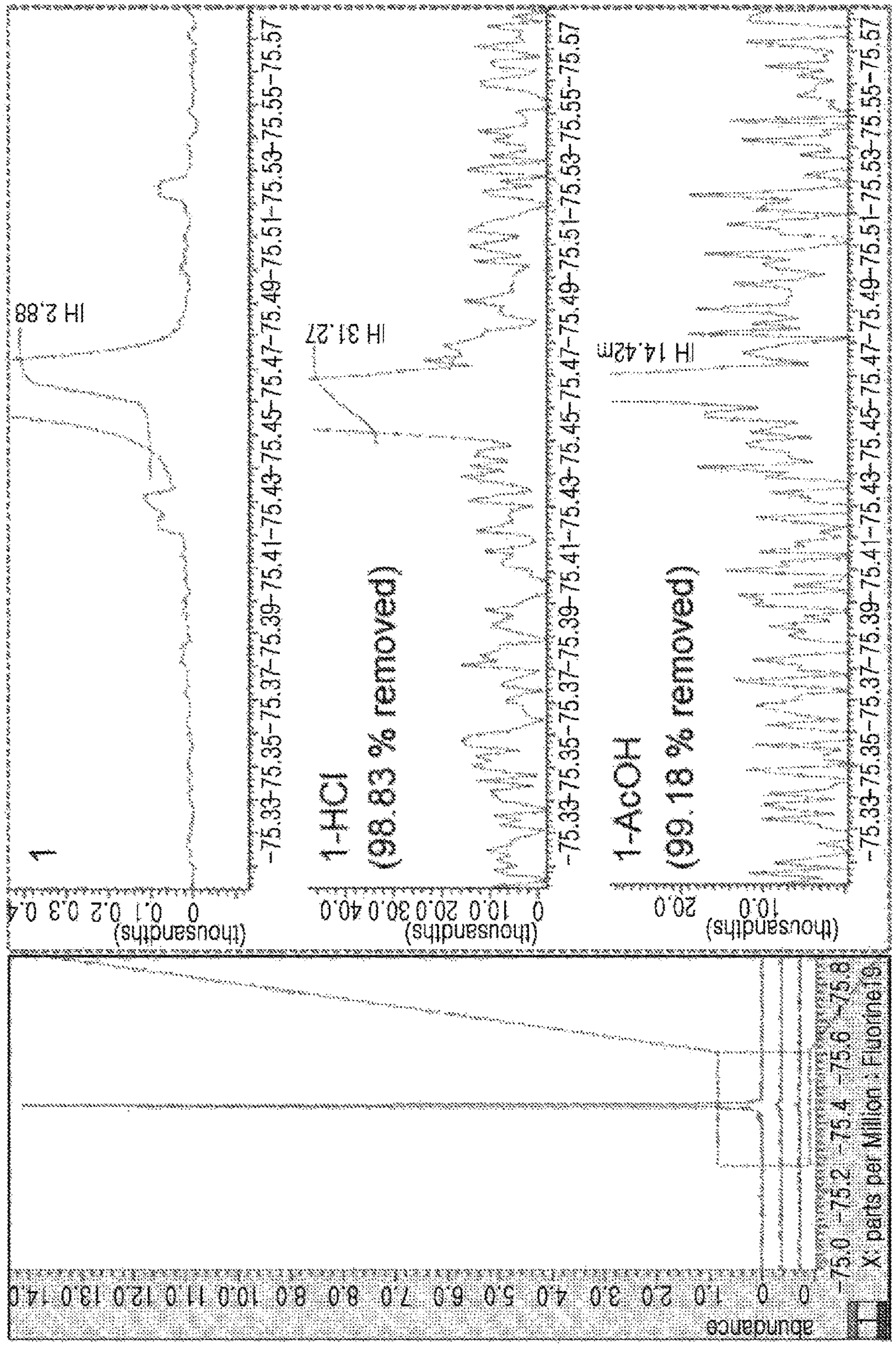
FIG. 75 is a graph showing the 19F-NMR quantitative analysis for Peptoid 1 to measure a remaining fluorine amount resulting from TFA ions_after a counter ion substitution reaction.

Referring to FIG. 75, it was confirmed that 98.83% and 99.18% of TFA were removed from peptoid compounds substituted with a chloride and an acetate, respectively.

Analysis Example 12: HPLC to Confirm Peptoid Decomposition After Counter Ion Substitution FIGS. 76 to 83 are the HPLC results for Peptoids 1, 10, 11, 14, 15, 29, 32 and 37 of the present inventive concept to confirm the decomposition of the peptoids after counter ion substitution using (a) HCl and (b) AcOH.

Referring to FIGS. 78 to 83, HPLC was performed for Peptoids 1, 10, 11, 14, 15, 29, 32 and 37 of the present inventive concept. Since the chloride (HCl) is a stronger acid than TFA, it can decompose acid-vulnerable peptoid compounds. However, the HPLC result did not show the peak of an acid used in counter ion substitution at 220 nm, confirming that almost no peptoid decomposition occurred even after counter ion substitution.

Analysis Example 13: Confirmation of Antimicrobial Activity and Hemolytic Activity of Counter Ion-Substituted Peptoids and Analysis of Selectivity Thereof In Table 18 below, the confirmation of antimicrobial activity and hemolytic activity of a counter ion-substituted peptoid of the present inventive concept against red blood cells and the analysis of the selectivity thereof are summarized.

Referring to Table 18, as the result of counter ion substitution, in Peptoids 10, 15 and 37, antimicrobial activity was reduced, but the antimicrobial activity was maintained in the other peptoids. That is, it can be seen that most of the peptoids of the present inventive concept tend to show the same antimicrobial activity as before substitution even after counter ion substitution. In addition, it is confirmed that, compared to a TFA salt-containing peptoid, the peptoids that are subjected to counter ion substitution with HCI and AcOH salts show overall low cytotoxicity. Particularly, it can be confirmed that Peptoid 29-AcOH and Peptoid 32-HCl have the maximum selectivity for red blood cells.

TABLE 18

| | | MIC (μM) | | | | |
|---|---|---|---|---|---|---|
| Classification | Compound | *E. coli* ATCC25922 | *S. aureus* ATCC25923 | $HC_{10}/HC_{50}$ (μM) | $H_{max}$ (100 μM) | Selectivity |
| Peptoid 1 | 1 | 6.3 | 1.6 | 15.9/49.0 | 72.1 ± 2.1 | 2.5 |
| Peptoid 1-1 | 1-HCl | 6.3 | 1.6 | 27.6/83.3 | 61.5 ± 0.9 | 4.4 |
| Peptoid 1-2 | 1-AcOH | 12.5 | 3.1 | 25.0/78.6 | 58.2 ± 1.7 | 2 |
| Peptoid 10 | 10 | 3.1 | 0.8 | 6.9/25.8 | 101.4 ± 5.1 | 2.2 |
| Peptoid 10-1 | 10-HCl | 6.3 | 3.1 | 15.3/37.8 | 81.5 ± 7.4 | 2.4 |
| Peptoid 10-2 | 10-AcOH | 6.3 | 1.6 | 14.1/29.4 | 102.3 ± 11.3 | 2.2 |
| Peptoid 11 | 11 | 3.1 | 1.6 | 6.9/27.5 | 111.9 ± 2.7 | 2.2 |
| Peptoid 11-1 | 11-HCl | 3.1 | 3.1 | 10.1/21.5 | 113.9 ± 1.7 | 3.3 |
| Peptoid 11-2 | 11-AcOH | 3.1 | 1.6 | 8.7/29.7 | 110.4 ± 0.2 | 2.8 |
| Peptoid 14 | 14 | 3.1 | 1.6 | 12.5/21.1 | 112.9 ± 2.1 | 4 |
| Peptoid 14-1 | 14-HCl | 3.1 | 3.1 | 19.2/68.2 | 75.3 ± 5.0 | 6.2 |
| Peptoid 14-2 | 14-AcOH | 3.1 | 1.6 | 14.9/51.8 | 100.7 ± 17.2 | 4.8 |
| Peptoid 15 | 15 | 3.1 | 1.6 | 20.5/89.2 | 53.4 ± 3.1 | 6.6 |
| Peptoid 15-1 | 15-HCl | 6.3 | 3.1 | 50.4/>100 | 33.4 ± 9.7 | 8 |

TABLE 18-continued

| Classification | Compound | MIC (μM) E. coli ATCC25922 | MIC (μM) S. aureus ATCC25923 | $HC_{10}/HC_{50}$ (μM) | $H_{max}$ (100 μM) | Selectivity |
|---|---|---|---|---|---|---|
| Peptoid 15-2 | 15-AcOH | 6.3 | 3.1 | 39.2/>100 | 34.1 ± 1.1 | 6.2 |
| Peptoid 29 | 29 | 6.3 | 12.5 | 88.6/>100 | 12.3 ± 1.3 | 14.1 |
| Peptoid 29-1 | 29-HCl | 12.5 | 12.5 | >100/>100 | 4.3 ± 0.3 | >8.0 |
| Peptoid 29-2 | 29-AcOH | 6.3 | 12.5 | >100/>100 | 5.2 ± 0.2 | >15.9 |
| Peptoid 32 | 32 | 6.3 | 3.1 | >100/>100 | 4.2 ± 1.0 | >15.9 |
| Peptoid 32-1 | 32-HCl | 6.3 | 6.3 | >100/>100 | 8.7 ± 0.6 | >15.9 |
| Peptoid 32-2 | 32-AcOH | 6.3 | 6.3 | 83.0/>100 | 13.8 ± 1.1 | 13.2 |
| Peptoid 37 | 37 | 3.1 | 1.6 | 13.2/38.6 | 80.7 ± 12.8 | 4.3 |
| Peptoid 37-1 | 37-HCl | 6.3 | 3.1 | 14.4/56.5 | 86.6 ± 5.7 | 2.3 |
| Peptoid 37-2 | 37-AcOH | 6.3 | 1.6 | 12.5/26.0 | 98.9 ± 8.0 | 2 |

Analysis Example 14: Confirmation of Cytotoxicity of Counter Ion-Substituted Peptoid Human lung cells (MRC-5) were purchased from the Korean Cell Line Bank, and human keratinocytes (HaCaT) were purchased from the AmorePacific R&D Center. All cells were grown in a Dulbecco's modified Eagle's medium containing 10% fetal bovine serum under conditions of 5% $CO_2$ and 37 °C. To confirm the effect of a peptoid on cell growth, 3-(4,5-dimethylthiazol-2-yl)-5-(3-carboxymethoxyphenyl)-2-(4-sulfophenyl)-2H-tetrazolium (MTS) cell assay was performed to determine cell viability. An aliquot (100 μL) of a batch including $1.3\times10^4$ MRC-5 cells/mL or $3\times10^4$ HaCaT cells/mL was dispensed into each well of a 96-well plate. The cells were grown at 37 °C in a 5% $CO_2$ humid atmosphere and allowed to adhere for 24 hours. When the cells reached approximately 70% confluency, the medium was replaced with serial dilutions of the peptoid stock and incubated for 24 hours. 20 μL of a CellTiter 96 aqueous non-radioactive cell proliferation assay reagent (Promega, USA) including a tetrazolium compound was added to each well.

The contents in the plate were metabolized by incubating at 37 °C for 4 hours. An MTS-formazan product of viable cells was measured at 490 nm using a microplate reader, and cell viability (%) was calculated by Equation 2 below and compared with untreated cells.

$$\text{Cell viability (\%)}=[A/(A_{control})]\times100 \quad \text{[Equation 2]}$$

In Equation 2, A is the absorbance of a test well, and $A_{control}$ is the average absorbance of a well containing untreated cells.

The abbreviation "$LC_{50}$" shown in Table 19 below is lethal dose 50, indicating cell viability, and is defined as the concentration of a compound that causes 50% cell lethality. Particularly, Peptoids 29 and 32 showing high selectivity for red blood cells showed 20% lower toxicity against MRC-5 and HaCaT cells compared to the peptoid having a TFA salt after counter ion substitution. Accordingly, as representative peptoid compounds, Peptoid 29-2 and Peptoid 32-1 were selected. Particularly, Peptoid 32-1, which has high activity against gram-negative bacteria and high selectivity for red blood cell hemolysis, exhibited lower animal cell toxicity than Peptoid 29-2. The term "nd" shown in Table 19 below is the abbreviation for not determined, and indicates a value that is too small or too large to be measured.

TABLE 19

| Classification | Compound | $LC_{50}$(μM) MRC-5 | $LC_{50}$(μM) HaCaT |
|---|---|---|---|
| Peptoid 1 | 1 | 8.1 | 7.3 |
| Peptoid 1-1 | 1-HCl | 11.8 | nd |
| Peptoid 1-2 | 1-AcOH | 8.6 | nd |
| Peptoid 10 | 10 | nd | nd |
| Peptoid 10-1 | 10-HCl | nd | nd |
| Peptoid 10-2 | 10-AcOH | nd | nd |
| Peptoid 11 | 11 | 6.9 | nd |
| Peptoid 11-1 | 11-HCl | 9.6 | nd |
| Peptoid 11-2 | 11-AcOH | 8.3 | nd |
| Peptoid 14 | 14 | 9.7 | nd |
| Peptoid 14-1 | 14-HCl | 12.1 | nd |
| Peptoid 14-2 | 14-AcOH | 13.8 | nd |
| Peptoid 15 | 15 | nd | nd |
| Peptoid 15-1 | 15-HCl | nd | nd |
| Peptoid 15-2 | 15-AcOH | nd | nd |
| Peptoid 29 | 29 | 11.8 | 18.8 |
| Peptoid 29-1 | 29-HCl | 23.9 | >25.0 |
| Peptoid 29-2 | 29-AcOH | 16 | 22 |
| Peptoid 32 | 32 | 14.5 | 17.1 |
| Peptoid 32-1 | 32-HCl | 18.1 | 21.4 |
| Peptoid 32-2 | 32-AcOH | 16.9 | 21.3 |
| Peptoid 37 | 37 | nd | nd |
| Peptoid 37-1 | 37-HCl | nd | nd |
| Peptoid 37-2 | 37-AcOH | nd | nd |

Figure 84:
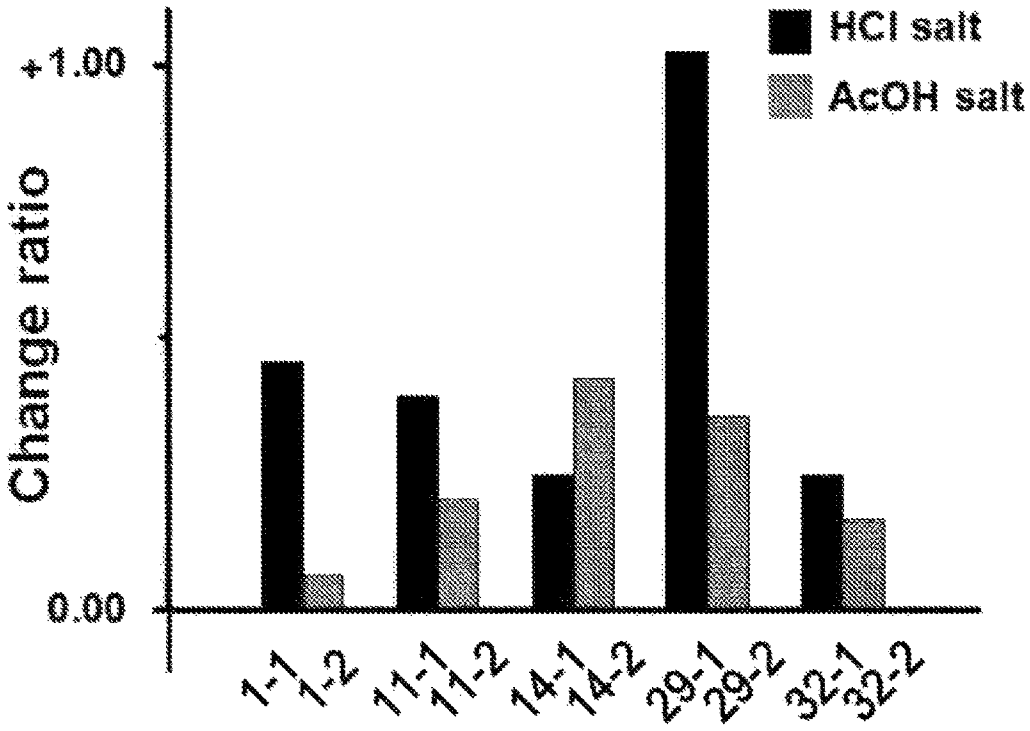
FIG. 84 is a graph showing the rate of change in the $LC_{50}$ value of a counter ion-substituted peptoid and showing the results for MRC-5 cells according to one embodiment of the present inventive concept.
Figure 85:
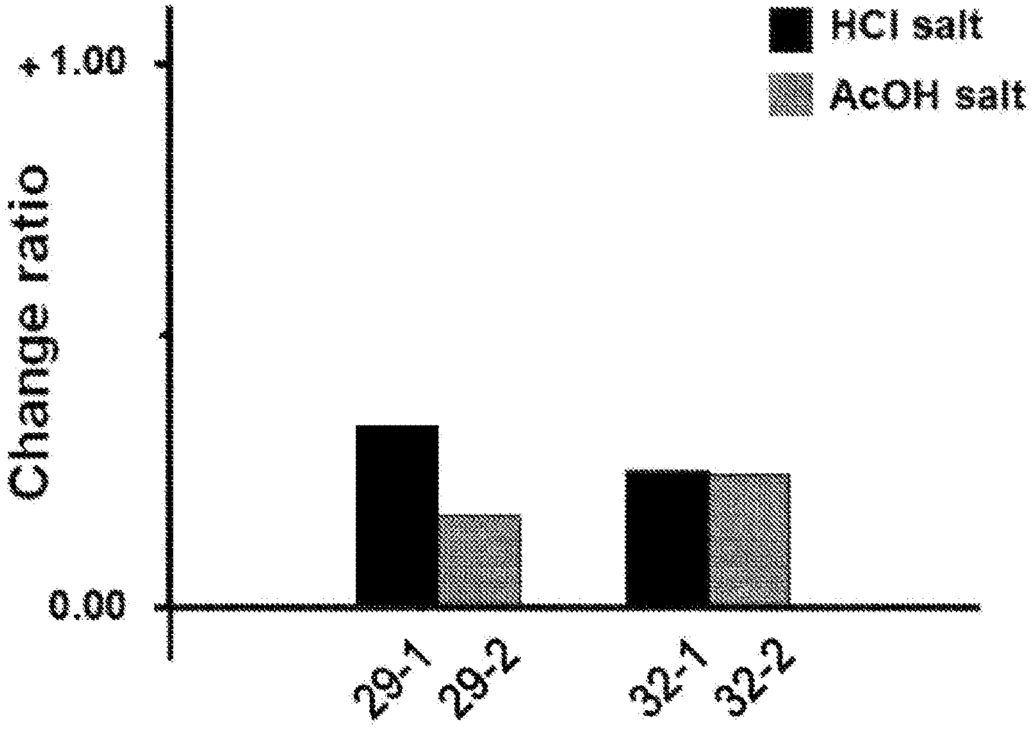
FIG. 85 is a graph showing the rate of change in the LC50 value of a counter ion-substituted peptoid and showing the results for HaCaT cells according to one embodiment of the present inventive concept.
Figure 86:
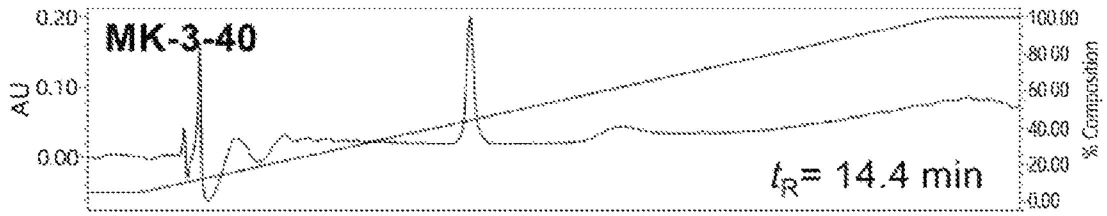
FIGS. 86 to 100 are the HPLC analysis results for antimicrobial Peptoids 67 to 81 according to one embodiment of the present inventive concept.
Figure 87:
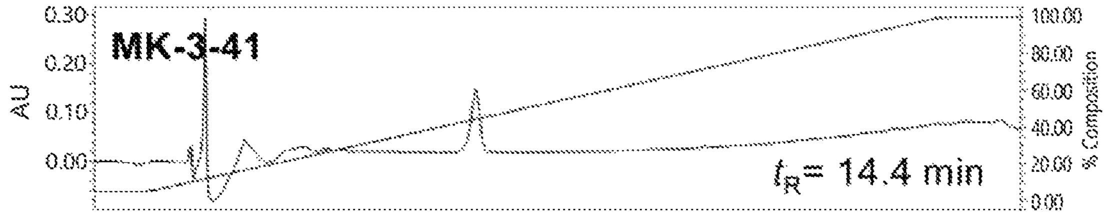
Figure 88:
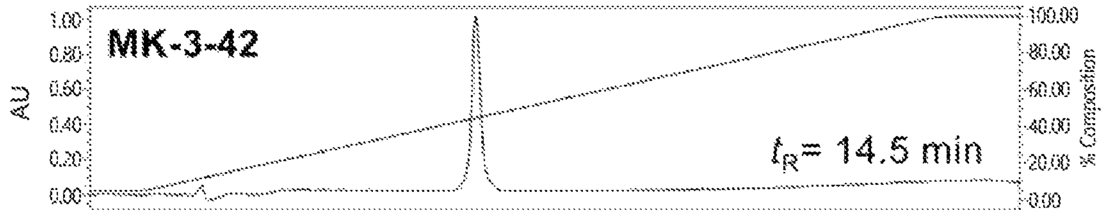
Figure 89:
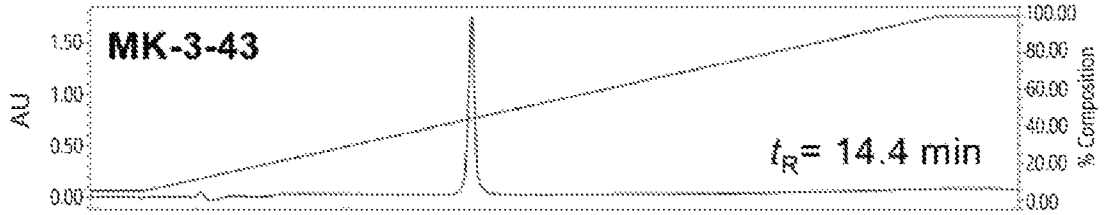
Figure 90:
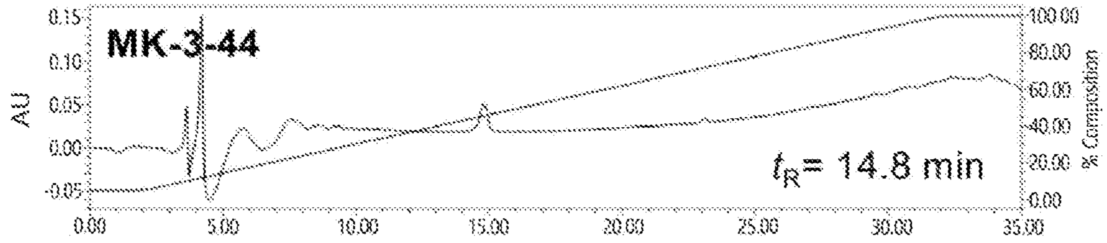
Figure 91:
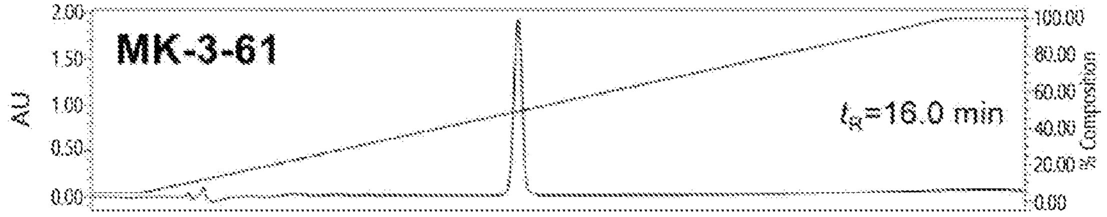
Figure 92:
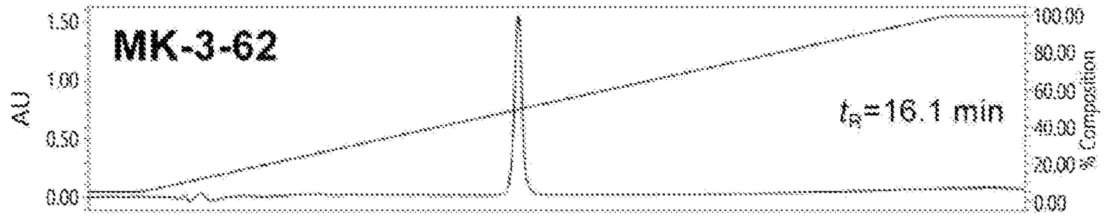
Figure 93:
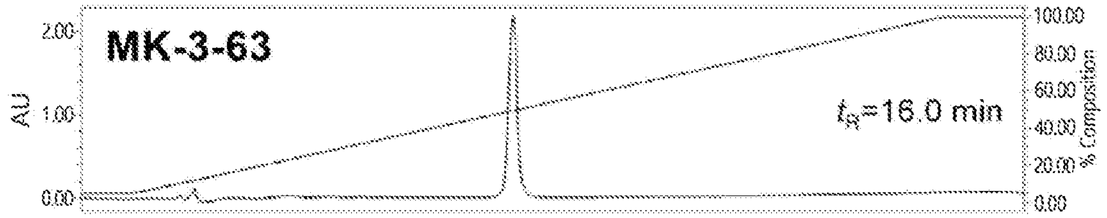
Figure 94:
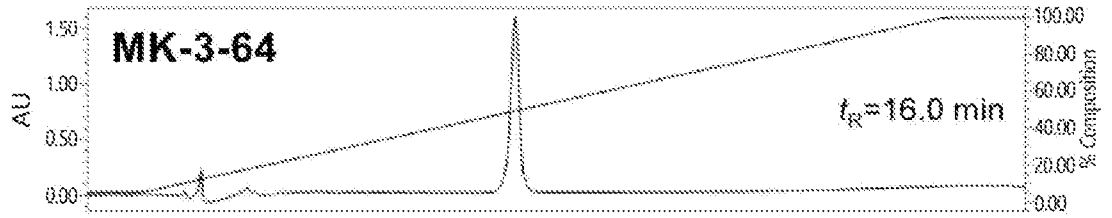
Figure 95:
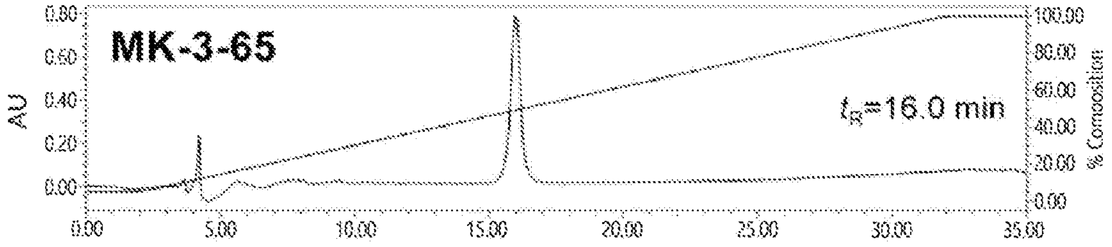
Figure 96:
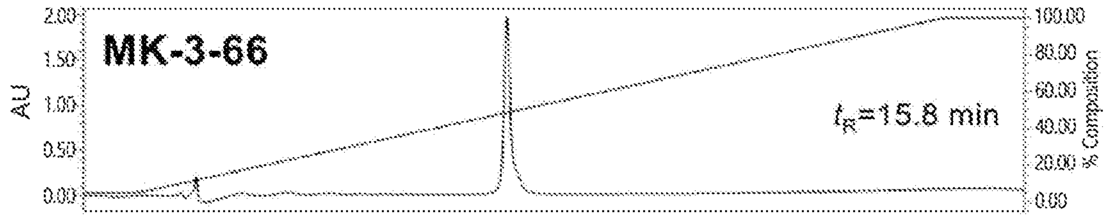
Figure 97:
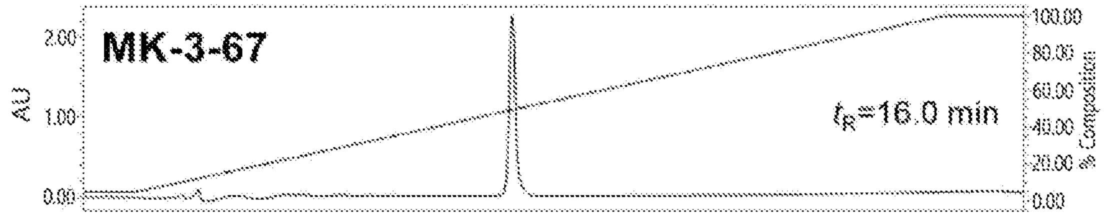
Figure 98:
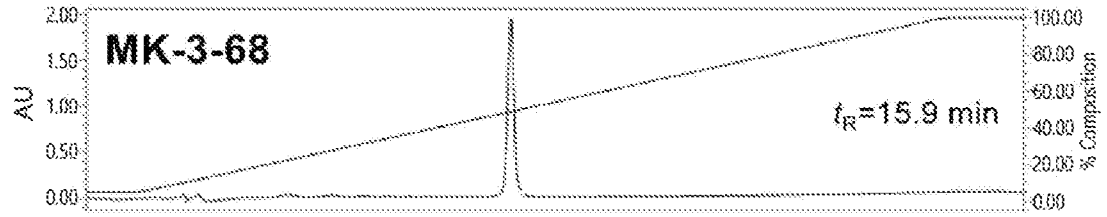
Figure 99:
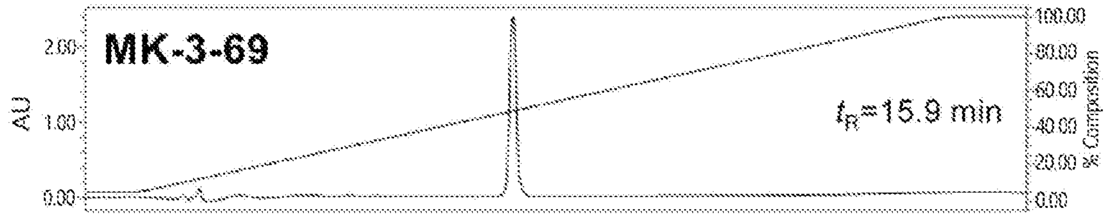
Figure 100:
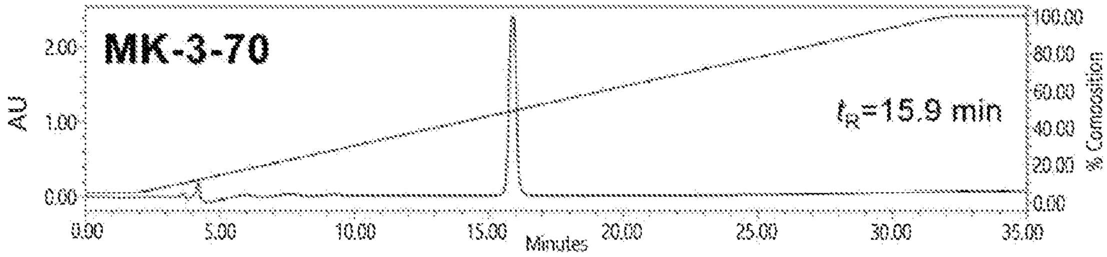

FIG. 84 is a graph showing the rate of change in the $LC_{50}$ value for MRC-5 cells of a counter ion-substituted peptoid according to one embodiment of the present inventive concept, and FIG. 85 shows the rate of change in the $LC_{50}$ value for HaCaT cells.

The rate of change was calculated using Equation 3 below.

$$\text{Rate of change}=(D-E)/D \quad \text{[Equation 3]}$$

In Equation 3, D indicates the $L_{50}$ value of the TFA salt, and E indicates the $L_{50}$ value of an exchanged salt (HCl or AcOH).

Referring to FIGS. 84 and 85, comparing Peptoids 29-1 (29-HCl), 29-2 (29-AcOH), 32-1 (32-HCl) and 32-2 (32-AcOH), it was confirmed that, through counter ion substitution, for both MRC-5 and HaCaT cells, the $LC_{50}$ values of the peptoids increase. Accordingly, it was confirmed that the cytotoxicity of antimicrobial peptoids can be effectively reduced through counter ion substitution. In addition, except for Peptoid 29-HCl in which a counter ion is changed into a chloride, as the MIC against *E. coli* was constantly maintained at 6.3 μM, it can be seen that the effect of antimicrobial activity was maintained regardless whether the counter ion substitution was performed or not. As a result, the peptoids containing NhTrp can maintain the effect of antimicrobial activity and can reduce cytotoxicity through the counter ion substitution.

III. Confirmation of Change in Peptoid Activity According to NHis Substitution

Example 3: Preparation of Peptoids 67 to 81

Antimicrobial peptoids were prepared in the same manner as the method of preparing a peptoid described in Example 1, except that NhTrp(Boc), NLys(Boc), N4hb(TIPS). Npm and Nspe were used as submonomers and NHis(Trt) was additionally used.

The chemical structures of Peptoids 67 to 81 according to Example 3 of the present inventive concept are shown in Table 20 below.

TABLE 20

| | Chemical structure |
|---|---|
| Peptoid 67 | 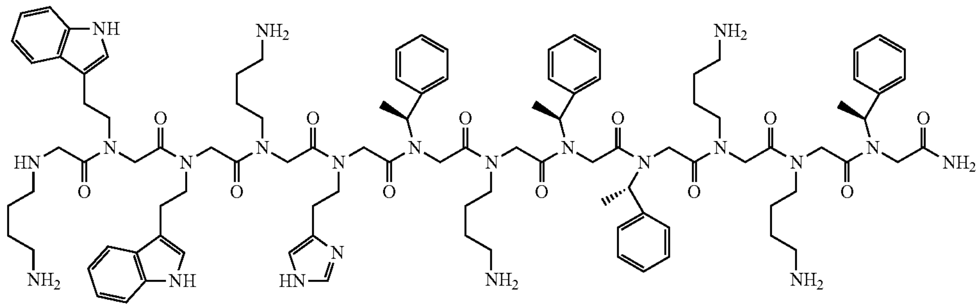 [SMILES: C[C@@H](c1ccccc1)N(CC(N)=O)C(=O)CN(CCCCN)C(=O)CN(CCCCN)C(=O)CN(C(=O)CN(C(=O)CN(CCCCN)C(=O)CN(C(=O)CN(CCc1c[nH]cn1)C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1] MK-3-40 |
| Peptoid 68 | 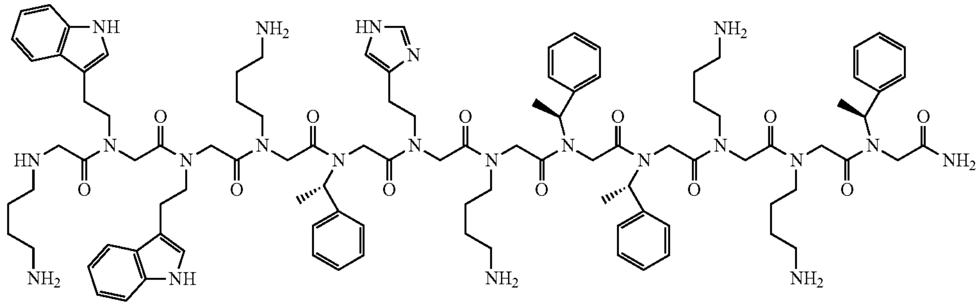 [SMILES: C[C@@H](c1ccccc1)N(CC(N)=O)C(=O)CN(CCCCN)C(=O)CN(CCCCN)C(=O)CN(C(=O)CN(C(=O)CN(CCCCN)C(=O)CN(CCc1c[nH]cn1)C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1] MK-3-41 |
| Peptoid 69 | 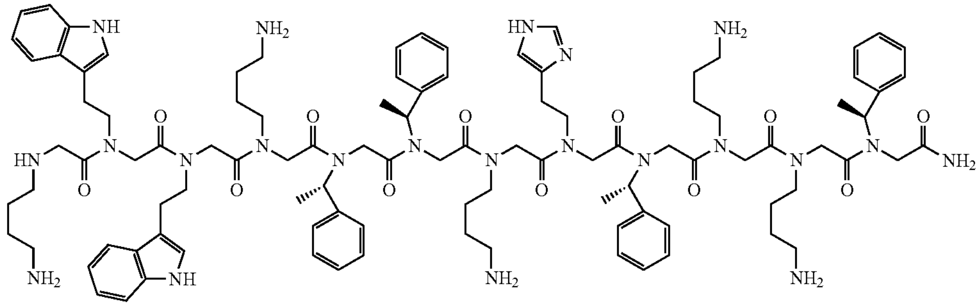 [SMILES: C[C@@H](c1ccccc1)N(CC(N)=O)C(=O)CN(CCCCN)C(=O)CN(CCCCN)C(=O)CN(C(=O)CN(CCc1c[nH]cn1)C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1] MK-3-42 |

TABLE 20-continued
| Chemical structure |
| --- |
| Peptoid 70 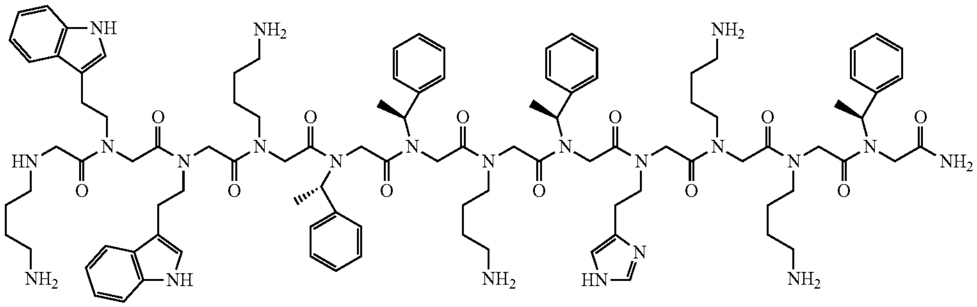 [SMILES: C[C@@H](c1ccccc1)N(CC(N)=O)C(=O)CN(CCCCN)C(=O)CN(CCCCN)C(=O)CN(CCc1c[nH]cn1)C(=O)CN(C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1] MK-3-43 |
| Peptoid 71 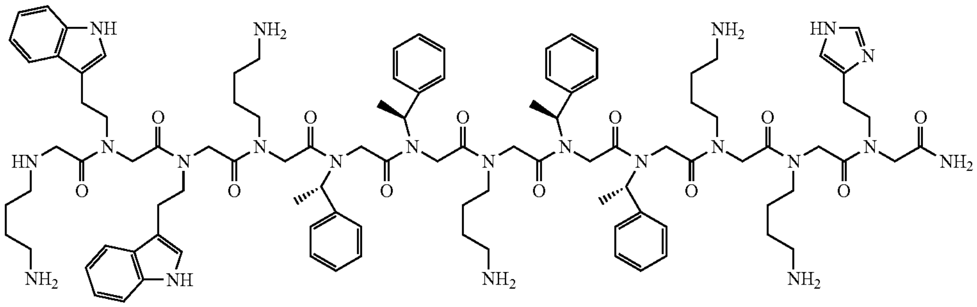 [SMILES: C[C@@H](c1ccccc1)N(CC(=O)N(CCCCN)CC(=O)N(CC(=O)N(CC(=O)N(CCCCN)CC(=O)N(CCCCN)CC(=O)N(CCc1c[nH]cn1)CC(N)=O)[C@@H](C)c1ccccc1)[C@@H](C)c1ccccc1)C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1] MK-3-44 |
| Peptoid 72 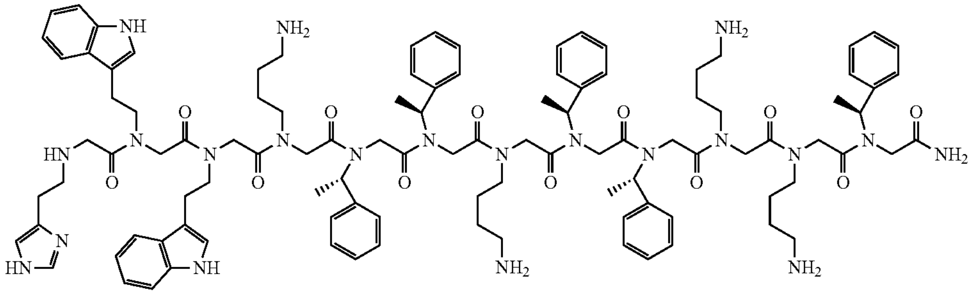 [SMILES: C[C@@H](c1ccccc1)N(CC(N)=O)C(=O)CN(CCCCN)C(=O)CN(CCCCN)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCc1c[nH]cn1)[C@@H](C)c1ccccc1)[C@@H](C)c1ccccc1)[C@@H](C)c1ccccc1)[C@@H](C)c1ccccc1] MK-3-61 |
| Peptoid 73 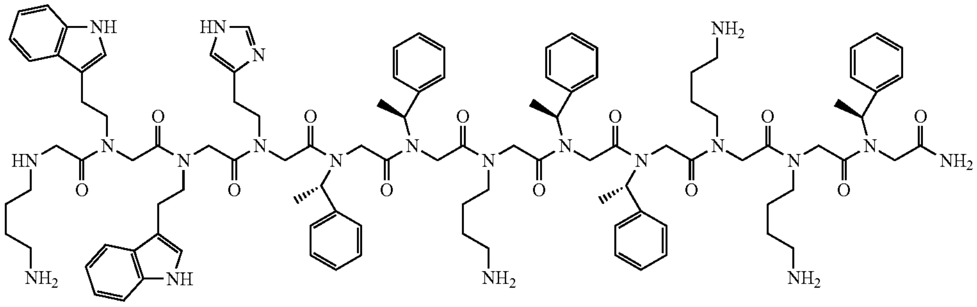 [SMILES: C[C@@H](c1ccccc1)N(CC(N)=O)C(=O)CN(CCCCN)C(=O)CN(CCCCN)C(=O)CN(C(=O)CN(C(=O)CN(CCCCN)C(=O)CN(C(=O)CN(C(=O)CN(CCc1c[nH]cn1)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1] MK-3-62 |

TABLE 20-continued
| Chemical structure |
|---|
| Peptoid 74 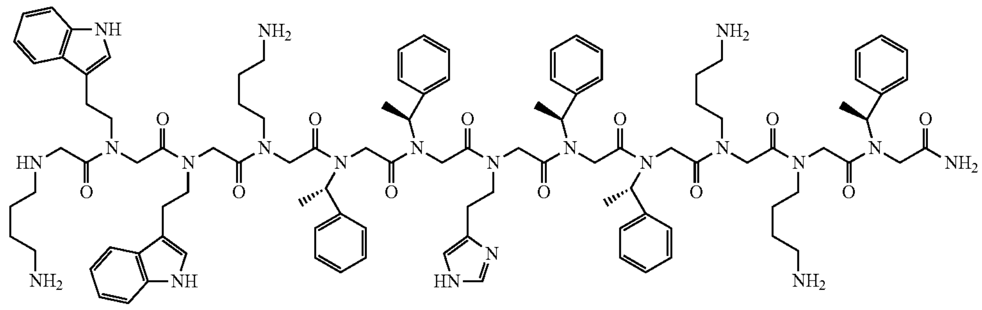 [SMILES: C[C@@H](c1ccccc1)N(CC(N)=O)C(=O)CN(CCCCN)C(=O)CN(CCCCN)C(=O)CN(C(=O)CN(C(=O)CN(CCc1c[nH]cn1)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1] MK-3-63 |
| Peptoid 75 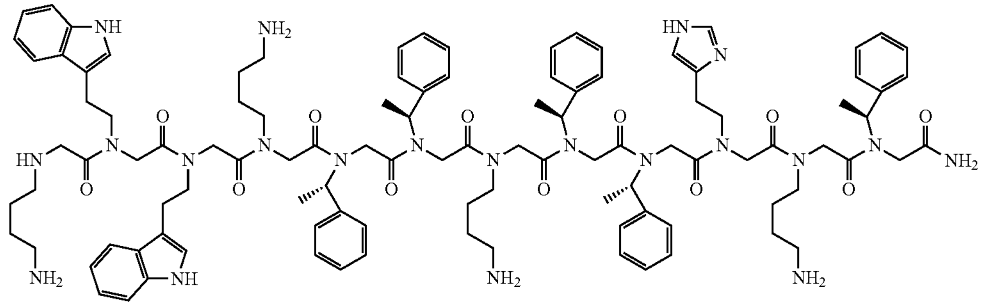 [SMILES: C[C@@H](c1ccccc1)N(CC(N)=O)C(=O)CN(CCCCN)C(=O)CN(CCc1c[nH]cn1)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1] MK-3-64 |
| Peptoid 76 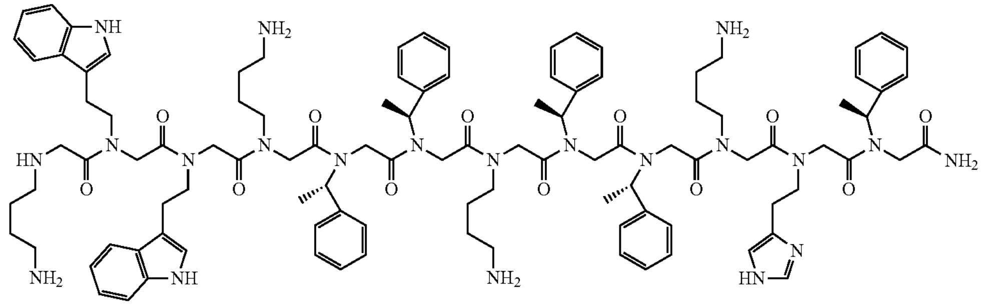 [SMILES: C[C@@H](c1ccccc1)N(CC(N)=O)C(=O)CN(CCc1c[nH]cn1)C(=O)CN(CCCCN)C(=O)CN(C(=O)CN(C(=O)CN(CCCCN)C(=O)CN(C(=O)CN(C(=O)CN(CCCCN)C(=O)CN(CCc1c[nH]c2ccccc12)C(=O)CN(CCc1c[nH]c2ccccc12)C(=O)CNCCCCN)[C@@H](C)c1ccccc1)[C@@H](C)c1ccccc1)[C@@H](C)c1ccccc1)[C@@H](C)c1ccccc1] MK-3-65 |
| Peptoid 77 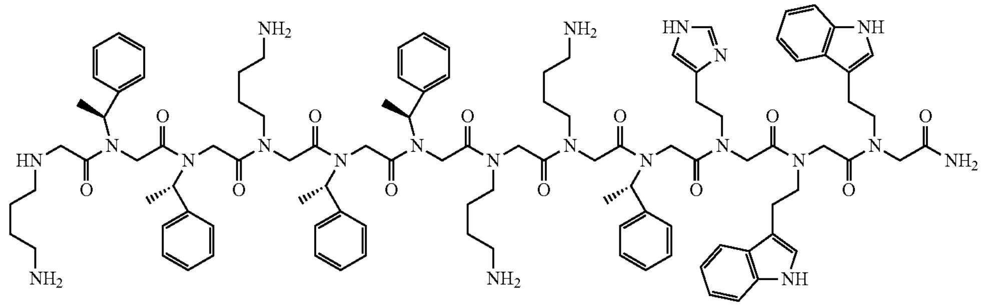 [SMILES: C[C@@H](c1ccccc1)N(CC(=O)N(CCc1c[nH]cn1)CC(=O)N(CCc1c[nH]c2ccccc12)CC(=O)N(CCc1c[nH]c2ccccc12)CC(N)=O)C(=O)CN(CCCCN)C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1] MK-3-66 |

TABLE 20-continued
| Chemical structure |
|---|
| Peptoid 78 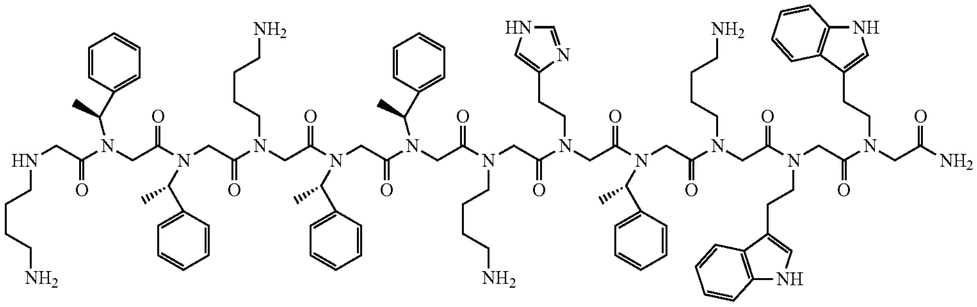 [SMILES: C[C@@H](c1ccccc1)N(CC(=O)N(CCCCN)CC(=O)N(CCc1c[nH]c2ccccc12)CC(=O)N(CCc1c[nH]c2ccccc12)CC(N)=O)C(=O)CN(CCc1c[nH]cn1)C(=O)CN(CCCCN)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1] MK-3-67 |
| Peptoid 79 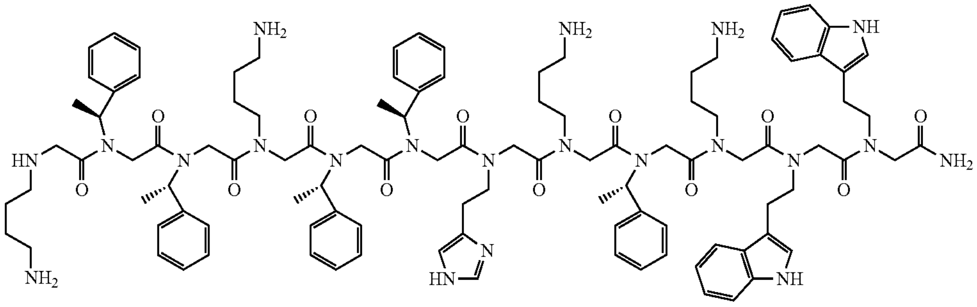 [SMILES: C[C@@H](c1ccccc1)N(CC(=O)N(CCCCN)CC(=O)N(CCc1c[nH]c2ccccc12)CC(=O)N(CCc1c[nH]c2ccccc12)CC(N)=O)C(=O)CN(CCCCN)C(=O)CN(CCc1c[nH]cn1)C(=O)CN(C(=O)CN(C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1] MK-3-68 |
| Peptoid 80 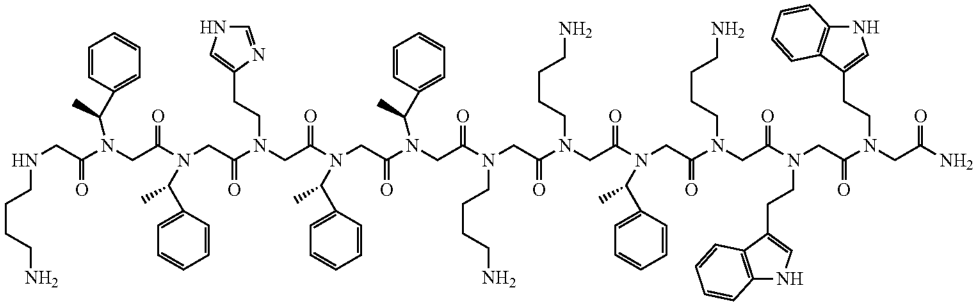 [SMILES: C[C@@H](c1ccccc1)N(CC(=O)N(CCCCN)CC(=O)N(CCc1c[nH]c2ccccc12)CC(=O)N(CCc1c[nH]c2ccccc12)CC(N)=O)C(=O)CN(CCCCN)C(=O)CN(CCCCN)C(=O)CN(C(=O)CN(C(=O)CN(CCc1c[nH]cn1)C(=O)CN(C(=O)CN(C(=O)CNCCCCN)[C@@H](C)c1ccccc1)[C@@H](C)c1ccccc1)[C@@H](C)c1ccccc1)[C@@H](C)c1ccccc1] MK-3-69 |
| Peptoid 81 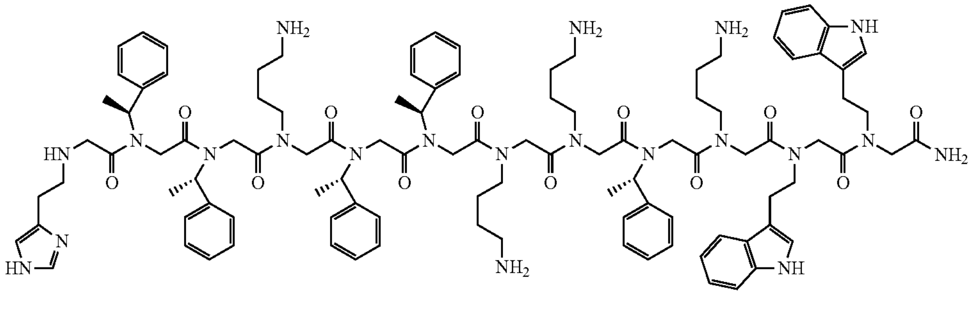 [SMILES: C[C@@H](c1ccccc1)N(CC(=O)N(CCCCN)CC(=O)N(CCc1c[nH]c2ccccc12)CC(=O)N(CCc1c[nH]c2ccccc12)CC(N)=O)C(=O)CN(CCCCN)C(=O)CN(CCCCN)C(=O)CN(C(=O)CN(C(=O)CN(CCCCN)C(=O)CN(C(=O)CN(C(=O)CNCCc1c[nH]cn1)[C@@H](C)c1ccccc1)[C@@H](C)c1ccccc1)[C@@H](C)c1ccccc1)[C@@H](C)c1ccccc1] MK-3-70 |

TABLE 21

| Peptoid | Compound | Molecular weight | Position of NHis | Net charge | CTLR | HPLC elution (% $CH_3CN$) |
|---|---|---|---|---|---|---|
| 1 | 1 | 1819.36 | — | +4 | 0.33 | 54.1 |
| 67 | MK-3-40 | 1854.37 | 5 | +6 | 0.5 | 44.1 |
| 68 | MK-3-41 | 1854.37 | 6 | +6 | 0.5 | 44.3 |
| 69 | MK-3-42 | 1854.37 | 8 | +6 | 0.5 | 44.7 |
| 70 | MK-3-43 | 1854.37 | 9 | +6 | 0.5 | 44.2 |
| 71 | MK-3-44 | 1854.37 | 12 | +6 | 0.5 | 45.6 |
| 72 | MK-3-61 | 1887.4 | 1 | +5 | 0.42 | 49.3 |
| 73 | MK-3-62 | 1887.4 | 4 | +5 | 0.42 | 49.5 |
| 74 | MK-3-63 | 1887.4 | 7 | +5 | 0.42 | 49.5 |
| 75 | MK-3-64 | 1887.4 | 10 | +5 | 0.42 | 49.2 |
| 76 | MK-3-65 | 1887.4 | 11 | +5 | 0.42 | 49.3 |
| 77 | MK-3-66 | 1887.4 | 10 | +5 | 0.42 | 48.5 |
| 78 | MK-3-67 | 1887.4 | 8 | +5 | 0.42 | 49.2 |
| 79 | MK-3-68 | 1887.4 | 7 | +5 | 0.42 | 48.9 |
| 80 | MK-3-69 | 1887.4 | 1 | +5 | 0.42 | 49.1 |
| 81 | MK-3-70 | 1887.4 | 1 | +5 | 0.42 | 49 |

Analysis Example 15: HPLC and LC-MS for Peptoids 67 to 81

FIGS. 86 to 100 show the HPLC results for antimicrobial Peptoids 67 to 81 according to Example 3 of the present inventive concept.

Table 21 shows the HPLC and LC-MS results for the antimicrobial peptoids according to Example 3 of the present inventive concept.

Referring to FIGS. 86 to 100, and Table 21, HPLC and LC-MS were performed in the same manner as in Analysis Example 1 described above. As a result, the synthesized antimicrobial peptoids generally showed a retention time in the range of 44 minutes to 50 minutes in the HPLC elution assay.

TABLE 22

| | | MIC (μM) | | | | |
|---|---|---|---|---|---|---|
| Peptoid | Compound | *E. coli* ATCC25922 | *S. aureus* ATCC25923 | $HC_{10}/HC_{50}$ | $H_{max}$ (100 μM) | Selectivity |
| 1 | 1 | 3.1 | 1.6 | 22.9/79.0 | 75.8 | 7.4 |
| — | omiganan | 12.5~25 | 12.5 | — | 0 | — |
| 67 | MK-3-40 | >25 | 25 | nd | nd | nd |
| 68 | MK-3-41 | >25 | 25 | nd | nd | nd |
| 69 | MK-3-42 | 25 | 25 | nd | nd | nd |
| 70 | MK-3-43 | >25 | >25 | nd | nd | nd |
| 71 | MK-3-44 | >25 | >25 | nd | nd | nd |
| 72 | MK-3-61 | 6.3 | 6.3 | 88.9/>100.0 | 11.8 ± 1.1 | 14.1 |
| 73 | MK-3-62 | 6.3 | 3.1 | >100.0/>100.0 | 10.0 ± 0.3 | >15.9 |
| 74 | MK-3-63 | 6.3 | 3.1 | 81.7/>100.0 | 14.2 ± 0.3 | 13 |
| 75 | MK-3-64 | 6.3 | 6.3 | 68.0/>100.0 | 18.3 ± 1.1 | 10.8 |
| 76 | MK-3-65 | 6.3 | 6.3 | >100.0/>100.0 | 10.1 ± 0.7 | >15.9 |
| 77 | MK-3-66 | 12.5 | 6.3 | >100.0/>100.0 | 3.2 ± 0.3 | >8.0 |
| 78 | MK-3-67 | 6.3 | 6.3 | >100.0/>100.0 | 5.2 ± 0.2 | >15.9 |
| 79 | MK-3-68 | 6.3 | 6.3 | >100.0/>100.0 | 8.5 ± 0.6 | >15.9 |
| 80 | MK-3-69 | 12.5 | 6.3 | >100.0/>100.0 | 4.0 ± 0.5 | >8.0 |
| 81 | MK-3-70 | 6.3 | 6.3 | >100.0/>100.0 | 5.7 ± 0.1 | >15.9 |

Table 22 shows the result of antimicrobial activity analysis for antimicrobial peptoids according to Example 3 of the present inventive concept. In Table 22, the term "nd" is the abbreviation for not determined, and indicates a value that is too small or too large to be measured.

Referring to Table 22, to measure the antimicrobial activity of the peptoids synthesized in Example 3, an MIC was measured by treating gram-negative bacteria, that is, the *E. coli* ATCC25922 strain, and gram-positive bacteria, that is, the *S. aureus* ATCC25923 strain, with the peptoids. Here, Peptoid 1 is a conventionally known antimicrobial peptoid, and Omiganan is a derivative of indolicidin, which is an antimicrobial peptide, under clinical development, and was used as a control for comparing antimicrobial activity with the novel peptoid.

A detailed method for analyzing antimicrobial activity is the same as in Analysis Example 3 described above. As a result, Peptoids 67 to 71 were prepared by substituting one Nspe in the above-described Peptoid 32 with NHis, and had low antimicrobial activity and hemolysis did not proceed. In addition, Peptoids 72, 73, 74 and 76 were prepared by substituting one NLys in Peptoid 32 with NHis, and they retained antimicrobial activity and were improved in toxicity. In addition, Peptoids 78, 79 and 81 were prepared by substituting one NLys in the above-described Peptoid 29 with NHis, and they retained antimicrobial activity and were improved in toxicity. On the other hand, Peptoids 77 and 80 exhibited reduced antimicrobial activity and improved toxicity. That is, as one Nspe or NLys in an antimicrobial peptoid was substituted with NHis, the change in antimicrobial activity of an antimicrobial peptoid could be identified.

Analysis Example 16: ESI-MS for Peptoids 67 to 81

The calculation and analysis results of ESI-MS for the antimicrobial peptoids according to Example 3 of the present inventive concept are shown in Table 23 below.

TABLE 23

| Peptoid | Compound | Calculated mass $[M+H]^+$ | Calculated mass $[M+2H]^{2+}$ | Observed mass $[M+H]^+$ | Observed mass $[M+2H]^{2+}$ |
|---|---|---|---|---|---|
| 67 | MK-3-40 | 1854.1 | 927.6 | 1854.7 | 927.9 |
| 68 | MK-3-41 | 1854.1 | 927.6 | 1854.6 | 927.9 |
| 69 | MK-3-42 | 1854.1 | 927.6 | 1854.6 | 927.9 |
| 70 | MK-3-43 | 1854.1 | 927.6 | 1854.6 | 927.9 |
| 71 | MK-3-44 | 1854.1 | 927.6 | 1854.7 | 928 |
| 72 | MK-3-61 | 1887.1 | 944.1 | 1887.8 | 944.5 |
| 73 | MK-3-62 | 1887.1 | 944.1 | 1887.7 | 944.4 |
| 74 | MK-3-63 | 1887.1 | 944.1 | 1887.7 | 944.4 |
| 75 | MK-3-64 | 1887.1 | 944.1 | 1887.8 | 944.5 |
| 76 | MK-3-65 | 1887.1 | 944.1 | 1887.7 | 944.4 |
| 77 | MK-3-66 | 1887.1 | 944.1 | 1887.8 | 944.5 |
| 78 | MK-3-67 | 1887.1 | 944.1 | 1887.7 | 944.4 |
| 79 | MK-3-68 | 1887.1 | 944.1 | 1887.8 | 944.4 |
| 80 | MK-3-69 | 1887.1 | 944.1 | 1888 | 944.7 |
| 81 | MK-3-70 | 1887.1 | 944.1 | 1887.7 | 944.7 |

Referring to Table 23, the ESI-MS result for each peptoid sample revealed that a calculated mass is the same as an observed mass, thereby confirming that a peptoid with a predicted structure and a peptoid with an actual structure are manufactured in the same manner.

Meanwhile, the embodiments of the present inventive concept shown in the specification and drawings are merely provided to present specific examples to better explain the present inventive concept, and do not limit the scope of the present inventive concept. Other than the embodiments disclosed herein, it is obvious to those of ordinary skill in the art that other modified embodiments based on the technical idea of the present invent ion can be implemented.

The invention claimed is:

1. An antimicrobial peptoid selected from one of Formulas 2 to 5 below:

H-NLys-Nspe-Nspe-NLys-Nspe-Nspe-NLys-NLys-Nspe-NLys-NhTrp-NhTrp-$NH_2$; [Formula 2]

H-NLys-NhTrp-NhTrp-NLys-Nspe-Nspe-NLys-Nspe-Nspe-NLys-NLys-Nspe-$NH_2$; [Formula 3]

H-NLys-NhTrp-NhTrp-NHis-Nspe-Nspe-NLys-Nspe-Nspe-NLys-NLys-Nspe-$NH_2$; and [Formula 4]

H-NLys-Nspe-Nspe-NLys-Nspe-Nspe-NLys-NHis-Nspe-NLys-NhTrp-NhTrp-$NH_2$. [Formula 5]

2. An antimicrobial composition, comprising the antimicrobial peptoid, selected in claim 1, as an active ingredient.

3. The antimicrobial composition of claim 2, wherein the antimicrobial peptoid exhibits antimicrobial activity against *Staphylococcus aureus* or *Escherichia coli*.

* * * * *